(12) United States Patent
Sun

(10) Patent No.: US 11,819,527 B2
(45) Date of Patent: Nov. 21, 2023

(54) SUPERABSORBENT MATERIALS AND METHODS OF MAKING THE SAME

(71) Applicant: SIMEON INVESTMENT, INC., Arcadia, CA (US)

(72) Inventor: Lijun Sun, La Canada Flintridge, CA (US)

(*) Notice: Subject to any disclaimer, the term of this patent is extended or adjusted under 35 U.S.C. 154(b) by 222 days.

(21) Appl. No.: 17/339,633

(22) Filed: Jun. 4, 2021

(65) Prior Publication Data
US 2021/0290706 A1 Sep. 23, 2021

Related U.S. Application Data

(63) Continuation of application No. 17/169,362, filed on Feb. 5, 2021, now Pat. No. 11,096,974.

(60) Provisional application No. 62/971,668, filed on Feb. 7, 2020.

(51) Int. Cl.
| | |
|---|---|
| C08J 9/28 | (2006.01) |
| C08J 3/075 | (2006.01) |
| B01J 20/24 | (2006.01) |
| A61K 36/04 | (2006.01) |
| B01J 20/28 | (2006.01) |
| B01J 20/30 | (2006.01) |
| C08J 9/00 | (2006.01) |
| A61K 36/48 | (2006.01) |
| A61K 31/736 | (2006.01) |
| A61K 31/729 | (2006.01) |
| A61K 31/731 | (2006.01) |

(52) U.S. Cl.
CPC ............ *A61K 36/04* (2013.01); *A61K 31/729* (2013.01); *A61K 31/731* (2013.01); *A61K 31/736* (2013.01); *A61K 36/48* (2013.01); *B01J 20/24* (2013.01); *B01J 20/28047* (2013.01); *B01J 20/28085* (2013.01); *B01J 20/305* (2013.01); *C08J 3/075* (2013.01); *C08J 9/0061* (2013.01); *C08J 9/0085* (2013.01); *C08J 9/28* (2013.01); *B01J 2220/44* (2013.01); *B01J 2220/68* (2013.01); *C08J 2201/0484* (2013.01); *C08J 2305/00* (2013.01); *C08J 2405/00* (2013.01)

(58) Field of Classification Search
CPC .... A61K 36/04; A61K 31/729; A61K 31/371; A61K 31/736; A61K 36/48; B01J 20/24; B01J 20/28047; B01J 20/28085; B01J 20/305; B01J 2220/44; B01J 2220/68; C08J 3/075; C08J 9/0061; C08J 9/0085; C08J 9/28; C08J 2201/0484; C08J 2035/00; C08J 2405/00; C08J 2205/02; C08J 2205/044

See application file for complete search history.

(56) References Cited

U.S. PATENT DOCUMENTS

| | | | |
|---|---|---|---|
| 6,033,769 A * | 3/2000 | Brueggemann | A61L 15/425 428/17 |
| 6,271,278 B1 | 8/2001 | Park et al. | |
| 6,479,649 B1 | 11/2002 | Tsai et al. | |
| 9,878,839 B2 * | 1/2018 | Santos | D21H 27/10 |
| 2003/0224022 A1 | 12/2003 | Nussinovitch | |
| 2006/0093720 A1 | 5/2006 | Tatz | |
| 2015/0366989 A1 | 12/2015 | Liang et al. | |
| 2017/0128574 A1 | 5/2017 | Lu et al. | |
| 2021/0115198 A1 | 4/2021 | Yorino et al. | |

FOREIGN PATENT DOCUMENTS

| | | |
|---|---|---|
| CN | 106478994 A * | 3/2017 |
| WO | 2019-221236 A1 | 11/2019 |
| WO | 2020033939 A1 | 2/2020 |
| WO | 2020257825 A1 | 12/2020 |
| WO | 2020257826 A1 | 12/2020 |

OTHER PUBLICATIONS

Ni, et al.; "The Control of Ice Crystal Growth and Effect on Porous Structure of Konjac Glucomannan-Based Aerogels"; International Journal of Biologial Macromolecules; 2016; vol. 92; pp. 1130-1135.
Takei, et al.; "Autoclavable physically-crosslinked chitosan cryogel as a wound dressing"; Journal of Bioscience and Bioengineering; 2017; vol. 125; No. 4; pp. 490-495.
Korean Intellectual Property Office; International Search Report and Written Opinion issued in PCT Application No. PCT/US2021/016806 dated Jun. 1, 2021; 11 pages.

* cited by examiner

Primary Examiner — K. Boyle
(74) Attorney, Agent, or Firm — Lin Yu; Juniv LLP

(57) ABSTRACT

Provided are superabsorbent materials composed of one or more water-soluble polysaccharides, such as gelling polysaccharides and gelling-compatible polysaccharides, and one or more insoluble fibers. The disclosed superabsorbent materials have a porous network structure and highly stable gelling properties as well as high absorption ratio and volume expansion capacity upon hydration or rehydration. Also provided are methods for preparing such superabsorbent materials and uses thereof.

20 Claims, 30 Drawing Sheets

| Sample No. | Dry | Rehydration in water (24 hours) |
|---|---|---|
| 1 |  |  |
| | Dry | Rehydration in 0.1 M HCl (24 hours) |
| |  |  |

| Sample No. | Dry | Rehydration in water (24 hours) |
|---|---|---|
| 2 |  |  |
| | Dry | Rehydration in 0.1 M HCl (24 hours) |
| |  |  |

| Sample No. | Dry | Rehydration in water (24 hours) |
|---|---|---|
| 3 |  |  |
| | Dry | Rehydration in 0.1 M HCl (24 hours) |
| |  |  |

| Sample No. | Dry | Rehydration in water (24 hours) |
|---|---|---|
| 4 |  |  |
| | Dry | Rehydration in 0.1 M HCl (24 hours) |
| |  |  |

| Sample No. | Dry | Rehydration in water (24 hours) |
|---|---|---|
| 5 |  |  |
| | Dry | Rehydration in 0.1 M HCl (24 hours) |
| |  |  |

| Sample No. | Swelled in water | Swelled in HCl |
|---|---|---|
| 1 |  |  |
| 2 |  |  |

| Sample No. | Swelled in water | Swelled in HCl |
|---|---|---|
| 3 |  |  |
| 4 |  |  |

| Sample No. | Swelled in water | Swelled in HCl |
|---|---|---|
| 5 |  | N/A |

| Sample No. | Dry | Rehydration in water | Dry | Rehydration in 0.1 M HCl |
|---|---|---|---|---|
| 6 |  |  |  |  |
| 7 |  |  |  |  |
| 8 |  |  |  |  |
| 9 |  |  |  |  |
| 10 |  |  |  |  |
| 11 |  |  |  |  |
| 12 |  |  |  |  |
| 13 |  |  |  |  |
| 14 |  |  |  |  |

| Sample No. | Rehydration in water | Rehydration in 0.1 M HCl |
|---|---|---|
| 11 | Particle expansion time course (Particle Length (10 μm) vs Time (min), rising from ~20 to ~140 by 50 min, plateau through 150 min) | n/a |

Figure 5 (continued)

| Sample No. | Swelled in water | Swelled in HCl |
|---|---|---|
| |  |  |
| 15 |  |  |
| |  |  |
| 16 |  |  |

| Sample No. | Swelled in water |
|---|---|
| 1 |  |
| 6 |  |

| Sample No. | Swelled in water |
|---|---|
| 10 |  |
| 12 |  |

| Sample No. | Swelled in water |
|---|---|
| 13 |  |
| 15 |  |

SUPERABSORBENT MATERIALS AND METHODS OF MAKING THE SAME

CROSS-REFERENCE TO RELATED APPLICATIONS

This application is a continuation of U.S. application Ser. No. 17/169,362 filed Feb. 5, 2021, which claims the benefit of priority to U.S. Provisional Application No. 62/971,668, filed Feb. 7, 2020, which is incorporated herein by reference in its entirety.

TECHNICAL FIELD

This disclosure relates to superabsorbent materials comprising one or more water-soluble polysaccharides and one or more insoluble dietary fibers, and methods of making such superabsorbent materials. Water-soluble polysaccharides include (1) gelling polysaccharides, (2) gelling-compatible polysaccharides, or (3) a combination of (1) and (2). The superabsorbent materials have various applications in the field of food and health supplement industry or as a delivery vehicle.

BACKGROUND

With the improvement of living standards, the increasing pace of life style, and at the same time reduction of exercise and irregular diet, the obese or overweight population is increasing at an alarming pace. A study recently published by The New England Journal of Medicine projected that 57.3% of today's children will be obese by age 35. Such bleak prediction highlights the devastating health problem of obesity. Obesity is a major social and economic burden worldwide accounting for two trillion dollars per year spent on healthcare of obesity-related diseases. Obesity is the underlying cause of many medical complications, such as diabetes, high blood pressure, high cholesterol and various cardiovascular and cerebrovascular diseases. The health risk of obesity is now well recognized, and as a major means to fight obesity, weight control by healthy diet and exercise has received widespread attention. Extensive research suggests that high-carbohydrate and high-fat diets are the main causes of obesity. When the consumed food contains too many calories, the body takes in more calories than it normally uses, and the excess calories will be stored in the form of fat, thereby leading to obesity. Thus, controlling the amount of food calorie intake is a key strategy in weight control.

There are many different types of weight-loss diet on the market. A variety of water-soluble natural polysaccharides are known to possess health benefits as dietary fibers with zero calories because they are undigestible by human enzymes. Attempts to use these dietary fiber materials to control calorie intake, obesity and other health problems have been made. However, these natural polysaccharides materials either cannot maintain a certain shape upon hydration or rehydration with water or gastric liquid or have poor water absorption and volume expanding capability. As such, they are cleared by the gastric system, resulting poor satiety effect. Accordingly, there is a need in the art to develop an improved dietary product that can induce satiety when a small amount of the product is consumed.

SUMMARY

The present disclosure introduces superabsorbent materials and corresponding methods and applications, which overcome various disadvantages in the current art by providing several advantageous features described below.

1) The disclosed superabsorbent material can be prepared according to the methods disclosed herein, which produces a superabsorbent material in its dried state. The dried superabsorbent material has a dense, highly-packed porous network structure. Such dense, highly-packed porous network structure is different from other spongy-type superabsorbent material that contains large pores and are characterized by a light and fluffy porous structure. Due to this dense, highly-packed porous network structure of the dried superabsorbent material, it enables the dried superabsorbent material to absorb water or acidic solution at room temperature up to body temperature of up to 200 times in less than 2 hours (such as less than 30 minutes); meanwhile, the volume expansion upon hydration or rehydration can reach up to 150 times in less than 2 hours (such as less than 30 minutes), as will be further described herein.

2) When hydrated or rehydrated in water (e.g. pH 7) or in acidic solution (e.g. pH 2 or lower), a highly stable superabsorbent material having a highly porous network structure is formed. Such porous network structure is characterized by a plurality of pores densely-populated and organized in a highly uniform pattern such as a pattern resembling a honeycomb pattern, and characterized by pore densities and average pore diameter sizes described herein.

3) The superabsorbent material is highly stable because it forms and maintains a well-defined structure for at least 24 hours (or longer) after hydration or rehydration, as characterized by certain gel strengths described herein.

4) The superabsorbent material is also highly stable because it exhibits significantly increased gel strength for at least 24 hours (or longer) after rehydration (or hydration) when compared to the gel before freezing. The incorporation of insoluble fibers enhances the gel network of the superabsorbent material such that the rehydrated (or hydrated) superabsorbent material has a significantly increased gel strength compared to the gel before freezing.

5) The disclosed superabsorbent material can readily disperse in aqueous solution and demonstrated superior gelation and gel stability by forming a homogeneous matrix including both gelling and insoluble fiber without the need of additional energy (e.g., homogenization, high shear mixing, or any mechanical mixing). Insoluble fiber generally need such additional energy to avoid bundling or recrystallization of the insoluble fibers during hydration or rehydration.

6) The soluble polysaccharides and insoluble fibers in the superabsorbent materials can expand concertedly such that the insoluble fibers expand and disperse evenly when the superabsorbent material absorbs water and expand in volume. The insoluble fibers are evenly distributed in the gel matrix and serve as fillers which interact with the soluble gelling polysaccharide and therefore, further enhances the gel network in the superabsorbent material.

7) When rehydrated or hydrated in acidic condition to mimic human gastric condition, the disclosed superabsorbent material exhibited high gel strength maintenance. This demonstrates that the disclosed superabsorbent material has strong structural integrity under human gastric conditions, which can facilitate effective performance of various applications described herein, such as suppressing appetite, enhancing satiety, or lowering calorie intake.

In one aspect, provided herein is a material comprising one or more water-soluble polysaccharides and one or more insoluble fibers, wherein the ratio by weight between the total amount of the water-soluble polysaccharides and the total amount of the insoluble fibers is between about 1:1 and about 30:1; wherein the water-soluble polysaccharides comprise (i) one or more gelling polysaccharides, (ii) one or more gelling-compatible polysaccharides, or (iii) both one or more gelling polysaccharides and one or more gelling-compatible polysaccharides; wherein the one or more water-soluble polysaccharides and the one or more insoluble fibers form a superabsorbent material having a porous network structure without chemical cross-linking; wherein the superabsorbent material has a volume expansion ratio of at least 10 times or up to 150 times in less than 2 hours; and wherein when the superabsorbent material is hydrated (or rehydrated), the porous network structure comprises a plurality of pores with a two-dimensional pore density in a range of 1 per 100 micrometers squared ($\mu m^2$) to 500 per 100 micrometers squared ($\mu m^2$) and the pores have an average diameter size in the range of 1 micrometer ($\mu m$) to 30 micrometers ($\mu m$).

In some embodiments of the superabsorbent material provided herein, the one or more gelling polysaccharides are selected from the group consisting of agar, carrageenan, konjac gum, psyllium husk, alginate, pectin, gellan, chitosan, and curdlan. In certain embodiments, the one or more gelling-compatible polysaccharides are selected from the group consisting of xanthan gum, locust bean gum, guar gum, tamarind seed gum, okara, and gum acacia. In other embodiments, the one or more insoluble fibers are selected from the group consisting of insoluble fiber in soybean fiber, insoluble fiber from seaweeds, insoluble fiber in seaweed composite materials, cellulose, insoluble hemicellulose, lignin of seeds, seed skins, roots, stems, leaves, barks from legume, whole grain, vegetables, fruits, beans, seeds, seed skins, and whole grains, oat fiber, rice fiber, corn fiber, citrus fiber, beet fiber, sugarcane fiber, coconut fiber, and compositions comprising a combination of said insoluble fibers.

In certain embodiments of the superabsorbent material provided herein, the total amount of the insoluble fibers in the superabsorbent material is between about 15% (w/w) and about 85% (w/w). In some embodiments, the total amount of the water-soluble polysaccharides in the superabsorbent material is between about 15% (w/w) and about 85% (w/w). In other embodiments of the superabsorbent material provided herein, upon hydration or rehydration at room temperature, the superabsorbent material expands in volume in less than 2 hours, and maintains a well-defined structure, as characterized by a gel strength of at least 50 grams, for at least 24 hours under a neutral pH condition or a human gastric pH condition. In yet other embodiments of the superabsorbent material provided herein, upon hydration or rehydration at room temperature, the superabsorbent material expands in volume in less than 2 hours, and maintains a well-defined structure, as characterized by a storage modulus (G') of $10^3$ to $10^6$ Pa, for at least 24 hours under a neutral pH condition or a human gastric pH condition.

In some embodiments of the superabsorbent material provided herein, upon hydration or rehydration, the superabsorbent material can form a gel without homogenizing or mechanically dispersing the insoluble fibers. In certain embodiments of the superabsorbent material provided herein, the insoluble fibers are evenly distributed in the superabsorbent material when the superabsorbent material is hydrated or rehydrated. In some embodiments, the porous network structure exhibits a honeycomb pattern when the superabsorbent material is hydrated or rehydrated. In other embodiments of the superabsorbent material provided herein, (i) the coefficient of variation of the pore density of 1 cubic millimeter ($mm^3$) subvolumes of the same superabsorbent material is less than 1, (ii) the coefficient of variation of the pore diameter size is less than 1, or (iii) the coefficient of variation of the pore density of 1 cubic millimeter ($mm^3$) subvolumes of the same superabsorbent material is less than 1 and the coefficient of variation of the pore diameter size is less than 1.

In certain embodiments of the superabsorbent material provided herein, the porous network structure has a uniform pattern that repeats in the superabsorbent material. In other embodiments, the pattern in the superabsorbent material repeats such that: (i) a micrograph of one area of the superabsorbent material can form a cross correlation peak with a micrograph of another non-overlapping area of the superabsorbent material; (ii) no less than 50% of micrographs of the same superabsorbent material classify into one class in an image classification of an image set comprising both the micrographs of the same superabsorbent material and control micrographs from a control material, wherein the image classification is based on multivariate statistical analysis, principal component analysis, or maximum likelihood under suitable classification parameters and wherein the control material is not a superabsorbent material; or (iii) both (i) and (ii).

In some embodiments of the superabsorbent material provided herein, the superabsorbent material has a highly-packed porous network structure such that upon hydration or rehydration (i) the pore density reduces 5 to 150 fold, (ii) the pore size increases 2 to 50 fold, or (iii) both (i) and (ii).

In certain embodiments, the superabsorbent material provided herein is configured so that: (i) the ratio by weight between the total amount of the water-soluble polysaccharides and the total amount of the insoluble fibers is from 2:1 to 5:1; (ii) the water-soluble polysaccharides comprise agar from a seaweed composite material from *Gracilaria*, carrageenan from a seaweed composite material from *Eucheuma*, and konjac gum; and (iii) the insoluble fibers comprise cellulose and insoluble hemicellulose from the seaweed composite materials.

In some embodiments, the superabsorbent material provided herein is configured so that: (i) the ratio by weight between the total amount of the water-soluble polysaccharides and the total amount of the insoluble fibers is from 6:1 to 12:1; (ii) the water-soluble polysaccharides comprise agar from a seaweed composite material from *Gracilaria*, xanthan gum, and a third water-soluble polysaccharide selected from the group of konjac gum and locust bean gum; (iii) the insoluble fibers comprise cellulose and insoluble hemicellulose from the seaweed composite material from *Gracilaria*.

In certain embodiments, the superabsorbent material provided herein is configured so that: (i) the ration by weight between the total amount of the water-soluble polysaccharides and the total amount of the insoluble fibers is from 2:1 to 5:1; (ii) the water-soluble polysaccharides comprise agar, konjac gum, carrageenan, and soluble hemicellulose from a soybean fiber; and (iii) the insoluble fibers comprise insoluble fiber from the soybean fiber.

In some embodiments of the superabsorbent material provided herein, the material has an absorption ratio of at least 10 times or up to 200 times of its own weight in deionized water, or at least 5 times or up to 100 times of its own weight in artificial gastric juice.

In certain embodiments of the superabsorbent material provided herein, the superabsorbent material is prepared using the steps of: dissolving one or more water-soluble polysaccharides or one or more compositions containing one or more water-soluble polysaccharides in water to form a solution; adding one or more insoluble fibers or one or more compositions containing one or more insoluble fibers to water to form a dispersion; mixing the solution containing the one or more soluble polysaccharides and the dispersion containing the one or more insoluble fibers; subjecting the mixture to suitable conditions to form a gel; freezing the gel; and drying the frozen gel to obtain the superabsorbent material.

In some embodiments of the superabsorbent material provided herein, the freezing induces cryogelation. In certain embodiments, for at least 24 hours after hydration or rehydration with water having a pH of about 7, the superabsorbent material has a gel strength that is increased by at least 90% compared to a gel strength of the gel before the freezing step. In other embodiments, for at least 24 hours after hydration or rehydration in an acidic solution, the superabsorbent material has a gel strength maintenance percentage of 80% compared to a gel strength of the gel before the freezing step. In some embodiments, the superabsorbent material is neither expanded with a gas nor digested with an enzyme prior to or during the formation of the superabsorbent material.

Also provided herein is a dietary composition comprising the superabsorbent material provided herein.

Provided herein is a superabsorbent material comprising one or more water-soluble polysaccharides, and one or more insoluble dietary fibers. The water-soluble polysaccharides disclosed herein do not contain synthetic polymers or chemically-modified polymers. Water-soluble polysaccharides include gelling polysaccharides, gelling-compatible polysaccharides, or a combination thereof. Thus, in some embodiments, the water-soluble polysaccharide is a gelling polysaccharide, including, but not limited to, agar, carrageenan (e.g. k-carrageenan), konjac gum, psyllium husk, alginate, pectin, gellan, chitosan, and curdlan. A gelling polysaccharide is a polysaccharide that can form a gel by itself. In other embodiments, the water-soluble polysaccharide is a gelling-compatible polysaccharide. A gelling-compatible polysaccharide is a polysaccharide that can form a gel when combined with another polysaccharide due to synergies between such polysaccharides. For example, when xanthan gum is combined with locust bean gum, the collective xanthan gum-locust bean gum composition can form a gel due to the synergies between xanthan gum and locust bean gum. However, xanthan gum and locust bean gum, each by itself, cannot form a gel. Thus, in some embodiments, the gelling-compatible polysaccharide, includes, but not limited to, xanthan gum, locust bean gum, guar gum, tamarind seed gum, okara, and gum acacia.

In some embodiments of the superabsorbent material provided herein, the one or more water-soluble polysaccharides comprise one or more gelling polysaccharides. In one specific embodiment, the one or more water-soluble polysaccharides comprise one gelling polysaccharide. In another specific embodiment, the one or more water-soluble polysaccharides comprise two gelling polysaccharides. In a further embodiment, the one or more water-soluble polysaccharides comprise three gelling polysaccharides. In yet another embodiment, the one or more water-soluble polysaccharides comprise four gelling polysaccharides. In yet a further embodiment, the one or more water-soluble polysaccharides comprise five gelling polysaccharides. In some additional embodiments, the one or more water-soluble polysaccharides comprise 6, 7, 8, 9, or 10 gelling polysaccharides. As is clear from the disclosure, the gelling polysaccharides in this paragraph can be any of the gelling polysaccharides provided herein.

In certain embodiments, the one or more water-soluble polysaccharides comprise one or more gelling-compatible polysaccharides. In one specific embodiment, the one or more water-soluble polysaccharides comprise one gelling-compatible polysaccharide. In another specific embodiment, the one or more water-soluble polysaccharides comprise two gelling-compatible polysaccharides. In a further embodiment, the one or more water-soluble polysaccharides comprise three gelling-compatible polysaccharides. In yet another embodiment, the one or more water-soluble polysaccharides comprise four gelling-compatible polysaccharides. In yet a further embodiment, the one or more water-soluble polysaccharides comprise five gelling-compatible polysaccharides. In some additional embodiments, the one or more water-soluble polysaccharides comprise 6, 7, 8, 9, or 10 gelling-compatible polysaccharides. As is clear from the disclosure, the gelling-compatible polysaccharides in this paragraph can be any of the gelling-compatible polysaccharides provided herein.

In some further embodiments of the superabsorbent material provided herein, the one or more water-soluble polysaccharides comprise both one or more gelling polysaccharides and one or more gelling-compatible polysaccharides. In one specific embodiment, the one or more water-soluble polysaccharides comprise 1 gelling polysaccharide and 1, 2, 3, 4, 5, 6, 7, 8, or 9 gelling-compatible polysaccharides. In another specific embodiment, the one or more water-soluble polysaccharides comprise two gelling polysaccharides and 1, 2, 3, 4, 5, 6, 7, 8, or 9 gelling-compatible polysaccharides. In a further embodiment, the one or more water-soluble polysaccharides comprise three gelling polysaccharides and 1, 2, 3, 4, 5, 6, 7, 8, or 9 gelling-compatible polysaccharides. In yet another embodiment, the one or more water-soluble polysaccharides comprise four gelling polysaccharides and 1, 2, 3, 4, 5, 6, 7, 8, or 9 gelling-compatible polysaccharides. In yet a further embodiment, the one or more water-soluble polysaccharides comprise five gelling polysaccharides and 1, 2, 3, 4, 5, 6, 7, 8, or 9 gelling-compatible polysaccharides. In some additional embodiments, the one or more water-soluble polysaccharides comprise 6, 7, 8, 9, or 10 gelling polysaccharides and 1, 2, 3, 4, 5, 6, 7, 8, or 9 gelling-compatible polysaccharides. As is clear from the disclosure, the gelling polysaccharides in this paragraph can be any of the gelling polysaccharides provided herein and the gelling-compatible polysaccharides in this paragraph can be any of the gelling-compatible polysaccharides provided herein.

In some embodiments, the ratio by weight between the total water-soluble polysaccharide to total insoluble fiber in the superabsorbent material is about 1:1, about 2:1, about 3:1, about 4:1, about 5:1, about 6:1, about 7:1, about 8:1, about 9:1, about 10:1, about 11:1, about 12:1, about 13:1, about 14:1, about 15:1, about 16:1, about 17:1, about 18:1, about 19:1, about 20:1, about 21:1, about 22:1, about 23:1, about 24:1, about 25:1, about 26:1, about 27:1, about 28:1, about 29:1, or about 30:1, such that the obtained the superabsorbent material retains the ability to form a gel upon hydration or rehydration. Thus, in some embodiments, the ratio by weight between (i) the total gelling polysaccharides, the total gelling-compatible polysaccharides, or the combination thereof, to (ii) the total insoluble fiber is about 1:1, about 2:1, about 3:1, about 4:1, about 5:1, about 6:1, about 7:1, about 8:1, about 9:1, about 10:1, about 11:1, about 12:1, about 13:1, about 14:1, about 15:1, about 16:1, about 17:1, about 18:1, about 19:1, about 20:1, about 21:1, about 22:1, about 23:1, about 24:1, about 25:1, about 26:1, about 27:1, about 28:1, about 29:1, or about 30:1, such that the obtained the superabsorbent material retains the ability to form a gel upon hydration or rehydration.

In some embodiments, the total insoluble fiber in the superabsorbent material is between about 15% (w/w) and about 85% (w/w), such as about 15% (w/w), about 20% (w/w), about 25% (w/w), about 30% (w/w), about 35% (w/w), about 40% (w/w), about 45% (w/w), about 50% (w/w), about 55% (w/w), about 60% (w/w), about 65% (w/w), about 70% (w/w), about 75% (w/w), about 80% (w/w), or about 85% (w/w). For example, when the superabsorbent material is dehydrated (e.g. after the superabsorbent material is prepared according to the methods disclosed herein), the total soluble polysaccharides in the dehydrated superabsorbent material is between about 15% (w/w) and about 85% (w/w), such as about 15% (w/w), about 20% (w/w), about 25% (w/w), about 30% (w/w), about 35% (w/w), about 40% (w/w), about 45% (w/w), about 50% (w/w), about 55% (w/w), about 60% (w/w), about 65% (w/w), about 70% (w/w), about 75% (w/w), about 80% (w/w), or about 85% (w/w). As is commonly understood in the art, "w/w" refers to "weight by weight," which is the weight of the respective component divided by the total weight of the sample.

In some embodiments, the total gelling polysaccharides, the total gelling-compatible polysaccharides, or the combination thereof, in the superabsorbent material is between about 15% (w/w) and about 85% (w/w) such as about 15% (w/w), about 20% (w/w), about 25% (w/w), about 30% (w/w), about 35% (w/w), about 40% (w/w), about 45% (w/w), about 50% (w/w), about 55% (w/w), about 60% (w/w), about 65% (w/w), about 70% (w/w), about 75% (w/w), about 80% (w/w), or about 85% (w/w). For example, when the superabsorbent material is dehydrated, the total gelling polysaccharides, the total gelling-compatible polysaccharides, or the combination thereof, in the dehydrated superabsorbent material is between about 15% (w/w) and about 85% (w/w) such as about 15% (w/w), about 20% (w/w), about 25% (w/w), about 30% (w/w), about 35% (w/w), about 40% (w/w), about 45% (w/w), about 50% (w/w), about 55% (w/w), about 60% (w/w), about 65% (w/w), about 70% (w/w), about 75% (w/w), about 80% (w/w), or about 85% (w/w).

In some embodiments, the water-soluble polysaccharides include but are not limited to agar, carrageenan, gums such as konjac gum, locust bean gum, xanthan gum, gellan gum, Arabic gum, tamarind seed gum, guar gum, okara, alginate (such as sodium alginate), pectin, β-glucan, chitosan, galactomannans, glucomannans, and a soluble starch or a soluble dietary fiber such as Psyllium fiber. In some embodiments, the insoluble dietary fibers include but are not limited to insoluble fiber in soybean fiber, insoluble fiber from seaweeds (such as Rhodophyta, Phaeophyta, Chlorophyta), seaweed composite materials, cellulose, insoluble hemicellulose, lignin of seeds, seed skins, roots, stems, leaves, barks from legume, wheat bran, whole grain, vegetables, fruits, beans, seeds, seed skins, oat fiber, rice fiber, oak fiber, corn fiber, citrus fiber, beet fiber, sugarcane fiber, coconut fiber, and compositions comprising a combination of said insoluble fibers.

In some embodiments, the insoluble dietary fibers and the water-soluble polysaccharides, such as total gelling polysaccharides, total gelling-compatible polysaccharides, and combination thereof, are present in a composite material, such as a seaweed composite material or a soybean fiber, as disclosed herein and in PCT No. PCT/US2021/014388, filed on Jan. 21, 2021, which is incorporated herein in its entirety by reference, PCT Application No. PCT/US2020/070160, filed on Jun. 19, 2020 and published as WO2020/257825 on Dec. 24, 2020 (which is herein incorporated in its entirety by reference), and PCT Application No. PCT/US2020/070161, filed on Jun. 19, 2020 and published as WO2020/257826 on Dec. 24, 2020 (which is herein incorporated in its entirety by reference). Thus, in certain embodiments, the superabsorbent material disclosed herein includes a seaweed composite material comprising one or more insoluble fibers (e.g. cellulose, insoluble hemicellulose) and agar, as disclosed herein and as further described in PCT Application No. PCT/US2020/070160, filed on Jun. 19, 2020 and published as WO2020/257825 on Dec. 24, 2020 (which is herein incorporated in its entirety by reference). In other embodiments, the superabsorbent material disclosed herein includes a seaweed composite material comprising one or more insoluble fibers (e.g. cellulose, insoluble hemicellulose) and carrageenan, as disclosed herein further described in PCT Application No. PCT/US2020/070161, filed on Jun. 19, 2020 and published as WO2020/257826 on Dec. 24, 2020 (which is herein incorporated in its entirety by reference). WO2020/257825 and WO2020/257826, as well as this present disclosure, also disclose methods for making seaweed composite material that is less processed compared to conventional methods because the disclosed methods maintains the natural association between the insoluble fiber (e.g. cellulose, insoluble hemicellulose) and polysaccharide (e.g. agar, carrageenan) without any substantial disruption or dissociation of the polysaccharide from the insoluble fiber. Thus, the obtained seaweed composite material comprises one or more insoluble fibers and polysaccharide associated with the insoluble fiber. Similarly, as disclosed herein and as disclosed in PCT Application No. PCT/US2021/014388, filed on Jan. 21, 2021, which is incorporated herein in its entirety by reference, the soybean fiber comprises insoluble fibers and soluble fibers, such as about 70%-90% (w/w) insoluble fiber and 5%-20% (w/w) soluble fiber. See Table 5 in PCT Application No. PCT/US2021/014388, filed on Jan. 21, 2021, which is incorporated herein in its entirety by reference.

In some embodiments of the superabsorbent material is configured so that the total amount of the water-soluble polysaccharide to the total amount of the insoluble fiber is at a ratio by weight from 2:1 to 5:1; the total amount of the water-soluble polysaccharide includes agar from a seaweed composite material from *Gracilaria*, carrageenan from a seaweed composite material from *Eucheuma*, and konjac gum; and the total amount of the insoluble fiber includes cellulose and insoluble hemicellulose from the seaweed composite materials.

In some embodiments of the superabsorbent material is configured so that the total amount of the water-soluble polysaccharide to the total amount of the insoluble fiber is at a ratio by weight from 6:1 to 12:1; the total amount of the water-soluble polysaccharide includes agar from a seaweed composite material from *Gracilaria*, xanthan gum, and a third water-soluble polysaccharide selected from the group of konjac gum and locust bean gum; and the total amount of the insoluble fiber includes cellulose and insoluble hemicellulose from the seaweed composite material from *Gracilaria*.

In some embodiments of the superabsorbent material is configured so that the total amount of the water-soluble polysaccharide to the total amount of the insoluble fiber is at a ratio by weight from 2:1 to 5:1; the total amount of the water-soluble polysaccharide includes agar, konjac gum, carrageenan, and soluble hemicellulose from a soybean fiber; and the total amount of the insoluble fiber includes insoluble fiber from the soybean fiber.

The disclosed superabsorbent material has a porous network structure that is highly stable in the drying and hydration or rehydration processes under neutral and low pH solution mimicking human gastric condition. The superabsorbent material is characterized by high swelling capacity at room temperature (for example, at a temperature of 25° C., 25±1° C., 25±2° C., 25±3° C., 25±4° C., 25±5° C., 20-42° C., or between 15° C. and 25° C.), or at human body temperature (for example, at a temperature of 37° C., 37±1° C., 37±2° C., or between 35° C. and 41° C.), and under a neutral pH condition or a human gastric pH condition. For example, upon hydration or rehydration, the superabsorbent material can expand in volume significantly, such as at a ratio of at least 10 times to up to 150 times, and expand its volume rapidly in less than 2 hours, less than 1.5 hours, less than 1 hour, less than 30 minutes, less than 25 minutes, or less than 15 minutes and maintain a well-defined structure, as characterized by maintaining a certain gel strength or a certain storage modulus (G') as further described below, for at least 24 hours, at least 36 hours, or at least 48 hours under a neutral pH condition or a human gastric pH condition. In some embodiments, the superabsorbent material can expand in volume of at least 30 times and expand its volume rapidly in less than 30 minutes, form a highly stable gel upon hydration or rehydration by maintaining a well-defined structure, as characterized by maintaining a certain gel strength or a certain storage modulus (G') as further described below, for at least 24 hours under a neutral pH condition or a human gastric pH condition.

With respect to maintaining a well-defined structure after hydration or rehydration, the superabsorbent material can maintain a gel strength of at least 50 grams (g) for at least 24 hours or more under a neutral pH condition or a human gastric pH condition. In other embodiments, the superabsorbent material can maintain a gel strength of at least 75 g, at least 100 g, at least 125 g, at least 150 g, at least 175 g, at least 200 g, at least 225 g, at least 250 g, at least 275 g, at least 300 g, at least 325 g, at least 350 g, at least 375 g, at least 400 g, at least 425 g, at least 450 g, at least 475 g, at least 500 g, or more, for at least 24 hours or more under a neutral pH condition or a human gastric pH condition.

Also, with respect to maintaining a well-defined structure after hydration or rehydration, the superabsorbent material can maintain a storage modulus (G') of $10^3$ Pa to $10^6$ Pa for at least 24 hours or more under a neutral pH condition or a human gastric pH condition. In some embodiments, the superabsorbent material can hydrated or rehydrate at a temperature below 40° C. (e.g. human body temperature, or room temperature) and maintain a well-defined structure, as characterized by maintaining a storage modulus (G') of $10^3$ Pa to $10^6$ Pa, at least 24 hours or more under a neutral pH condition or a human gastric pH condition. In certain embodiments, the superabsorbent material can hydrate or rehydrate at a temperature below 40° C. (e.g. human body temperature, or room temperature) and maintain a well-defined structure, as characterized by maintaining a storage modulus (G') of about $10^3$ Pa, about $1.5\times10^3$ Pa, about $2\times10^3$ Pa, about $2.5\times10^3$ Pa, about $3\times10^3$ Pa, about $3.5\times10^3$ Pa, about $4\times10^3$ Pa, about $4.5\times10^3$ Pa, about $5\times10^3$ Pa, about $5.5\times10^3$ Pa, about $6\times10^3$ Pa, about $6.5\times10^3$ Pa, about $7\times10^3$ Pa, about $7.5\times10^3$ Pa, about $8\times10^3$ Pa, about $8.5\times10^3$ Pa, about $9\times10^3$ Pa, about $9.5\times10^3$ Pa, about $10^4$ Pa, about $1.5\times10^4$ Pa, about $2\times10^4$ Pa, about $2.5\times10^4$ Pa, about $3\times10^4$ Pa, about $3.5\times10^4$ Pa, about $4\times10^4$ Pa, about $4.5\times10^4$ Pa, about $5\times10^4$ Pa, about $5.5\times10^4$ Pa, about $6\times10^4$ Pa, about $6.5\times10^4$ Pa, about $7\times10^4$ Pa, about $7.5\times10^4$ Pa, about $8\times10^4$ Pa, about $8.5\times10^4$ Pa, about $9\times10^4$ Pa, about $9.5\times10^4$ Pa, about $10^5$ Pa, about $1.5\times10^5$ Pa, about $2\times10^5$ Pa, about $2.5\times10^5$ Pa, about $3\times10^5$ Pa, about $3.5\times10^5$ Pa, about $4\times10^5$ Pa, about $4.5\times10^5$ Pa, about $5\times10^5$ Pa, about $5.5\times10^5$ Pa, about $6\times10^5$ Pa, about $6.5\times10^5$ Pa, about $7\times10^5$ Pa, about $7.5\times10^5$ Pa, about $8\times10^5$ Pa, about $8.5\times10^5$ Pa, about $9\times10^5$ Pa, about $9.5\times10^5$ Pa, about $10^6$ Pa, or any range between any two storage modulus listed in this sentence. In further embodiment, the superabsorbent material can hydrate or rehydrate at a temperature below 40° C. (e.g. human body temperature, or room temperature) and maintain a well-defined structure as described in this paragraph for at least 2, 3, 4, 5, 6, 7, 8, 9, 10, 12, 14, 16, 18, 20, 22, 24, 30, 36, 42, 48, 54, 60, 66, or 72 hours. In other embodiments, the superabsorbent material can hydrate or rehydrate at a temperature below 40° C. (e.g. human body temperature, or room temperature) and maintain a well-defined structure as described in this paragraph for any duration as described in this paragraph.

Also, advantageously, the superabsorbent material can rapidly expand in volume at room temperature, as described above, without needing homogenization or high shear mixing to activate the insoluble fibers. This is highly advantageous because most insoluble fibers would generally need activation from homogenization or high shear mixing to prevent or reduce the bundling of the insoluble fibers in the gel when the a material including such insoluble fibers is hydrated or rehydrated. In some embodiments, the swelling capacity of the superabsorbent materials is measured by absorption ratio calculated by the formula: the weight of fully hydrated or rehydrated sample divided by the weight of dry sample. In certain embodiments, the superabsorbent material disclosed herein has an absorption ratio of at least 10 times or up to 200 times of its own weight in deionized water. In other embodiments of the superabsorbent materials provided herein, the superabsorbent material disclosed herein has an absorption ratio of at least 5 times, at least 10 times, at least 15 times, at least 20 times, at least 25 times, at least 30 times, at least 35 times, at least 40 times, at least 45 times, at least 50 times, at least 55 times, at least 60 times, at least 65 times, at least 70 times, at least 75 times, at least 80 times, at least 85 times, at least 90 times, at least 95 times, at least 100 times, at least 105 times, at least 110 times, at least 115 times, at least 120 times, at least 125 times, at least 130 times, at least 135 times, at least 140 times, at least 145 times, at least 150 times, at least 155 times, at least 160 times, at least 165 times, at least 170 times, at least 175 times, at least 180 times, at least 185 times, at least 190 times, at least 195 times, at least 200 times, or up to 200 times in deionized water. In some embodiments, the volume expansion capacity of the superabsorbent materials is measured by volume expansion ratio calculated by a formula: the volume of fully hydrated or rehydrated sample divided by the volume of dry sample. In some embodiments of the superabsorbent materials provided herein, the superabsorbent material disclosed herein has a volume expansion ratio of at least 5 times, at least 10 times, at least 15 times, at least 20 times, at least 25 times, at least 30 times, at least 35 times, at least 40 times, at least 45 times, at least 50 times, at least 55 times, at least 60 times, at least 65 times, at least 70 times, at least 75 times, at least 80 times, at least 85 times, at least 90 times, at least 95 times, at least 100 times, at least 105 times, at least 110 times, at least 115 times, at least 120 times, at least 125 times, at least 130 times, at least 135 times, at least 140 times, at least 145 times, or up to 150 times in deionized water. The superabsorbent materials can be obtained by the process disclosed herein.

Current technologies such as hydrocolloid solid matrix materials has a sponge-like composition, which can absorb water but does not have volume expansion capabilities. Common knowledge suggests that a dry sponge may absorb water and gain weight, but its volume does not expand significantly upon hydration or rehydration. This is different from the claimed superabsorbent material, which forms a gel upon hydration or rehydration at room temperature or body temperature and significantly expands in volume—up to several hundred folds, while maintaining its structure and non-aggregated state under gastric and neutral pH.

In another aspect, provided herein is a dietary composition comprising the superabsorbent material described above. In another aspect, provided herein is a volumetric diet comprising the superabsorbent material or the dietary composition disclosed herein.

In another aspect, provided herein is a method of preventing or treating a disease or condition associated with abnormal metabolism. The method comprises orally administering to a subject suffering from or at an elevated risk of a disease or condition associated with abnormal metabolism an effective amount of the superabsorbent material, the dietary composition comprising the superabsorbent material or the volumetric diet described above. In some embodiments, the disease or condition associated with abnormal metabolism includes but is not limited to diabetes, obesity, overweight, high cholesterol, and high blood pressure.

In another aspect, provided herein is a method of suppressing appetite, enhancing satiety, or lowering calorie intake in a subject. The method comprises orally administering to a subject in need thereof an effective amount of the superabsorbent material, the dietary composition comprising the superabsorbent material or the volumetric diet described above.

In yet another aspect, provided herein is a method of preparing a superabsorbent material comprising one or more water-soluble polysaccharides, such as gelling polysaccharides, gelling-compatible polysaccharides, or combination thereof, and one or more insoluble dietary fiber. The disclosed superabsorbent material can be prepared using such method comprising the steps of dissolving one or more water-soluble polysaccharides, such as gelling polysaccharides, gelling-compatible polysaccharides, or combination thereof, or one or more compositions containing one or more water-soluble polysaccharides, such as gelling polysaccharides, gelling-compatible polysaccharides, or combination thereof, in water to form a solution, adding one or more insoluble fibers or one or more compositions containing one or more insoluble fibers to water to form a dispersion, which is optionally subjected to high pressure homogenization (e.g. at a pressure of 10-50 MPa), mixing the solution containing the one or more soluble polysaccharides and the dispersion containing the one or more insoluble fibers, subjecting the mixture to suitable conditions to form a gel, freezing the gel, and drying the frozen gel to obtain the superabsorbent material. In some embodiments, the drying step comprises thawing the gel and drying under atmospheric pressure at 50-60° C. ("thawing-dry"). In some embodiments, the freezing the gel step induces cryogelation. In some embodiments, the freezing step to induce cryogelation is performed at a temperature of −5° C. to −80° C. for at least 6 hours. In some embodiments, the drying step comprises directly drying the frozen gel by lyophilization without thawing ("freeze-dry"). In some embodiments, the method further comprises pulverizing the dried gel to obtain the superabsorbent material in a powder form of various mesh sizes.

In a further aspect, provided herein is a method of preparing a superabsorbent material comprising: dissolving one or more water-soluble polysaccharides or one or more compositions containing one or more water-soluble polysaccharides in water to form a solution; adding one or more insoluble fibers or one or more compositions containing one or more insoluble fibers to water to form a dispersion; mixing the solution containing the one or more soluble polysaccharides and the dispersion containing the one or more insoluble fibers; subjecting the mixture to suitable conditions to form a gel; freezing the gel; and drying the frozen gel to obtain the superabsorbent material.

In one embodiment of the methods provide herein, the freezing is to induce cryogelation. In another embodiment of the methods provide herein, the freezing induces cryogelation. In a further embodiment, the freezing step is performed at a temperature of −5° C. to −80° C. for at least 6 hours. In yet another embodiment, the method further comprises subjecting the dispersion to high pressure homogenization at a pressure of 10-50 MPa before mixing with the solution. In one embodiment of the methods provide herein, the drying step comprises thawing the gel and drying under atmospheric pressure at 50-60° C. In another embodiment of the methods provide herein, the drying step comprises directly drying the frozen gel by lyophilization without thawing. In a further embodiment of the methods provide herein, the methods further comprise pulverizing the dried gel to obtain the superabsorbent material in a powder form.

In some embodiments of the methods provide herein, the one or more insoluble fibers are selected from the group consisting of insoluble fiber in soybean fiber, insoluble fiber from seaweeds, insoluble fiber in seaweed composite material, cellulose, insoluble hemicellulose, lignin of seeds, seed skins, roots, stems, leaves, barks from legume, whole grain, vegetables, fruits, beans, seeds, seed skins, and whole grains, oat fiber, rice fiber, corn fiber, citrus fiber, beet fiber, sugarcane fiber, coconut fiber, and compositions comprising a combination of said insoluble fibers.

In another aspect, provided herein is a superabsorbent material obtained by the method provided herein.

Advantageously, in some embodiments, for at least 24 hours after hydration or rehydration with water at room temperature, the superabsorbent material has a gel strength that is increased by 75% to 250%, or any range subsumed therein, compared to a gel strength of the gel before the freezing step described above. In other embodiments, said increase gel strength includes 90% to 200%.

In further embodiments, for at least 24 hours after hydration or rehydration with water at room temperature, the superabsorbent material has an increased gel strength that is increased by at least 75%, at least 80%, at least 85%, at least 90%, at least 95%, at least 100%, at least 105%, at least 110%, at least 120%, at least 140%, at least 160%, at least 180%, or more compared to a gel strength of the gel before the freezing step described above. In other embodiments, the superabsorbent material can maintain said increased gel strengths for at least 36 hours, at least 48 hours, at least 72 hours, or more after hydration or rehydration.

In some embodiments, the water-soluble polysaccharides include but are not limited to agar, carrageenan, gums such as konjac gum, locust bean gum, xanthan gum, gellan gum, Arabic gum, tamarind seed gum and guar gum, okara, alginate (such as sodium alginate), pectin, β-glucan, chitosan, galactomannans, glucomannans, and a soluble starch or soluble dietary fiber such as Psyllium fiber. In some embodiments, the water-soluble polysaccharide is a gelling polysaccharide, including, but not limited to, carrageenan (e.g. k-carrageenan), konjac gum, psyllium husk, alginate, pectin, gellan, chitosan, and curdlan. In other embodiments, the water-soluble polysaccharide is a gelling-compatible polysaccharide, including, but not limited to, xanthan gum, locust bean gum, guar gum, tamarind seed gum, okara, and gum acacia. In some embodiments, the insoluble dietary fibers include but are not limited to insoluble fiber in soybean fiber, insoluble fiber from seaweeds (such as Rhodophyta, Phaeophyta, Chlorophyta), seaweed composite materials, cellulose, insoluble hemicellulose, lignin of seeds, seed skins, roots, stems, leaves, barks from legume, wheat bran, whole grain, vegetables, fruits, beans, seeds, seed skins, oat fiber, rice fiber, oak fiber, corn fiber, citrus fiber, beet fiber, sugarcane fiber, coconut fiber, and compositions comprising a combination of said insoluble fibers.

In a related aspect, provided herein is a superabsorbent material produced by the methods described above. The superabsorbent material produced by the disclosed methods can be used in food or health supplement industry and/or as delivery vehicle for therapeutic agents and/or nutrients.

BRIEF DESCRIPTION OF THE DRAWINGS

This application contains at least one drawing executed in color. Copies of this application with color drawing(s) will be provided by the Office upon request and payment of the necessary fees.

FIG. 2A shows the particle expansion time course in a curve. The volume expanded about 2 (length)×2 (width)×7.5 (height)=30 fold, reached 90% max volume in less than 30 minutes. FIG. 2B shows a series of images demonstrating that most of the insoluble fibers were expanded and distributed evenly during the volume expansion process. A single particle of Sample No. 1 was soaked in deionized water for over four hours and the status of the particle in water was recorded in pictures by Leica MZ125 at different time points under polarized light. The bright materials shown under polarized light are insoluble fibers. The smallest division of the scale in the figure is 10 μm.

DETAILED DESCRIPTION

Composite Superabsorbent Materials

Figure 1A:
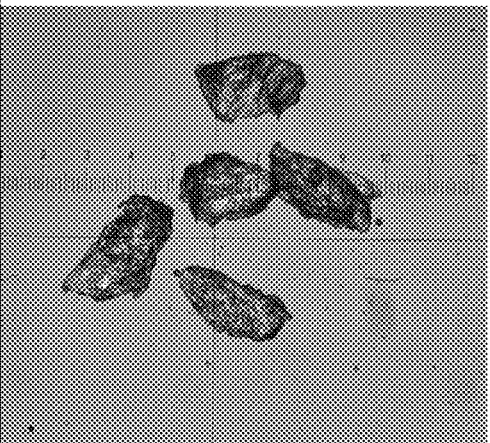
FIGS. 1A-1E show the light microscope images of Sample Nos. 1-5 of the superabsorbent materials before and after soaking in deionized water and 0.1 M HCl. The smallest division of the scale in the figure is 10 μm.
Figure 1A:
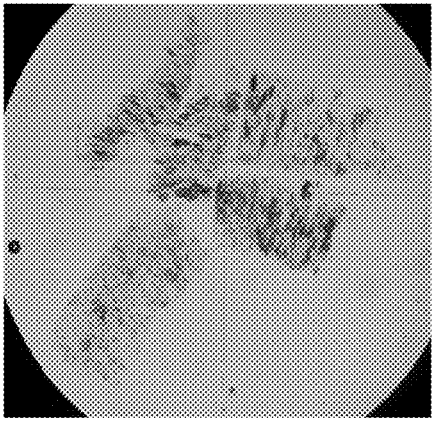
Figure 1A:
Figure 1A:
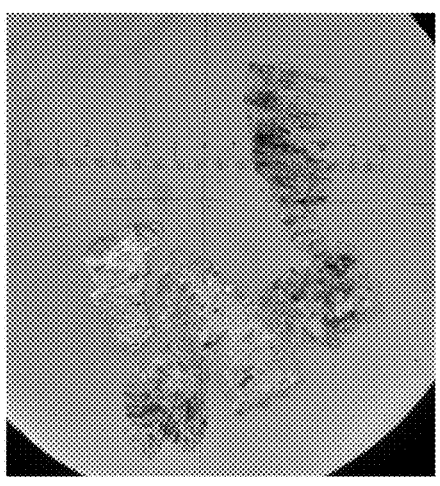
Figure 1B:
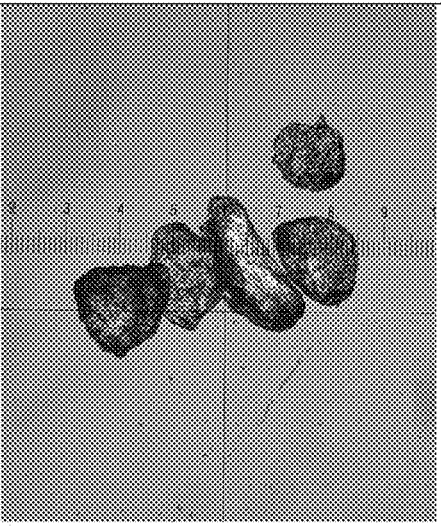
Figure 1B:
Figure 1B:
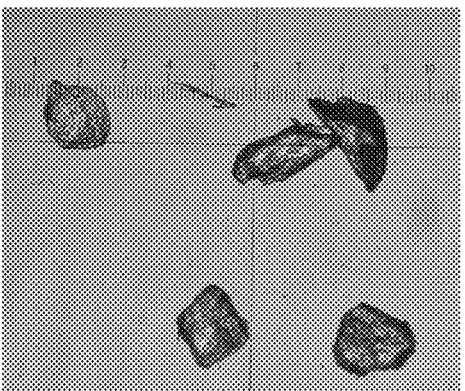
Figure 1B:
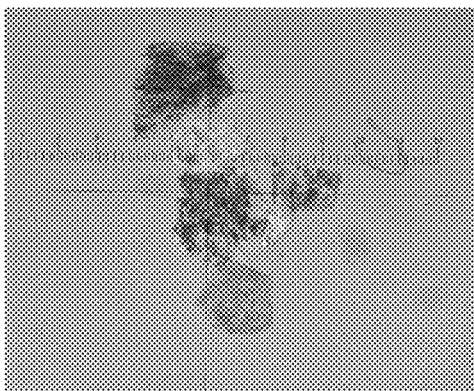
Figure 1C:
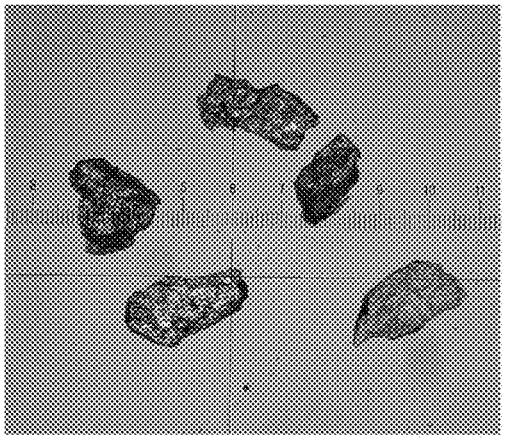
Figure 1C:
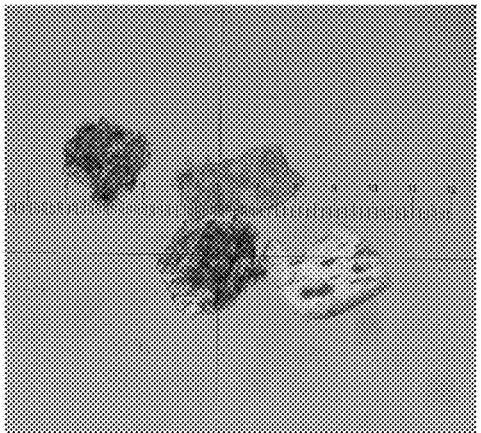
Figure 1C:
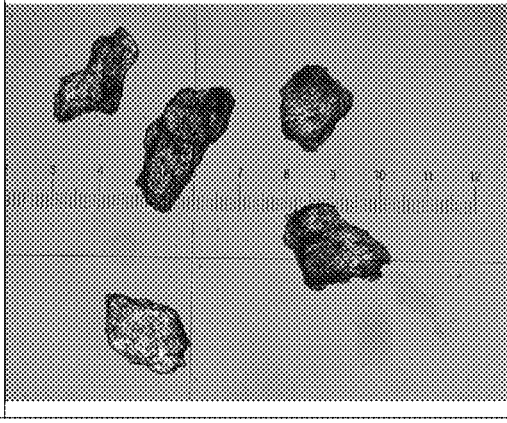
Figure 1C:
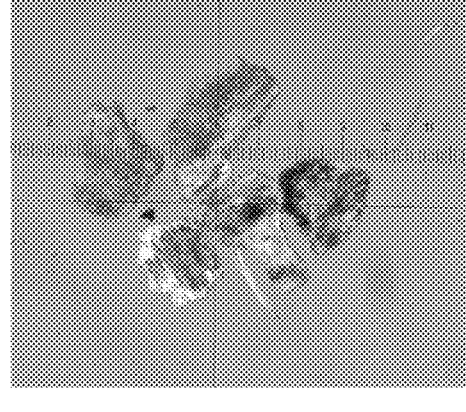
Figure 1D:
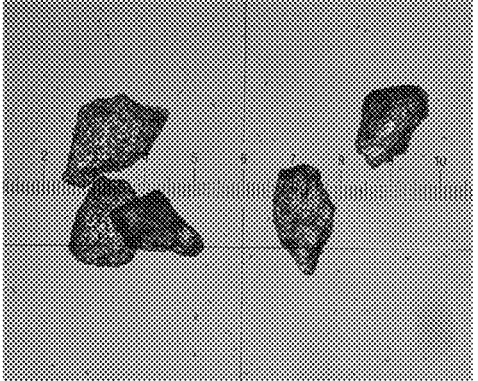
Figure 1D:
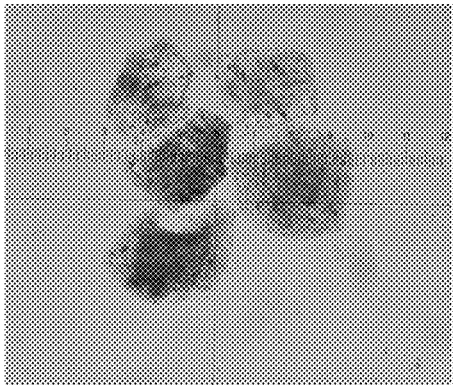
Figure 1D:
Figure 1D:
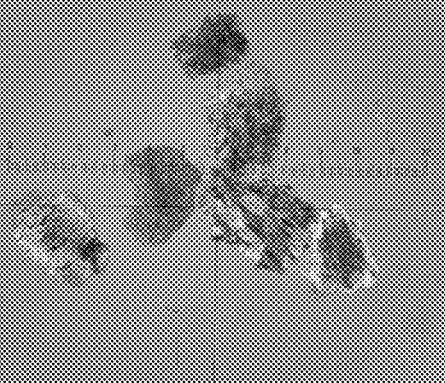
Figure 1E:
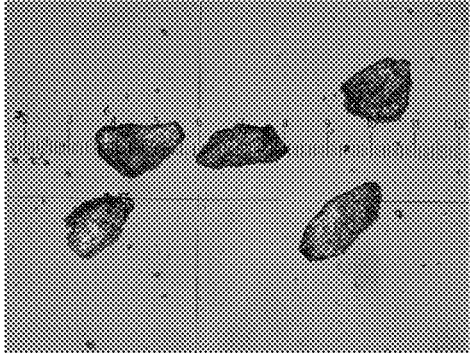
Figure 1E:
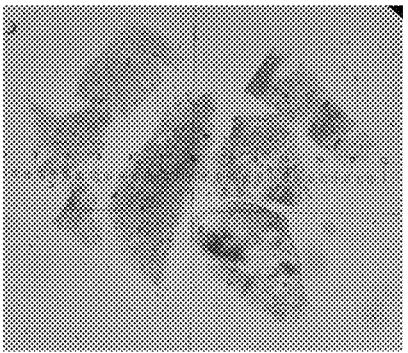
Figure 1E:
Figure 1E:
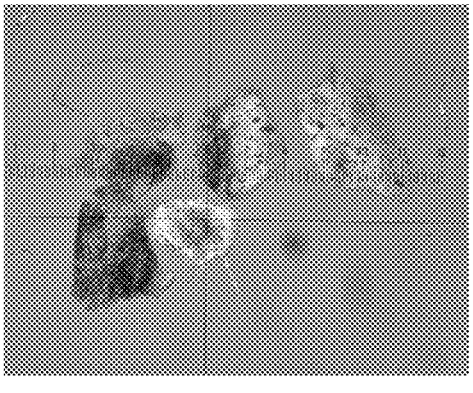

In one aspect, provided herein is a material comprising one or more water-soluble polysaccharides and one or more insoluble fibers, the ratio by weight between the total amount of the water-soluble polysaccharides and the total amount of the insoluble fibers is between about 1:1 and about 30:1; the water-soluble polysaccharides comprise (i) one or more gelling polysaccharides, (ii) one or more gelling-compatible polysaccharides, or (iii) both one or more gelling polysaccharides and one or more gelling-compatible polysaccharides; the one or more water-soluble polysaccharides and the one or more insoluble fibers form a superabsorbent material having a porous network structure without chemical cross-linking; the superabsorbent material has a volume expansion ratio of at least 10 times or up to 150 times in less than 2 hours; and when the superabsorbent material is hydrated (or rehydrated), the porous network structure comprises a plurality of pores with a two-dimensional pore density in a range of 1 per 100 micrometers squared ($\mu m^2$) to 500 per 100 micrometers squared ($\mu m^2$) and the pores have an average diameter size in the range of 1 micrometer ($\mu m$) to 30 micrometers ($\mu m$).

The one or more water-soluble polysaccharides in the superabsorbent material can be any, or any combination, of such polysaccharides provided in this Section (Detailed Description), the Section of "Summary," and the Section of "Examples." The one or more gelling polysaccharides in the superabsorbent material can be any, or any combination, of such gelling polysaccharides provided in this Section (Detailed Description), the Section of "Summary," and the Section of "Examples." The one or more gelling-compatible polysaccharides in the superabsorbent material can be any, or any combination, of such gelling-compatible polysaccharides provided in this Section (Detailed Description), the Section of "Summary," and the Section of "Examples." The ratio between the total amount of the water-soluble polysaccharides and the total amount of the insoluble fibers can be any such ratios provided in this Section (Detailed Description), the Section of "Summary," and the Section of "Examples." The one or more insoluble fibers in the superabsorbent material can be any, or any combination, of such fibers provided in this Section (Detailed Description), the Section of "Summary," and the Section of "Examples." The porous network structure can be any such structure provided in this Section (Detailed Description), the Section of "Summary," and the Section of "Examples." The pore density (including the average, variation, and range) can be any pore density for such superabsorbent material as provided in this Section (Detailed Description), the Section of "Summary," and the Section of "Examples." The pore diameter size (including the average, variation, and range) can be any pore diameter size for such superabsorbent material as provided in this Section (Detailed Description), the Section of "Summary," and the Section of "Examples." The volume expansion ratio (including the fold expansion and duration to achieve such fold expansion) can be any volume expansion ratio for such superabsorbent material as provided in this Section (Detailed Description), the Section of "Summary," and the Section of "Examples."

In another aspect, provided herein is a material comprising one or more water-soluble polysaccharides and one or more insoluble fibers, wherein the one or more water-soluble polysaccharides and the one or more insoluble fibers form a superabsorbent material having a porous network structure; wherein the water-soluble polysaccharides comprise (i) one or more gelling polysaccharides, (ii) one or more gelling-compatible polysaccharides, or (iii) both one or more gelling polysaccharides and one or more gelling-compatible polysaccharides; wherein the ratio between the total amount of the water-soluble polysaccharides and the total amount of the insoluble fibers is between about 1:1 and about 30:1; wherein when the superabsorbent material is hydrated or rehydrated, the porous network structure comprises a plurality of pores densely-populated, wherein the porous network structure has a two-dimensional pore density in a range of 1 per 100 $\mu m^2$ to 500 per 100 $\mu m^2$ and the pores have an average diameter size in the range of 1 $\mu m$ to 30 $\mu m$; and wherein the superabsorbent material has a volume expansion ratio of at least 10 times or up to 150 times in less than 2 hours.

The disclosure provides that the chemical cross-linking and physical cross-linking are two distinctive process. Chemical cross-linking refers to the cross-linking formed by additional bonds within the material. Chemical cross-linking can be a reaction of the ingredients in the material or a reaction induced by addition of chemical cross-linking reagents known and used in the art. In one embodiment of the various superabsorbent materials provided herein, the superabsorbent material comprise no chemical cross-linking reagent. In another embodiment of the various superabsorbent materials provided herein, the superabsorbent material has a porous network structure without chemical cross-linking. Physical cross-linking refers to cross-linking by the materials forming structures crossing or intertwining with each other such that the materials are linked as a result. For example, a gel can have a physically cross-linked structure if the fibers in the gel are cross and/or intertwine with each other to form a network structure. In one embodiment of the various superabsorbent materials provided herein, the superabsorbent material has a porous network structure formed by physical-linking.

Disclosed herein is a superabsorbent material comprising about 15% (w/w) to about 85% (w/w) of one or more water-soluble polysaccharides (such as gelling polysaccharides, gelling-compatible polysaccharides, or both gelling polysaccharides and gelling-compatible polysaccharides), and about 15% (w/w) to about 85% (w/w) of one or more insoluble fibers including, for example, insoluble dietary fibers. In some embodiments, the total insoluble fibers in the superabsorbent material is about 15% (w/w), about 20% (w/w), about 25% (w/w), about 30% (w/w), about 35% (w/w), about 40% (w/w), about 45% (w/w), about 50% (w/w), about 55% (w/w), about 60% (w/w), about 65% (w/w), about 70% (w/w), about 75% (w/w), about 80% (w/w), or about 85% (w/w). In some embodiments, the total soluble polysaccharides in the superabsorbent material is about 15% (w/w), about 20% (w/w), about 25% (w/w), about 30% (w/w), about 35% (w/w), about 40% (w/w), about 45% (w/w), about 50% (w/w), about 55% (w/w), about 60% (w/w), about 65% (w/w), about 70% (w/w), about 75% (w/w), about 80% (w/w), or about 85% (w/w). In other embodiments, the total gelling polysaccharides in the superabsorbent material is about 15% (w/w), about 20% (w/w), about 25% (w/w), about 30% (w/w), about 35% (w/w), about 40% (w/w), about 45% (w/w), about 50% (w/w), about 55% (w/w), about 60% (w/w), about 65% (w/w), about 70% (w/w), about 75% (w/w), about 80% (w/w), or about 85% (w/w). In further embodiments, the total gelling-compatible polysaccharides in the superabsorbent material is about 15% (w/w), about 20% (w/w), about 25% (w/w), about 30% (w/w), about 35% (w/w), about 40% (w/w), about 45% (w/w), about 50% (w/w), about 55% (w/w), about 60% (w/w), about 65% (w/w), about 70% (w/w), about 75% (w/w), about 80% (w/w), or about 85% (w/w). In additional embodiments, the total gelling polysaccharides and gelling-compatible polysaccharides in the superabsorbent material is about 15% (w/w), about 20% (w/w), about 25% (w/w), about 30% (w/w), about 35% (w/w), about 40% (w/w), about 45% (w/w), about 50% (w/w), about 55% (w/w), about 60% (w/w), about 65% (w/w), about 70% (w/w), about 75% (w/w), about 80% (w/w), or about 85% (w/w).

In some embodiments, the ratio between the total soluble polysaccharides (such as gelling polysaccharides, gelling-compatible polysaccharides, or both gelling polysaccharides and gelling-compatible polysaccharides), to the total insoluble fibers in the superabsorbent material is about 1:1, about 2:1, about 3:1, about 4:1, about 5:1, about 6:1, about 7:1, about 8:1, about 9:1, about 10:1, about 11:1, about 12:1, about 13:1, about 14:1, about 15:1, about 16:1, about 17:1, about 18:1, about 19:1, about 20:1, about 21:1, about 22:1, about 23:1, about 24:1, about 25:1, about 26:1, about 27:1, about 28:1, about 29:1, or about 30:1, such that the obtained superabsorbent material retains the ability to form a gel upon hydration or rehydration. In some embodiments, the ratio between (i) the total gelling polysaccharides, the gelling-compatible polysaccharides, or the combination thereof, to (ii) the total insoluble fiber in the superabsorbent material is about 1:1, about 2:1, about 3:1, about 4:1, about 5:1, about 6:1, about 7:1, about 8:1, about 9:1, about 10:1, about 11:1, about 12:1, about 13:1, about 14:1, about 15:1, about 16:1, about 17:1, about 18:1, about 19:1, about 20:1, about 21:1, about 22:1, about 23:1, about 24:1, about 25:1, about 26:1, about 27:1, about 28:1, about 29:1, or about 30:1, such that the obtained superabsorbent material retains the ability to form a gel upon hydration or rehydration. In other embodiments, the ratio between the total gelling polysaccharides to the total insoluble fiber in the superabsorbent material is about 1:1, about 2:1, about 3:1, about 4:1, about 5:1, about 6:1, about 7:1, about 8:1, about 9:1, about 10:1, about 11:1, about 12:1, about 13:1, about 14:1, about 15:1, about 16:1, about 17:1, about 18:1, about 19:1, about 20:1, about 21:1, about 22:1, about 23:1, about 24:1, about 25:1, about 26:1, about 27:1, about 28:1, about 29:1, or about 30:1, such that the obtained superabsorbent material retains the ability to form a gel upon hydration or rehydration. In further embodiments, the ratio between the total gelling-compatible polysaccharides to the total insoluble fiber in the superabsorbent material is about 1:1, about 2:1, about 3:1, about 4:1, about 5:1, about 6:1, about 7:1, about 8:1, about 9:1, about 10:1, about 11:1, about 12:1, about 13:1, about 14:1, about 15:1, about 16:1, about 17:1, about 18:1, about 19:1, about 20:1, about 21:1, about 22:1, about 23:1, about 24:1, about 25:1, about 26:1, about 27:1, about 28:1, about 29:1, or about 30:1, such that the obtained superabsorbent material retains the ability to form a gel upon hydration or rehydration.

In some embodiments, the water-soluble polysaccharides disclosed herein do not contain synthetic polymers or chemically-modified polymers. In some embodiments, the water-soluble polysaccharides include but are not limited to agar, carrageenan, gums such as konjac gum, locust bean gum, xanthan gum, gellan gum, Arabic gum, tamarind seed gum, guar gum, okara, alginate (such as sodium alginate), pectin, β-glucan, chitosan, galactomannans, glucomannans, and a soluble starch or a soluble dietary fiber such as Psyllium fiber. In some embodiments, the water-soluble polysaccharide is a gelling polysaccharide, including, but not limited to, carrageen (e.g. k-carrageenan), konjac gum, psyllium husk, alginate, pectin, gellan, chitosan, and curdlan. In other embodiments, the water-soluble polysaccharide is a gelling-compatible polysaccharide, including, but not limited to, xanthan gum, locust bean gum, guar gum, tamarind seed gum, okara, and gum acacia. In some embodiments, the insoluble dietary fibers include but are not limited to insoluble fiber in soybean fiber, insoluble fiber from seaweeds (such as Rhodophyta, Phaeophyta, Chlorophyta), seaweed composite materials, cellulose, insoluble hemicellulose, lignin of seeds, seed skins, roots, stems, leaves, barks from legume, wheat bran, whole grain, vegetables, fruits, beans, seeds, seed skins, oat fiber, rice fiber, oak fiber, corn fiber, citrus fiber, beet fiber, sugarcane fiber, coconut fiber, and compositions comprising a combination of said insoluble fibers.

As is known and practiced in the field, a gelling polysaccharide can be confirmed as such by any one of a number of assays, for example as described in Tanja Wüstenberg, Cellulose and Cellulose Derivatives in the Food Industry: Fundamentals and Applications, First Edition, Chapter 1 and Masakuni Tako, Advances in Bioscience and Biotechnology, 6: 22-36 (2015), both of which are herein incorporated in their entirety by reference. In some embodiment, a gelling polysaccharide can be confirmed as such by solubilizing in water with or without heating, cooling down to a suitable gelling temperature, and determining if the solution of the gelling polysaccharide forms a gel.

Alternatively, in another embodiment, a gelling polysaccharide can be confirmed by rheology, for example as described in G.I.T. Laboratory Journal 3-4/2007, pp 68-70. Briefly, small amplitude oscillatory sweep can be conducted to determine G' (storage modules, Pa) and G" (loss modules, Pa) with respect to time, temperature, frequency, stress, and/or strain. If G' is greater than G" for the solution of the polysaccharide after solubilization and cooling as described in the preceding paragraph (hydrated polysaccharide), then the hydrated polysaccharide has a solid-like gel texture and such polysaccharide is a gelling polysaccharide.

Similarly and as is known and practiced in the field, a gelling compatible polysaccharide can be confirmed as such by any one of a number of assays, for example as described in Tanja Wüstenberg, Cellulose and Cellulose Derivatives in the Food Industry: Fundamentals and Applications, First Edition, Chapter 1 and Masakuni Tako, Advances in Bioscience and Biotechnology, 6: 22-36 (2015), both of which are herein incorporated in their entirety by reference. In some embodiment, a gelling compatible polysaccharide can be confirmed as such by solubilizing along with other polysaccharide(s) in water with or without heating, cooling down to a suitable gelling temperature, and determining if the solution can form a gel due to the synergistic interaction between the gelling compatible polysaccharides which would otherwise not be able to form a gel under the tested condition.

Alternatively, in another embodiment, a gelling polysaccharide can be confirmed by rheology, for example as described in G.I.T. Laboratory Journal 3-4/2007, pp 68-70. Briefly, small amplitude oscillatory sweep can be conducted to determine G' (storage modules, Pa) and G" (loss modules, Pa) with respect to time, temperature, frequency, and/or stress. If G' is greater than G" for the solution of the polysaccharide after solubilization and cooling as described in the preceding paragraph (hydrated polysaccharide), then the hydrated polysaccharide has a solid-like gel texture and such polysaccharide is a gelling-compatible polysaccharide As is well known in the field, gelling polysaccharides and gelling compatible polysaccharides are not mutually exclusive. Some gelling polysaccharides can also be gelling compatible polysaccharides, as these gelling polysaccharides can form gels by themselves as known in the field and confirmable by the assays described above and these gelling polysaccharides can also form a gel when combined with another polysaccharide due to synergies between such polysaccharides. Such polysaccharides include agar, carrageenan, konjac gum, pectin, alginate, and curdlan. Some gelling compatible polysaccharides, on the other hand, are not gelling polysaccharides as they can form a gel when combined with another polysaccharide due to synergies between such polysaccharides but they cannot form gels by themselves, which can be determined by the assay described above. Such gelling compatible polysaccharides include xanthan gum, guar gum, gum acacia, tamarind seed gum, okara, and locust bean gum.

In certain embodiments, the superabsorbent material disclosed herein is made from a soybean dietary fiber composition disclosed and made by a process as disclosed herein and as disclosed in PCT Application No. PCT/US2021/014388, filed on Jan. 21, 2021 (which is incorporated herein in its entirety by reference), a seaweed composite material comprising one or more insoluble fibers and agar disclosed and made by a process as disclosed herein and as disclosed in PCT Application No. PCT/US2020/070160, filed on Jun. 19, 2020 and published as WO2020/257825 on Dec. 24, 2020 (which is herein incorporated in its entirety by reference), a seaweed composite material comprising one or more insoluble fibers and carrageenan disclosed and made by a process as disclosed herein and as disclosed in PCT Application No. PCT/US2020/070161, filed on Jun. 19, 2020 and published as WO2020/257826 on Dec. 24, 2020 (which is herein incorporated in its entirety by reference), or a combination thereof.

Both soluble and insoluble dietary fibers can promote human health. It has been increasingly recognized that excessive intake of high calorie carbohydrate food (e.g. flour and rice or any food rich in digestible starch) can lead to a wide range of health problems including obesity and diabetes. The superabsorbent composite materials comprising naturally abundant source of soluble and insoluble dietary fibers disclosed herein can be used in traditional food to limit the intake of food carbohydrate. Soluble dietary fiber (SDF) has prebiotic activity and can reduce cholesterol level and improve glucose control in diabetes. Further studies suggest that SDF has anti-inflammatory, anti-oxidative and anticarcinogenic effects and many other potential health benefits. The insoluble dietary fiber (IDF) is known to have laxative function and can help improve gastrointestinal health (e.g., preventing diarrhea, constipation, diverticulitis and hemorrhoids). Given the health benefits, it is important to develop superabsorbent materials that contain insoluble dietary fibers. Moreover, including insoluble dietary fibers also provides new functional properties to the superabsorbent materials such as unique absorption functions towards different molecules, swelling capabilities, structure stabilities under different solution and physiological conditions.

An important aspect of developing composite superabsorbent materials disclosed herein is to find an optimized ingredient mixture of polysaccharides, such as gelling polysaccharides and gelling-compatible polysaccharides, and insoluble dietary fibers at an optimized ratio, and variable processing conditions to produce the disclosed composite superabsorbent materials having a certain structure resulting in a high water absorption and volume expansion capabilities at room temperature. The composite superabsorbent materials disclosed herein can quickly expand in volume and maintain its expanded shape and for the individual ingredients to remain in a non-aggregated state upon hydration or rehydration. Some contemplated embodiments for the ratio between the total water-soluble polysaccharide to total insoluble fiber in the superabsorbent material are described herein, e.g. in the "Summary" Section, this Section ("Detailed Description"), and the "Example" Section. Additionally, certain contemplated embodiments for the ratio between (i) the total gelling polysaccharides, the total gelling-compatible polysaccharides, or the combination thereof, to (ii) the total insoluble fiber are also are also described herein, e.g. in the "Summary" Section, this Section ("Detailed Description"), and the "Example" Section.

Certain types of polysaccharides, such as gelling polysaccharides and gelling-compatible polysaccharides, have synergistic effects in solution and in gelling process. For example, synergistic effects are observed between carrageenan and locust bean gum, or between xanthan gum and locust bean gum, such that the systemic viscosity of the mixed solution is greater than the sum of each component in this system, or the mixture will result in a higher strength gel than each individual component. Mutual synergistic effects among locust bean gum, xanthan gum, agar or carrageenan are also observed which can improve the gel strength and structure of composite gel. However, the synergistic effect is dependent upon the specific mixture of polysaccharides, for example, the mixture of carrageenan and guar gum has no synergistic effect.

Further, it is important to enhance the structural stability of the composite superabsorbent materials to obtain a highly stable structure having a porous network structure for superior water absorption, volume expansion, structure stability, and/or shape stability and non-aggregating features. Many conventional superabsorbent materials achieve a desirable stability via the use of an exogenous force, such as modified or synthetic polymers or chemical crosslinking, air pumping, yeast fermentation, chemical reaction, by enzyme digestion of the material and diffuse out the enzyme digested fragments, which are highly undesirable in food and health supplement applications, and cumbersome and costly to remove. Thus, the superabsorbent material disclosed herein is neither expanded with a gas nor digested with an enzyme prior to or during the formation of the superabsorbent material. In certain embodiments, the superabsorbent material provided herein has a porous network structure without chemical cross-linking. In one embodiment, the superabsorbent material disclosed herein is not expanded with a gas prior to or during the formation of the superabsorbent material. In another embodiment, the superabsorbent material disclosed herein is not digested with an enzyme prior to or during the formation of the superabsorbent material. In a further embodiment, the superabsorbent material disclosed herein is not subjected to yeast fermentation prior to or during the formation of the superabsorbent material. In yet another embodiment, the superabsorbent material disclosed herein is not subjected to chemical reaction prior to or during the formation of the superabsorbent material. In an additional embodiment, the superabsorbent material disclosed herein is not subjected to chemical crosslinking prior to or during the formation of the superabsorbent material. As such, in some embodiments, the disclosure provides that the superabsorbent material provided herein is not subjected to any or any combination of the conventional means described in this paragraph.

The structural stability of the disclosed composite superabsorbent materials can be enhanced by freezing treatment of the gel. Physically crosslinked hydrogels can be formed by a freeze-thaw technique, also known as cryo-gelation or cryo-structuring. When a solution of a polymer or a mixture of different polymers is frozen, the water becomes ice and phase-separated from the polymer molecules. As a result, the polymer molecules are forced to interact with each other. A multi-cycle of freeze and thaw process can be used to induce gel formation thereby to form a variety of cryogels. The inventor(s) unexpectedly discovered that the composite superabsorbent materials comprising one or more soluble polysaccharides, such as gelling polysaccharides and gelling-compatible polysaccharides, and one or more insoluble dietary fibers have an increased stability when processed at freezing temperature for an extended period of time, such as at least 24 hours, 48 hours, 72 hours, 96 hours, 120 hours, or more. such that the superabsorbent materials form a stable porous network structure. Although not wish to be bound by theory, the formation of the stable porous network structure is probably due to increased interactions between the soluble polysaccharides, such as gelling polysaccharides and gelling-compatible polysaccharides, and insoluble dietary fibers during the freeze and thaw cycles. Thus, the disclosed superabsorbent materials can quickly absorb a large amount of liquid upon hydration or rehydration with water or gastric liquid at room temperature or body temperature, and quickly swell in volume and maintain its expanded shape and for the individual ingredients to be in a non-aggregate state in an aqueous solution.

In one specific embodiment, the superabsorbent material disclosed herein maintains a well-defined structure, as characterized by a gel strength of at least 50 g, for at least 12 hours under a neutral pH condition or a human gastric pH condition. In some embodiments, the superabsorbent material disclosed herein maintains a well-defined structure, as characterized by a gel strength of at least 50 g, for at least 24 hours under a neutral pH condition or a human gastric pH condition. In another embodiment, the superabsorbent material disclosed herein maintains a well-defined structure, as characterized by a gel strength of at least 50 g, for at least 36 hours under a neutral pH condition or a human gastric pH condition. In a further embodiment, the superabsorbent material disclosed herein maintains a well-defined structure, as characterized by a gel strength of at least 50 g, for at least 48 hours under a neutral pH condition or a human gastric pH condition. In yet another embodiment, the superabsorbent material disclosed herein maintains a well-defined structure, as characterized by a gel strength of at least 50 g, for at least 60 hours under a neutral pH condition or a human gastric pH condition. In an additional embodiment, the superabsorbent material disclosed herein maintains a well-defined structure, as characterized by a gel strength of at least 50 g, for at least 72 hours under a neutral pH condition or a human gastric pH condition. In one embodiment, the superabsorbent material disclosed herein maintains a well-defined structure, as characterized by a gel strength of at least 50 g, for at least 84 hours under a neutral pH condition or a human gastric pH condition. In an additional embodiment, the superabsorbent material disclosed herein maintains a well-defined structure, as characterized by a gel strength of at least 50 g, for at least 96 hours under a neutral pH condition or a human gastric pH condition. In other embodiments, the maintenance of a well-defined structure can be characterized by a gel strength of at least 25 g, at least 50 g, at least 75 g, at least 100 g, at least 125 g, at least 150 g, at least 175 g, at least 200 g, at least 225 g, at least 250 g, at least 275 g, at least 300 g, at least 325 g, at least 350 g, at least 375 g, at least 400 g, at least 425 g, at least 450 g, at least 475 g, at least 500 g, or more, for any duration under a neutral pH condition or a human gastric pH condition as described in this paragraph. In some further embodiments, the maintenance of a well-defined structure can be characterized by a gel strength of about 25 g, about 50 g, about 75 g, about 100 g, about 125 g, about 150 g, about 175 g, about 200 g, about 225 g, about 250 g, about 275 g, about 300 g, about 325 g, about 350 g, about 375 g, about 400 g, about 425 g, about 450 g, about 475 g, about 500 g, or more, for any duration under a neutral pH condition or a human gastric pH condition as described in this paragraph.

In one specific embodiment, the superabsorbent material disclosed herein maintains a well-defined structure, as characterized by a storage modulus (G') of $10^3$ to $10^6$ Pa, for at least 12 hours under a neutral pH condition or a human gastric pH condition. In some embodiments, the superabsorbent material disclosed herein maintains a well-defined structure, as characterized by a storage modulus (G') of $10^3$ to $10^6$ Pa, for at least 24 hours under a neutral pH condition or a human gastric pH condition. In another embodiment, the superabsorbent material disclosed herein maintains a well-defined structure, as characterized by a storage modulus (G') of $10^3$ to $10^6$ Pa, for at least 36 hours under a neutral pH condition or a human gastric pH condition. In a further embodiment, the superabsorbent material disclosed herein maintains a well-defined structure, as characterized by a storage modulus (G') of $10^3$ to $10^6$ Pa, for at least 48 hours under a neutral pH condition or a human gastric pH condition. In yet another embodiment, the superabsorbent material disclosed herein maintains a well-defined structure, as characterized by a storage modulus (G') of $10^3$ to $10^6$ Pa, for at least 60 hours under a neutral pH condition or a human gastric pH condition. In an additional embodiment, the superabsorbent material disclosed herein maintains a well-defined structure, as characterized by a storage modulus (G') of $10^3$ to $10^6$ Pa, for at least 72 hours under a neutral pH condition or a human gastric pH condition. In one embodiment, the superabsorbent material disclosed herein maintains a well-defined structure, as characterized by a storage modulus (G') of $10^3$ to $10^6$ Pa, for at least 84 hours under a neutral pH condition or a human gastric pH condition. In an additional embodiment, the superabsorbent material disclosed herein maintains a well-defined structure, as characterized by a storage modulus (G') of $10^3$ to $10^6$ Pa, for at least 96 hours under a neutral pH condition or a human gastric pH condition. In other embodiments, the maintenance of a well-defined structure can be characterized by maintaining a storage modulus (G') of at least $10^3$ Pa, at least $1.5 \times 10^3$ Pa, at least $2 \times 10^3$ Pa, at least $2.5 \times 10^3$ Pa, at least $3 \times 10^3$ Pa, at least $3.5 \times 10^3$ Pa, at least $4 \times 10^3$ Pa, at least $4.5 \times 10^3$ Pa, at least $5 \times 10^3$ Pa, at least $5.5 \times 10^3$ Pa, at least $6 \times 10^3$ Pa, at least $6.5 \times 10^3$ Pa, at least $7 \times 10^3$ Pa, at least $7.5 \times 10^3$ Pa, at least $8 \times 10^3$ Pa, at least $8.5 \times 10^3$ Pa, at least $9 \times 10^3$ Pa, at least $9.5 \times 10^3$ Pa, at least $10^4$ Pa, at least $1.5 \times 10^4$ Pa, at least $2 \times 10^4$ Pa, at least $2.5 \times 10^4$ Pa, at least $3 \times 10^4$ Pa, at least $3.5 \times 10^4$ Pa, at least $4 \times 10^4$ Pa, at least $4.5 \times 10^4$ Pa, at least $5 \times 10^4$ Pa, at least $5.5 \times 10^4$ Pa, at least $6 \times 10^4$ Pa, at least $6.5 \times 10^4$ Pa, at least $7 \times 10^4$ Pa, at least $7.5 \times 10^4$ Pa, at least $8 \times 10^4$ Pa, at least $8.5 \times 10^4$ Pa, at least $9 \times 10^4$ Pa, at least $9.5 \times 10^4$ Pa, or at least $10^5$ Pa, for any duration under a neutral pH condition or a human gastric pH condition as described in this paragraph. In some further embodiments, the maintenance of a well-defined structure can be characterized by maintaining a storage modulus (G') of about $10^3$ Pa, about $1.5 \times 10^3$ Pa, about $2 \times 10^3$ Pa, about $2.5 \times 10^3$ Pa, about $3 \times 10^3$ Pa, about $3.5 \times 10^3$ Pa, about $4 \times 10^3$ Pa, about $4.5 \times 10^3$ Pa, about $5 \times 10^3$ Pa, about $5.5 \times 10^3$ Pa, about $6 \times 10^3$ Pa, about $6.5 \times 10^3$ Pa, about $7 \times 10^3$ Pa, about $7.5 \times 10^3$ Pa, about $8 \times 10^3$ Pa, about $8.5 \times 10^3$ Pa, about $9 \times 10^3$ Pa, about $9.5 \times 10^3$ Pa, about $10^4$ Pa, about $1.5 \times 10^4$ Pa, about $2 \times 10^4$ Pa, about $2.5 \times 10^4$ Pa, about $3 \times 10^4$ Pa, about $3.5 \times 10^4$ Pa, about $4 \times 10^4$ Pa, about $4.5 \times 10^4$ Pa, about $5 \times 10^4$ Pa, about $5.5 \times 10^4$ Pa, about $6 \times 10^4$ Pa, about $6.5 \times 10^4$ Pa, about $7 \times 10^4$ Pa, about $7.5 \times 10^4$ Pa, about $8 \times 10^4$ Pa, about $8.5 \times 10^4$ Pa, about $9 \times 10^4$ Pa, about $9.5 \times 10^4$ Pa, or about $10^5$ Pa, for any duration under a neutral pH condition or a human gastric pH condition as described in this paragraph.

In some embodiments, the superabsorbent material provided herein can expand its volume rapidly in less than 5 hours, less than 4 hours less than 3 hours less than 2 hours, less than 1.5 hours, less than 1 hour, less than 30 minutes, less than 25 minutes, or less than 15 minutes and maintain a well-defined structure as characterized in the preceding paragraphs and the paragraphs in this Section (Detailed Description), the Section of "Summary," and the Section of "Examples." In other embodiments, the superabsorbent material provided herein can expand its volume rapidly in about 5 hours, about 4 hours about 3 hours about 2 hours, about 1.5 hours, about 1 hour, about 30 minutes, about 25 minutes, or about 15 minutes and maintain a well-defined structure as characterized in the preceding paragraphs and the paragraphs in this Section (Detailed Description), the Section of "Summary," and the Section of "Examples."

In certain embodiments, the superabsorbent material disclosed herein has an extended porous structure characterized by highly organized and inter-connected pores.

The porous network structure can be characterized by the porosity, which is the ratio between the void space (empty space or the space of the pores) in a material to the total volume. The matrix of the porous network structure or the matrix of the superabsorbent material refers to the matters making up the volume that is not the void space (empty space or the space of the pores) of the superabsorbent material. The porous network structure includes the pores, the matrix, and the spatial distribution, pattern, and arrangement of the pores and the matrix.

The superabsorbent material can be prepared according to the methods disclosed herein, which produces a superabsorbent material in its dried state (e.g. after freeze-drying, or after vacuum freeze-drying). In its dried state, the superabsorbent material has a dense, highly-packed porous network structure. For example, in certain embodiments, the dense, highly-packed porous network structure makes up at least 50%, at least 55%, at least 60%, at least 65%, at least 70%, at least 75%, at least 80%, at least 85%, at least 90%, or at least 95% volume of the dried superabsorbent material. In some embodiments of the dried superabsorbent material, the porous network structure has a porosity of 30% to 95%, or any range subsumed therein, including but not limited to 40% to 80%, 40% to 90%, 60% to 80%, 50% to 90%, 50% to 70%, 60% to 90%, and 70% to 90%. In some embodiments, the superabsorbent material is in a substantially dried state.

When the superabsorbent material is hydrated or rehydrated, the superabsorbent material has a highly porous network structure. In certain embodiments, the hydrated or rehydrated superabsorbent material has a highly porous network structure. For example, at least 50%, at least 55%, at least 60%, at least 65%, at least 70%, at least 75%, at least 80%, at least 85%, at least 90%, or at least 95% volume of the superabsorbent material forms a highly porous network structure.

In the various embodiments of the superabsorbent material provided herein, the soluble polysaccharides and insoluble fibers in the superabsorbent materials can expand concertedly such that the insoluble fibers expand and disperse evenly when the superabsorbent material absorbs water and expand in volume. When hydrated or rehydrated, the insoluble fibers are evenly distributed in the gel matrix without the need of additional energy (e.g., homogenization, or high shear mixing). As such, in one embodiment, the superabsorbent material can form a gel upon hydration or rehydration without homogenizing the insoluble fibers. In another embodiment, the superabsorbent material can form a gel upon hydration or rehydration without mechanically dispersing the insoluble fibers. In a further embodiment, the superabsorbent material can form a gel upon hydration or rehydration without mixing the insoluble fibers. In yet another embodiment, the superabsorbent material can form a gel upon hydration or rehydration without mixing the insoluble fibers with high shear. In yet a further embodiment, the superabsorbent material can form a gel upon hydration or rehydration without heating the insoluble fibers. In one embodiment, the superabsorbent material can form a gel upon hydration or rehydration without actively distributing or dispersing insoluble fibers by any means.

In the various embodiments of the superabsorbent material provided herein, the insoluble fibers in the superabsorbent materials are evenly distributed in the superabsorbent material when the superabsorbent material is hydrated or rehydrated. Such even distribution of the insoluble fibers in the superabsorbent material can be characterized by that the densities of the insoluble fibers in the superabsorbent materials are similar or comparable from one subarea or subvolume of the superabsorbent material to another subarea or subvolume of the superabsorbent material. In some embodiments, the even distribution of the insoluble fibers in the superabsorbent material can be characterized by the coefficient of variation of the densities of the insoluble fibers for a plurality of 1 millimeter cubed ($mm^3$) subvolumes of the same superabsorbent material being less than 1. In certain embodiments, the even distribution of the insoluble fibers in the superabsorbent material can be characterized by the coefficient of variation of the densities of the insoluble fibers for a plurality of 1 $mm^3$ subvolumes of the same superabsorbent material being less than 2, less than 1.9, less than 1.8, less than 1.7, less than 1.6, less than 1.5, less than 1.4, less than 1.3, less than 1.2, or less than 1.1, less than 1, less than 0.9, less than 0.8, less than 0.7, less than 0.6, less than 0.5, less than 0.4, less than 0.3, less than 0.2, or less than 0.1. In some additional embodiments, the even distribution of the insoluble fibers in the superabsorbent material can be characterized by the coefficient of variation of the densities of the insoluble fibers for a plurality of 1 $mm^3$ subvolumes of the same superabsorbent material being about 2, about 1.9, about 1.8, about 1.7, about 1.6, about 1.5, about 1.4, about 1.3, about 1.2, or about 1.1, about 1, about 0.9, about 0.8, about 0.7, about 0.6, about 0.5, about 0.4, about 0.3, about 0.2, or about 0.1. In other embodiments, the even distribution of the insoluble fibers in the superabsorbent material can be characterized by that the densities of the insoluble fibers for a plurality of 1 $mm^3$ subvolumes of the same superabsorbent material vary by less than 50%, less than 40%, less than 30%, less than 20%, or less than 10%. In some further embodiments, the even distribution of the insoluble fibers in the superabsorbent material can be characterized by that the densities of the insoluble fibers for a plurality of 1 $mm^3$ subvolumes of the same superabsorbent material vary by about 50%, about 40%, about 30%, about 20%, or about 10%. In some additional embodiments of the superabsorbent materials provided in this paragraph, the subvolumes used for determining the density could be a subvolume of 0.1 $mm^3$, 0.2 $mm^3$, 0.3 $mm^3$, 0.4 $mm^3$, 0.5 $mm^3$, 0.6 $mm^3$, 0.7 $mm^3$, 0.8 $mm^3$, 0.9 $mm^3$, 1 $mm^3$, 5 $mm^3$, 10 $mm^3$, 25 $mm^3$, 50 $mm^3$, 100 $mm^3$, 500 $mm^3$, or 1000 $mm^3$. In other embodiments of the superabsorbent materials provided in this paragraph, the densities can be determined and compared across subareas of the same superabsorbent material and subareas used for determining the density could be a subarea of 0.01 $mm^2$, 0.02 $mm^2$, 0.03 $mm^2$, 0.04 $mm^2$, 0.05 $mm^2$, 0.06 $mm^2$, 0.07 $mm^2$, 0.08 $mm^2$, 0.09 $mm^2$, 0.1 $mm^2$, 0.2 $mm^2$, 0.3 $mm^2$, 0.4 $mm^2$, 0.5 $mm^2$, 0.6 $mm^2$, 0.7 $mm^2$, 0.8 $mm^2$, 0.9 $mm^2$, 1 $mm^2$, 5 $mm^2$, 10 $mm^2$, 25 $mm^2$, 50 $mm^2$, or 100 $mm^2$. In certain embodiments of the superabsorbent materials provided in this paragraph, the densities can be determined and compared across 3, 4, 5, 6, 7, 8, 9, 10, 11, 12, 13, 14, 15, 16, 17, 18, 19, or 20 such subareas or subvolumes.

Accordingly, in one specific embodiment, the superabsorbent material upon hydration or rehydration can form a gel with insoluble fibers evenly distributed in matrix without homogenizing. As is clear from the descriptions, such even distribution of in soluble fibers in the superabsorbent material can be characterized as described in the preceding few paragraphs.

When the superabsorbent material is hydrated or rehydrated, the porous network structure is characterized by a plurality of pores densely-populated and organized in a highly uniform pattern. The structure of the superabsorbent material can be characterized by pore density, pore diameter size, variation of the pore density, and/or variation of the pore diameter size. Additionally, the structure of the superabsorbent material can also be characterized by the similarity of the porous network structure from one subarea or subvolume of superabsorbent material to another subarea or subvolume of superabsorbent material, including the similarities in pore density, pore diameter size, and the porous network structure itself.

Accordingly, in some embodiments, when the superabsorbent material is hydrated or rehydrated, the porous network structure is characterized by a two-dimensional pore density in a range of 1 per 100 $\mu m^2$ to 500 per 100 $\mu m^2$, or any range subsumed therein. In certain embodiments, when the superabsorbent material is hydrated or rehydrated, the porous network structure is characterized by a two-dimensional pore density in a range of 10 per 100 $\mu m^2$ to 450 per 100 $\mu m^2$. In one embodiment, when the superabsorbent material is hydrated or rehydrated, the porous network structure is characterized by a two-dimensional pore density in a range of 20 per 100 $\mu m^2$ to 400 per 100 $\mu m^2$. In another embodiment, when the superabsorbent material is hydrated or rehydrated, the porous network structure is characterized by a two-dimensional pore density in a range of 30 per 100 $\mu m^2$ to 350 per 100 $\mu m^2$. In a further embodiment, when the superabsorbent material is hydrated or rehydrated, the porous network structure is characterized by a two-dimensional pore density in a range of 40 per 100 $\mu m^2$ to 300 per 100 $\mu m^2$. In yet another embodiment, when the superabsorbent material is hydrated or rehydrated, the porous network structure is characterized by a two-dimensional pore density in a range of 50 per 100 $\mu m^2$ to 250 per 100 $\mu m^2$. In one embodiment, when the superabsorbent material is hydrated or rehydrated, the porous network structure is characterized by a two-dimensional pore density in a range of 60 per 100 $\mu m^2$ to 200 per 100 $\mu m^2$. In another embodiment, when the superabsorbent material is hydrated or rehydrated, the porous network structure is characterized by a two-dimensional pore density in a range of 70 per 100 $\mu m^2$ to 150 per 100 $\mu m^2$. In another embodiment, when the superabsorbent material is hydrated or rehydrated, the porous network structure is characterized by a two-dimensional pore density in a range of 80 per 100 $\mu m^2$ to 100 per 100 $\mu m^2$. In some embodiments, when the superabsorbent material is hydrated or rehydrated, the porous network structure is characterized by a two-dimensional pore density of about 10, about 20, about 30, about 40, about 50, about 60, about 70, about 80, about 90, about 100, about 110, about 120, about 130, about 140, about 150, about 160, about 170, about 180, about 190, about 200, about 210, about 220, about 230, about 240, about 250, about 260, about 270, about 280, about 290, about 300, about 310, about 320, about 330, about 340, about 350, about 360, about 370, about 380, about 390, about 400, about 410, about 420, about 430, about 440, about 450, about 460, about 470, about 480, about 490, about 500, or any range between any two numbers listed in this sentence, per 100 $\mu m^2$.

Alternatively and as described above, the structure of the superabsorbent material can also be characterized by the similarity of the pore density of the porous network structure from one subarea or subvolume of superabsorbent material to another subarea or subvolume of the superabsorbent material (similarity or uniformity of the pore density within the same superabsorbent material). In some embodiments, the similarity or uniformity of the pore density within the same superabsorbent material can be characterized by the coefficient of variation of the two-dimensional pore densities for a plurality of subareas of the same superabsorbent material being less than 1. In certain embodiments, the similarity or uniformity of the pore density within the same superabsorbent material can be characterized by the coefficient of variation of the two-dimensional pore densities for a plurality of 100 $\mu m^2$ subareas of the same superabsorbent material being less than 2, less than 1.9, less than 1.8, less than 1.7, less than 1.6, less than 1.5, less than 1.4, less than 1.3, less than 1.2, or less than 1.1, less than 1, less than 0.9, less than 0.8, less than 0.7, less than 0.6, less than 0.5, less than 0.4, less than 0.3, less than 0.2, or less than 0.1. In some additional embodiments, the similarity or uniformity of the pore density within the same superabsorbent material can be characterized by the coefficient of variation of the two-dimensional pore densities for a plurality of 100 $\mu m^2$ subareas of the same superabsorbent material being about 2, about 1.9, about 1.8, about 1.7, about 1.6, about 1.5, about 1.4, about 1.3, about 1.2, or about 1.1, about 1, about 0.9, about 0.8, about 0.7, about 0.6, about 0.5, about 0.4, about 0.3, about 0.2, about 0.1, or any range between any two numbers listed in this sentence. In other embodiments, the similarity or uniformity of the pore density within the same superabsorbent material can be characterized by that the two-dimensional pore densities for a plurality of 100 $\mu m^2$ subareas of the same superabsorbent material vary by less than 50%, less than 40%, less than 30%, less than 20%, less than 10%, or any range between any two numbers listed in this sentence. In some further embodiments, the similarity or uniformity of the pore density within the same superabsorbent material can be characterized by that the 2-dimensional pore densities for a plurality of 100 $\mu m^2$ subareas of the same superabsorbent material vary by about 50%, about 40%, about 30%, about 20%, about 10%, or any range between any two numbers listed in this sentence. In some additional embodiments of the superabsorbent materials provided in this paragraph, the subvolumes used for determining the pore density could be a subarea of 10 $\mu m^2$, 20 $\mu m^2$, 30 $\mu m^2$, 40 $\mu m^2$, 50 $\mu m^2$, 60 $\mu m^2$, 70 $\mu m^2$, 80 $\mu m^2$, 90 $\mu m^2$, 100 $\mu m^2$, 150 $\mu m^2$, 200 $\mu m^2$, 250 $\mu m^2$, 300 $\mu m^2$, 350 $\mu m^2$, 400 $\mu m^2$, 450 $\mu m^2$, or 500 $\mu m^2$. In other embodiments of the superabsorbent materials provided in this paragraph, the pore densities can be determined and compared across 3, 4, 5, 6, 7, 8, 9, 10, 11, 12, 13, 14, 15, 16, 17, 18, 19, or 20 such subareas.

Similarly, the structure of the superabsorbent material can be characterized by pore diameter size and/or variation of the pore diameter size. In certain embodiments of the superabsorbent material when the such material is hydrated or rehydrated, the pores of the porous network structure have an average diameter size in the range of 1 $\mu m$ to 30 $\mu m$, or any range subsumed therein, including but not limited to 1 $\mu m$ to 30 $\mu m$, 1 $\mu m$ to 25 $\mu m$, 1 $\mu m$ to 20 $\mu m$, 1 $\mu m$ to 15 $\mu m$, 1 $\mu m$ to 10 $\mu m$, 2 $\mu m$ to 30 $\mu m$, 2 $\mu m$ to 25 $\mu m$, 2 $\mu m$ to 20 $\mu m$, 2 $\mu m$ to 15 $\mu m$, 2 $\mu m$ to 10 $\mu m$, 3 $\mu m$ to 30 $\mu m$, 3 $\mu m$ to 25 $\mu m$, 3 $\mu m$ to 20 $\mu m$, 3 $\mu m$ to 15 $\mu m$, 3 $\mu m$ to 10 $\mu m$, 4 $\mu m$ to 30 $\mu m$, 4 $\mu m$ to 25 $\mu m$, 4 $\mu m$ to 20 $\mu m$, 4 $\mu m$ to 15 $\mu m$, 4 $\mu m$ to 10 $\mu m$, 5 $\mu m$ to 30 $\mu m$, 5 $\mu m$ to 25 $\mu m$, 5 $\mu m$ to 20 $\mu m$, 5 $\mu m$ to 15 $\mu m$, 5 $\mu m$ to 10 $\mu m$, 6 $\mu m$ to 30 $\mu m$, 6 $\mu m$ to 25 $\mu m$, 6 $\mu m$ to 20 $\mu m$, 6 $\mu m$ to 15 $\mu m$, 6 $\mu m$ to 10 $\mu m$, 7 $\mu m$ to 30 $\mu m$, 7 $\mu m$ to 25 $\mu m$, 7 $\mu m$ to 20 $\mu m$, 7 $\mu m$ to 15 µm, 7 µm to 10 µm, 8 µm to 30 µm, 8 µm to 25 µm, 8 µm to 20 µm, 8 µm to 15 µm, 8 µm to 10 µm, 9 µm to 30 µm, 9 µm to 25 µm, 9 µm to 20 µm, 9 µm to 15 µm, 9 µm to 10 µm, 10 µm to 30 µm, 10 µm to 25 µm, 10 µm to 15 µm, 10 µm to 15 µm, 15 µm to 30 µm, 15 µm to 25 µm, or 15 µm to 20 µm. In some embodiments, when the superabsorbent material is hydrated or rehydrated, the porous network structure is characterized by an average diameter size of about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50 µm, or any range between any two numbers listed in this sentence.

Alternatively and as described above, the structure of the superabsorbent material can also be characterized by the similarity of the pore diameter size of the porous network structure from one subarea or subvolume of superabsorbent material to another subarea or subvolume of the superabsorbent material (similarity or uniformity of the pore diameter size within the same superabsorbent material). In some embodiments, the similarity or uniformity of the pore diameter size within the same superabsorbent material can be characterized by the coefficient of variation of the average pore diameter sizes for a plurality of subareas of the same superabsorbent material being less than 1. In certain embodiments, the similarity or uniformity of the pore diameter size within the same superabsorbent material can be characterized by the coefficient of variation of the average pore diameter sizes for a plurality of 100 µm$^2$ subareas of the same superabsorbent material being less than 2, less than 1.9, less than 1.8, less than 1.7, less than 1.6, less than 1.5, less than 1.4, less than 1.3, less than 1.2, or less than 1.1, less than 1, less than 0.9, less than 0.8, less than 0.7, less than 0.6, less than 0.5, less than 0.4, less than 0.3, less than 0.2, or less than 0.1. In some additional embodiments, the similarity or uniformity of the pore diameter size within the same superabsorbent material can be characterized by the coefficient of variation of the average pore diameter sizes for a plurality of 100 µm$^2$ subareas of the same superabsorbent material being about 2, about 1.9, about 1.8, about 1.7, about 1.6, about 1.5, about 1.4, about 1.3, about 1.2, or about 1.1, about 1, about 0.9, about 0.8, about 0.7, about 0.6, about 0.5, about 0.4, about 0.3, about 0.2, about 0.1, or any range between any two numbers listed in this sentence. In other embodiments, the similarity or uniformity of the pore diameter size within the same superabsorbent material can be characterized by that the average pore diameter sizes for a plurality of 100 µm$^2$ subareas of the same superabsorbent material vary by less than 50%, less than 40%, less than 30%, less than 20%, or less than 10%. In some further embodiments, the similarity or uniformity of the pore diameter size within the same superabsorbent material can be characterized by that the average pore diameter sizes for a plurality of 100 µm$^2$ subareas of the same superabsorbent material vary by about 50%, about 40%, about 30%, about 20%, about 10%, or any range between any two numbers listed in this sentence. In some additional embodiments of the superabsorbent materials provided in this paragraph, the subvolumes used for determining the pore diameter size could be a subarea of 10 µm$^2$, 20 µm$^2$, 30 µm$^2$, 40 µm$^2$, 50 µm$^2$, 60 µm$^2$, 70 µm$^2$, 80 µm$^2$, 90 µm$^2$, 100 µm$^2$, 150 µm$^2$, 200 µm$^2$, 250 µm$^2$, 300 µm$^2$, 350 µm$^2$, 400 µm$^2$, 450 µm$^2$, or 500 µm$^2$. In other embodiments of the superabsorbent materials provided in this paragraph, the pore densities can be determined and compared across 3, 4, 5, 6, 7, 8, 9, 10, 11, 12, 13, 14, 15, 16, 17, 18, 19, or 20 such subareas.

Additionally, in some embodiments, the similarity or uniformity of the pore diameter size within the same superabsorbent material can be characterized by the coefficient of variation of the pore diameter sizes of the same superabsorbent material being less than 1. In certain embodiments, the similarity or uniformity of the pore diameter size within the same superabsorbent material can be characterized by the coefficient of variation of the pore diameter sizes of the same superabsorbent material being less than 2, less than 1.9, less than 1.8, less than 1.7, less than 1.6, less than 1.5, less than 1.4, less than 1.3, less than 1.2, or less than 1.1, less than 1, less than 0.9, less than 0.8, less than 0.7, less than 0.6, less than 0.5, less than 0.4, less than 0.3, less than 0.2, or less than 0.1. In some additional embodiments, the similarity or uniformity of the pore diameter size within the same superabsorbent material can be characterized by the coefficient of variation of the pore diameter sizes of the same superabsorbent material being about 2, about 1.9, about 1.8, about 1.7, about 1.6, about 1.5, about 1.4, about 1.3, about 1.2, or about 1.1, about 1, about 0.9, about 0.8, about 0.7, about 0.6, about 0.5, about 0.4, about 0.3, about 0.2, about 0.1, or any range between any two numbers listed in this sentence. In other embodiments, the similarity or uniformity of the pore diameter size within the same superabsorbent material can be characterized by that the pore diameter sizes of the same superabsorbent material vary by less than 50%, less than 40%, less than 30%, less than 20%, or less than 10%. In some further embodiments, the similarity or uniformity of the pore diameter size within the same superabsorbent material can be characterized by that the pore diameter sizes of the same superabsorbent material vary by about 50%, about 40%, about 30%, about 20%, about 10%, or any range between any two numbers listed in this sentence.

In some specific embodiments of the superabsorbent materials provided herein, the coefficient of variation of the pore density of 1 mm3 subvolumes of the same superabsorbent material is less than 1. In certain embodiment, the coefficient of variation of the pore diameter size is less than 1. In other embodiments, the coefficient of variation of the pore density of 1 mm3 subvolumes of the same superabsorbent material is less than 1 and the coefficient of variation of the pore diameter size are less than 1.

In some embodiments of the porous network structure, the densely-populated pores are organized in a highly uniform pattern resembling a honey comb pattern, a reticulation pattern, or a combination thereof. In certain embodiments, the porous network structure includes a plurality of interconnected pores in which one pore is interconnected with another pore via one or more channels or open pores. In some embodiments of the superabsorbent material, there are two or more layers of the porous network structure, wherein each layer comprises a porous network structure. Advantageously, the disclosed porous network structure enables the superabsorbent material to have superior volume expansion and water absorption properties, as described herein.

As further described above, the structure of the superabsorbent material can also be characterized by the similarity of the porous network structure from one subarea or subvolume of superabsorbent material to another subarea or subvolume of superabsorbent material. Accordingly, in various embodiments of the superabsorbent materials provided herein, the porous network structure of the superabsorbent material has a uniform pattern that repeats in the superabsorbent material. In one embodiment, the pattern of the porous network structure of the superabsorbent material repeats such that a micrograph of one area of the superabsorbent material can form a cross correlation peak with a micrograph of another non-overlapping area of the same superabsorbent material. In another embodiment, the pattern of the porous network structure of the superabsorbent material repeats such that no less than 50%, 55%, 60%, 65%, 70%, 75%, 80%, 85%, 90%, or 95% of micrographs of the same superabsorbent material classify into one class in an image classification of an image set comprising both the micrographs of the same superabsorbent material and control micrographs from a control material, wherein the image classification is based on multivariate statistical analysis, principal component analysis, or maximum likelihood under suitable classification parameters and wherein the control material is not a superabsorbent material. In some embodiments, the control material is not a superabsorbent material, such as a conventional sponge known and used in the field. Various programs and algorithms are known and used in the field to calculate the cross-correlation between two images or classify a set of images, including software packages such as RELION, EMAN, SPIDER, Scipion, and/or protomo, which applies the known algorithms of multivariate statistical analysis, principal component analysis, and/or maximum likelihood.

A pore can be characterized by its diameter size, its pore size distribution, its surface area/pore volume, or its pore density. For example, when the superabsorbent material is hydrated or rehydrated, the pores can have an average diameter size in the range of 1 µm to 30 µm, or any range subsumed therein, including but not limited to 2 µm to 15 µm. A few small pores may have tens of nanometers to 1 µm. When the superabsorbent material is hydrated or rehydrated, the two-dimensional pore density can vary in less than 1 per 100 µm$^2$ to more than 500 per 100 µm$^2$. Further, a pore can be in any suitable shape, including but not limited to, a substantially hexagonal shape, a substantially pentagonal shape, a substantially circular shape, a substantially rectangular shape, or any other suitable pore shape. In certain embodiments, a pore can be interconnected with another pore via one or more channels.

In certain embodiments, the superabsorbent material particle has a large internal cavity volume, which can be at least 10 times to up to 150 times of the volume of the unswelled superabsorbent material. In certain embodiments, the superabsorbent material disclosed herein does not have a layered or sheeted structure.

As demonstrated in the working examples, the structural analyses suggest that some of the disclosed superabsorbent materials such as Sample Nos. 1 and 5-7, and to a lesser degree, Sample Nos. 9-11 formed a composite, porous, organized structure. Surprisingly, the soluble polysaccharides and insoluble fibers in the superabsorbent materials can expand concertedly such that the insoluble fibers expand and disperse evenly when the superabsorbent materials absorb water and expand in volume. This is a surprising feature because insoluble fiber is not miscible with water and is not expected to follow along with the soluble polysaccharides during the water absorption and volume expansion process. It appears that the insoluble fibers and soluble polysaccharides form a new composite structure that absorbs water and expand in volume concertedly. This observation suggests that the molecules of different components, including soluble natural polysaccharides and insoluble fibers interact with each other to form a new matter, rather than simple physical mixtures of various polymer which would be expected to show heterogeneous structural features and independent expansion behaviors.

In certain embodiments, the superabsorbent material has a superior swelling capacity in terms of water absorption ratio and volume expansion ratio at room temperature (for example, at a temperature between 15° C. and 25° C.), or at human body temperature (for example, at a temperature between 35° C. and 41° C.), and/or under a neutral pH condition or a human gastric pH condition. In some embodiments, the superabsorbent material disclosed herein have a highly porous network structure that is stable in the drying and hydration/rehydration processes under neutral and low pH solution mimicking human gastric condition. Upon hydration or rehydration, the superabsorbent material can expand in volume rapidly (in less than 30 minutes) and maintain a well-defined shape with the insoluble fiber being evenly distributed for at least 24 hours under a neutral pH condition or a human gastric pH condition. In some embodiments, the superabsorbent material disclosed herein is stable under an acidic pH such as a gastric pH and maintains the structure and the volume under the acidic gastric pH such that the induced satiety effect in a subject is prolonged.

As used herein, the swelling capacity is represented by absorption ratio measured by the following formula: absorption ratio=the wet weight of the superabsorbent material swelled in water or a specific buffer to saturation divided by the dry weight of the superabsorbent material, and by volume expansion ratio measured by the following formula: volume expansion ratio=the volume of the fully hydrated/rehydrated superabsorbent material soaked in water or a specific buffer to saturation divided by the volume of the starting dry superabsorbent material. In some embodiments, the absorption ratio and/or the volume expansion ratio is measured at room temperature. In some embodiments, the absorption ratio and/or the volume expansion ratio is measured at about 37° C. In some embodiments, the absorption ratio and/or the volume expansion ratio is measured at a neutral pH. In some embodiments, the absorption ratio and/or the volume expansion ratio is measured at a physiological pH. In some embodiments, the absorption ratio and/or the volume expansion ratio is measured at a gastric pH. In some embodiments, the superabsorbent materials obtained by the process disclosed herein have a water absorption ratio of at least 10 fold, at least 20 fold, at least 30 fold, at least 40 fold, at least 50 fold, at least 60 fold, at least 70 fold, at least 80 fold, at least 90 fold, at least 100 fold, at least 110 fold, at least 120 fold, at least 130 fold, at least 140 fold, at least 150 fold, at least 160 fold, at least 170 fold, at least 180 fold, at least 190 fold, or at least 200 fold of the weight of the dry superabsorbent material before swelling. In some embodiments, the superabsorbent materials obtained by the process disclosed herein have a volume expansion ratio in water of at least 10 fold, at least 20 fold, at least 30 fold, at least 40 fold, at least 50 fold, at least 60 fold, at least 70 fold, at least 80 fold, at least 90 fold, at least 100 fold, at least 110 fold, at least 120 fold, at least 130 fold, at least 140 fold, or at least 150 fold of the weight of the dry superabsorbent material before swelling.

In various embodiments of the superabsorbent materials provided herein, the dry superabsorbent material, which is the superabsorbent material before hydration or rehydration, has a highly-packed porous network structure such that upon hydration or rehydration, the pore density reduces 10 to 150 fold and/or the pore diameter size increases 10 to 150 fold. In one embodiment, the porous network structure of the dry superabsorbent material is densely-packed with small pore sizes. In some further embodiments, the small pore size of the porous network structure of the dry superabsorbent material is characterized by a pore diameter size $1/10$ to $1/150$ of the pore diameter size of the superabsorbent material after hydration or rehydration. In certain further embodiments, the small pore size of the porous network structure of the dry superabsorbent material is characterized by a pore diameter size $1/2$, $1/3$, $1/4$, $1/5$, $1/6$, $1/7$, $1/8$, $1/9$, $1/10$, $1/11$, $1/12$, $1/13$, $1/14$, $1/15$, $1/16$, $1/17$, $1/18$, $1/19$, $1/20$, $1/25$, $1/30$, $1/35$, $1/40$, $1/45$, $1/50$, $1/55$, $1/60$, $1/65$, $1/70$, $1/80$, $1/85$, $1/90$, $1/95$, $1/100$, $1/105$, $1/110$, $1/120$, $1/125$, $1/130$, $1/135$, $1/140$, $1/145$, $1/150$, $1/155$, $1/160$, $1/165$, $1/170$, $1/175$, $1/180$, $1/185$, $1/190$, $1/195$, $1/200$, or any range between any two numbers listed in this sentence, of the pore diameter size of the superabsorbent material after hydration or rehydration. In other embodiments, the small pore size of the porous network structure of the dry superabsorbent material is characterized by that the pore diameter size of the superabsorbent material after hydration or rehydration is 2, 3, 4, 5, 6, 7, 8, 9, 10, 11, 12, 13, 14, 15, 16, 17, 18, 19, 20, 25, 30, 35, 40, 45, 50, 55, 60, 65, 70, 80, 85, 90, 95, 100, 105, 110, 120, 125, 130, 135, 140, 145, 150, 155, 160, 165, 170, 175, 180, 185, 190, 195, 200, or any range between any two numbers listed in this sentence, fold of pore diameter size of the dry superabsorbent material. In some additional embodiments, the pore diameter size of the superabsorbent material after hydration or rehydration in this paragraph can be any such pore diameter size as described herein, including in the "Summary" Section, this Section ("Detailed Description"), and the "Example" Section.

Similarly, in one embodiment, the porous network structure of the dry superabsorbent material is densely-packed with small pore sizes. In some further embodiments, the dense packing of pores in the porous network structure of the dry superabsorbent material is characterized by a pore density 10 to 150 fold of the pore density of the superabsorbent material after hydration or rehydration. In certain further embodiments, the dense packing of pores in the porous network structure of the dry superabsorbent material is characterized by a pore density 2, 3, 4, 5, 6, 7, 8, 9, 10, 11, 12, 13, 14, 15, 16, 17, 18, 19, 20, 25, 30, 35, 40, 45, 50, 55, 60, 65, 70, 80, 85, 90, 95, 100, 105, 110, 120, 125, 130, 135, 140, 145, 150, 155, 160, 165, 170, 175, 180, 185, 190, 195, 200, or any range between any two numbers listed in this sentence, fold of the pore density of the superabsorbent material after hydration or rehydration. In some additional embodiments, the pore density of the superabsorbent material after hydration or rehydration in this paragraph can be any such pore density as described herein, including in the "Summary" Section, this Section ("Detailed Description"), and the "Example" Section.

The disclosure provides that the superior absorbent properties of the superabsorbent materials can be supported by the porous network structure of the superabsorbent materials provided herein and the porous network structure can be supported by the various bonds within the porous network structure. In various embodiments of the superabsorbent materials provided herein, the porous network of the dry superabsorbent material comprise polysaccharide chains connected by viscoelastic bonds and such polysaccharide chains are entangled at a few points leading to a permanent three-dimensional porous network structure.

Methods of Making the Composite Superabsorbent Materials

In another aspect, disclosed herein is a process of obtaining a superabsorbent material comprising one or more soluble polysaccharides, such as gelling polysaccharides and gelling-compatible polysaccharides, and one or more insoluble dietary fibers. The process comprises the steps of dissolving one or more water-soluble polysaccharides, such as gelling polysaccharides and gelling-compatible polysaccharides, or one or more compositions containing one or more water-soluble polysaccharides, such as gelling polysaccharides and gelling-compatible polysaccharides, at various ratio and mass concentrations in water to form a solution, adding one or more insoluble fibers or one or more compositions containing one or more insoluble fibers at various ratio and mass concentrations to water to form a dispersion, which is optionally subjected to high pressure homogenization, mixing the solution containing the one or more soluble polysaccharides, such as gelling polysaccharides and gelling-compatible polysaccharides, and the dispersion containing the one or more insoluble fibers, subjecting the mixture to suitable conditions to form a gel, freezing the gel, and drying the frozen gel to obtain the superabsorbent material. In some embodiments, the freezing the gel step induces cryogelation. The superabsorbent material disclosed herein is neither expanded with a gas nor digested with an enzyme prior to or during the formation of the superabsorbent material. The obtained superabsorbent materials have a highly porous network structure and large surface area and can absorb a large amount of other molecules such as water molecules. Upon hydrated or rehydration at room or body temperature while maintaining the porous network structure, the obtained superabsorbent materials can absorb a large amount of water, expand in volume and maintain a well-defined structure at room or body temperature, and under neutral or gastric conditions. The superabsorbent materials disclosed herein can maintain its porous network structure for a prolonged period even in the gastric environment at human body temperature.

The disclosure further provides that the superabsorbent materials were prepared in one of the method steps as hydrated gels before freezing and then drying into dry superabsorbent materials. The dry superabsorbent materials can be hydrated into a gel. The dry superabsorbent materials can also be rehydrated back into a gel in view that such superabsorbent materials have been hydrated before. The superabsorbent materials can be subjected to one or more (e.g. 1, 2, 3, 4, 5, 6, 7, 8, or 9) freezing and drying cycles. In one embodiment, the superabsorbent material is subjected to one freezing and drying cycle. In some embodiments, the disclosure provides that hydrated gels before any freezing and drying can be different from the hydrated (or rehydrated) superabsorbent materials after the steps of freezing and drying as a result of the freezing and drying. In some embodiments, the freezing and drying contribute to the porous network structure of the superabsorbent materials.

The disclosure provides that the one or more water-soluble polysaccharides for the methods provided herein can be any or any combination of such polysaccharides provided in this Section (Detailed Description), the Section of "Summary," and the Section of "Examples." The one or more gelling polysaccharides for the methods provided herein can be any or any combination of such gelling polysaccharides provided in this Section (Detailed Description), the Section of "Summary," and the Section of "Examples." The one or more gelling-compatible polysaccharides for the methods provided herein can be any or any combination of such gelling-compatible polysaccharides provided in this Section (Detailed Description), the Section of "Summary," and the Section of "Examples." The ratio by weight between the total amount of the water-soluble polysaccharides and the total amount of the insoluble fibers can be any such ratios provided in this Section (Detailed Description), the Section of "Summary," and the Section of "Examples." The one or more insoluble fibers for the methods provided herein can be any or any combination of such fibers provided in this Section (Detailed Description), the Section of "Summary," and the Section of "Examples." The porous network structure of the superabsorbent materials made by the methods provided herein can be any such structure provided in this Section (Detailed Description), the Section of "Summary," and the Section of "Examples." The pore density (including the average, variation, and range) of the superabsorbent materials made by the methods provided herein can be any pore density for such superabsorbent material as provided in this Section (Detailed Description), the Section of "Summary," and the Section of "Examples." The pore diameter size (including the average, variation, and range) of the superabsorbent materials made by the methods provided herein can be any pore diameter size for such superabsorbent material as provided in this Section (Detailed Description), the Section of "Summary," and the Section of "Examples." The volume expansion ratio (including the fold expansion and duration to achieve such fold expansion) of the superabsorbent materials made by the methods provided herein can be any volume expansion ratio for such superabsorbent material as provided in this Section (Detailed Description), the Section of "Summary," and the Section of "Examples." As is clear from the disclosure, the various embodiments of the methods provided herein can be used to prepare various embodiments of the superabsorbent materials provided herein.

In certain embodiments, heating to a temperature to above 60° C. and/or stirring facilitate complete dissolving of the one or more polysaccharides. In some embodiments, the mixture of the solution containing the polysaccharide and the dispersion containing the insoluble fiber is cooled down to between 20° C. and 25° C. to form a gel over an extended period (the temperature and time for the gelling step can be optimized depending on materials used). In some embodiments, the gel is completely frozen before the drying step. In some embodiments, the freezing step includes freezing the gel to induce cryo-gelation at a temperature of −5° C. to −80° C. for at least 12 hours, at least 24 hours, at least 36 hours, at least 48 hours, at least 60 hours, at least 72 hours, at least 84 hours, at least 96 hours, at least 108 hours, at least 120 hours, at least 196 hours, or more. In some embodiments, the gel is completely frozen before the drying step. In some embodiments, the freezing step includes freezing the gel to induce cryo-gelation at a temperature of −5° C. to −80° C. for about 6 hours, about 12 hours, about 24 hours, about 36 hours, about 48 hours, about 60 hours, about 72 hours, about 84 hours, about 96 hours, about 108 hours, about 120 hours, about 196 hours, or more. In some additional embodiments, the freezing step includes freezing the gel to induce cryo-gelation at a temperature of about −5° C., about −10° C., about −15° C., about −20° C., about −25° C., about −30° C., about −35° C., about −40° C., about −45° C., about −50° C., about −55° C., about −60° C., about −65° C., about −70° C., about −75° C., about −80° C., or any range between any two temperatures listed in this sentence. In further embodiments, the freezing step includes freezing the gel to induce cryo-gelation for about 6 hours, about 12 hours, about 24 hours, about 36 hours, about 48 hours, about 60 hours, about 72 hours, about 84 hours, about 96 hours, about 108 hours, about 120 hours, about 196 hours, or more. In other embodiments, the freezing step includes freezing the gel to induce cryo-gelation for at least 6 hours, at least 12 hours, at least 24 hours, at least 36 hours, at least 48 hours, at least 60 hours, at least 72 hours, at least 84 hours, at least 96 hours, at least 108 hours, at least 120 hours, at least 196 hours, or more. Any drying methods that can remove water without damaging the porous network structure and diminishing the water absorption capacity and volume expansion function can be used. In some embodiments, the method further comprises pulverizing the dried gel to obtain the superabsorbent material in a powder form of various mesh sizes depending on specific application needs. In some embodiments, the drying step includes freeze-drying or vacuum freeze-drying the frozen gel. In some embodiments, the drying step includes thawing the frozen gel, filtering the thawed gel to obtain a filter cake, and drying the filter cake. The filter cake can be dried by any suitable method, including but not limited to air drying, heat drying, freeze-drying, vacuum drying, or a combination thereof.

In various embodiments of the methods provided herein, for at least 24 hours after hydration or rehydration with water having a pH of about 7 at room temperature, the superabsorbent material has a gel strength that is increased by at least 90% compared to a gel strength of the gel before the freezing step. In some embodiments of the methods provided herein, for at least 24 hours after hydration or rehydration with water having a pH of about 7 at room temperature, the superabsorbent material has a gel strength that is increased by at least 90%, at least 95%, at least 100%, at least 105%, at least 110%, at least 120%, at least 125%, at least 130%, at least 135%, at least 140%, at least 145%, at least 150%, at least 160%, at least 170%, at least 180%, at least 190%, at least 200%, at least 250%, at least 300%, at least 350%, at least 400%, or more compared to a gel strength of the gel before the freezing step. In some embodiments of the methods provided herein, for about 24 hours after hydration or rehydration with water having a pH of about 7 at room temperature, the superabsorbent material has a gel strength that is increased by about 90%, about 95%, about 100%, about 105%, about 110%, about 120%, about 125%, about 130%, about 135%, about 140%, about 145%, about 150%, about 160%, about 170%, about 180%, about 190%, about 200%, about 250%, about 300%, about 350%, about 400%, or more compared to a gel strength of the gel before the freezing step. The gel strength of the gel before the freezing step and the gel after hydration or rehydration can be determined by any means provided herein, for example, by storage modulus and/or gel rupture force.

Similarly, in various embodiments of the methods provided herein, for at least 24 hours after hydration or rehydration in an acidic solution at room temperature, the superabsorbent material has a gel strength of at least 80% compared to a gel strength of the gel before the freezing step. In some embodiments of the methods provided herein, for at least 24 hours after hydration or rehydration in an acidic solution at room temperature, the superabsorbent material has a gel strength of at least 90%, at least 95%, at least 100%, at least 105%, at least 110%, at least 120%, at least 125%, at least 130%, at least 135%, at least 140%, at least 145%, at least 150%, at least 160%, at least 170%, at least 180%, at least 190%, at least 200%, at least 250%, at least 300%, at least 350%, at least 400%, or more compared to a gel strength of the gel before the freezing step. In some embodiments of the methods provided herein, for about 24 hours after hydration or rehydration in an acidic solution at room temperature, the superabsorbent material has a gel strength of about 90%, about 95%, about 100%, about 105%, about 110%, about 120%, about 125%, about 130%, about 135%, about 140%, about 145%, about 150%, about 160%, about 170%, about 180%, about 190%, about 200%, about 250%, about 300%, about 350%, about 400%, or more compared to a gel strength of the gel before the freezing step. The gel strength of the gel before the freezing step and the gel after hydration or rehydration can be determined by any means provided herein, for example, by storage modulus and/or gel rupture force. The acidic solution in this paragraph can be a solution of pH 1, 2, 3, 4, 5, or 6. In one embodiment, the acidic solution in this paragraph can be a solution of gastric pH.

In some specific embodiments, the methods provided herein can comprise some additional steps such as homogenization. In one specific embodiment, the methods provided herein comprise subjecting the dispersion to high pressure homogenization at a pressure of 10-50 MPa before mixing with the solution. In another embodiment, the methods provided herein comprise subjecting the dispersion to high pressure homogenization at a pressure of 10-40 MPa, 10-30 MPa, 10-20 MPa, 10-15 MPa, 5-50 MPa, 5-40 MPa, 5-30 MPa, 5-20 MPa, 5-15 MPa, 15-50 MPa, 15-40 MPa, 15-30 MPa, 15-20 MPa, 20-50 MPa, 20-40 MPa, 20-30 MPa, 25-50 MPa, 25-40 MPa, or 25-30 MPa, before mixing with the solution. In yet another embodiment, the methods provided herein comprise subjecting the dispersion to high pressure homogenization at a pressure of at least 5, at least 10, at least 15, at least 20, at least 25, at least 30, at least 35, at least 40, at least 45, at least 50, at least 55, or at least 60 MPa, before mixing with the solution. In yet another embodiment, the methods provided herein comprise subjecting the dispersion to high pressure homogenization at a pressure of about 5, about 10, about 15, about 20, about 25, about 30, about 35, about 40, about 45, about 50, about 55, about 60 MPa, or any range of any two numbers listed in this sentence, before mixing with the solution.

Since the final product is not a gel but rather a dehydrated material that can be used to absorb water and expand volume in a certain shape upon hydration or rehydration, the disclosed technology allows removing water from the composite gel while maintaining its structural integrity and functionality. The superabsorbent materials disclosed herein are dehydrated by two types of processes. In some embodiments of the methods provided herein, the methods comprise a step to thaw the materials and dry at an elevated temperature (e.g. 50-60° C.) without melting the gel structure under atmospheric pressure. In other embodiments of the methods provided herein, the methods comprise a step to directly freeze dry the frozen gel under vacuum. In a specific embodiment, the drying step of the various methods provided herein comprises directly drying the frozen gel by lyophilization without thawing. Both methods yield superabsorbent materials with good to great water absorption and volume expansion properties. Generally, the freeze-dried samples have a more porous structure and higher water absorption capacity, while the thawing-dried samples have a more compact structure in the dry state but can resume a porous structure upon hydration or rehydration, although the water absorption capacity is lower than that of the freeze-dried samples. However, the thawing-dried materials have a smaller starting volume and show a larger fold of volume expansion than the freeze-dried materials.

As demonstrated in the working examples, the superabsorbent materials composed of soluble polysaccharides, such as gelling polysaccharides and gelling-compatible polysaccharides, and insoluble fibers can be obtained by selecting the proper ingredients at an optimized ratio or concentration, using freezing techniques to physically enhance the gel stability without crosslinking, and drying the sample either by thawing and dry or by freeze and dry, as well as other suitable drying methods to main the gel matrix structure, thereby to result in a final product having a uniform structure and great water absorption capacity. The superabsorbent materials obtained by the disclosed technology can greatly expand in volume upon hydration or rehydration and maintain the shape over a long period time under both neutral pH and gastric pH conditions at room temperature or body temperature.

In certain embodiments, the superabsorbent material disclosed herein includes a seaweed composite material comprising one or more insoluble fibers and agar disclosed and made by a process disclosed herein and in PCT Application No. PCT/US2020/070160, filed on Jun. 19, 2020 and published as WO2020/257825 on Dec. 24, 2020 (which is herein incorporated in its entirety by reference), a seaweed composite material comprising one or more insoluble fibers and carrageenan disclosed and made by a process disclosed herein and in PCT Application No. PCT/US2020/070161, filed on Jun. 19, 2020 and published as WO2020/257826 on Dec. 24, 2020 (which is herein incorporated in its entirety by reference), a soybean dietary fiber composition disclosed and made by a process disclosed herein and in PCT Application No. PCT/US2021/014388, filed on Jan. 21, 2021 (which is incorporated herein in its entirety by reference), or a combination thereof.

This disclosure and PCT Application No. PCT/US2020/070160, filed on Jun. 19, 2020 and published as WO2020/257825 on Dec. 24, 2020 (which is herein incorporated in its entirety by reference), and PCT Application No. PCT/US2020/070161, filed on Jun. 19, 2020 and published as WO2020/257826 on Dec. 24, 2020 (which is herein incorporated in its entirety by reference) discloses methods for making seaweed composite material that is less processed compared to conventional methods because the disclosed methods maintains the natural association between the insoluble fiber (e.g. cellulose, insoluble hemicellulose) and polysaccharide (e.g. agar, carrageenan) without any substantial disruption or dissociation of the polysaccharide from the insoluble fiber. The obtained seaweed composite material comprises one or more insoluble fibers and polysaccharide associated with the insoluble fiber. The term "associated" or "association" means that the polysaccharide is bound to the surface of the insoluble fiber, the insoluble fiber is partially or entirely encapsulated by the polysaccharide, or the insoluble fiber is partially or entirely embedded within the polysaccharide. In some embodiments, the insoluble fiber forms a "bundled" fiber core, with the polysaccharide bound to the surface of the insoluble fiber core in the seaweed composite material.

As disclosed herein and in PCT Application No. PCT/US2020/070160, filed on Jun. 19, 2020 and published as WO2020/257825 on Dec. 24, 2020 (which is herein incorporated in its entirety by reference), the method of making a seaweed composite material comprises the steps of treating the fresh or dried seaweed with one or more alkalis before the acid treatment, treating the fresh or dried seaweed with one or more acids, grinding the acid-treated seaweed by wet milling or dry grinding, subjecting the ground seaweed to high pressure homogenization (HPH), and drying and grinding the homogenized seaweed to a desired particle size to obtain the seaweed composite material. Further details are provided in Process 1, Alkali treatment followed by acid treatment, at [0025]-[0031] of PCT Application No. PCT/US2020/070160, as filed on Jun. 19, 2020 and published as WO2020/257825 on Dec. 24, 2020 (which is herein incorporated in its entirety by reference) and also disclosed herein. In some embodiments, the HPH is carried out at a temperature of between 0° C. and 50° C. such as between 20° C. and 40° C., or between 25° C. and 30° C. In some embodiments, the HPH is carried out at room temperature. The obtained seaweed composite material has a high gelling strength and a high molecular weight. For example, the obtained seaweed composite material has an average molecular weight of 100-1000 kDa, and/or a gelling strength of 200-1000 g/cm$^2$ at 1.5%. In some embodiments, the seaweed is washed and/or cleaned to remove debris before the acid treatment. In some embodiments, the seaweed is bleached by one or more bleaching agents before HPH.

The seaweed composite material produced by any of the methods disclosed herein and in PCT Application No. PCT/US2020/070160, filed on Jun. 19, 2020 and published as WO2020/257825 on Dec. 24, 2020 (which is herein incorporated in its entirety by reference), such as Processes 1-3 at [0025]-[0052] of such PCT application referenced in this sentence. The seaweed composite material comprises one or more insoluble fibers and agar, wherein the agar is associated with the insoluble fiber. In some embodiments, the insoluble fiber includes cellulose and insoluble hemicelluloses. In some embodiments, the insoluble fiber is associated with agar in a manner similar to the association in the natural state in seaweed before processing. In some embodiments, agar is bound to the surface of the insoluble fiber such as cellulose of the seaweed composite material. In some embodiments, the insoluble fiber is entirely or partially embedded within agar. In some embodiments, the insoluble fiber is partially or entirely encapsulated by agar. In some embodiments, the seaweed composite material has a particle size of less than or about 100 μm, less than or about 90 μm, less than or about 80 μm, less than or about 70 μm, less than or about 60 μm, less than or about 50 μm, less than or about 40 μm, less than or about 30 μm, less than or about 20 μm, less than or about 10 μm, less than or about 5 μm, less than or about 4 μm, less than or about 3 μm, less than or about 2 μm, or less than or about 1 μm. In some embodiments, the seaweed composite material has a particle size of between 0.1 μm and 100 μm, between 1 μm and 100 μm, between 10 μm and 90 μm, between 20 μm and 80 μm between 30 μm and 70 μm, between 40 μm and 60 μm, between 0.5 μm and 20 μm, between 1 μm and 15 μm, between 2 μm and 10 μm, between 3 μm and 8 μm, between 4 μm and 7 μm, or between 5 μm and 6 μm.

As disclosed herein and in PCT Application No. PCT/US2020/070161, filed on Jun. 19, 2020 and published as WO2020/257826 on Dec. 24, 2020 (which is herein incorporated in its entirety by reference), the method of making seaweed composite material comprises the steps of pretreating the fresh or dried seaweed with a salt such as potassium chloride (KCl) at a high concentration under heat such as at 80-100° C., subjecting the pretreated seaweed to high pressure homogenization (HPH), and drying and grinding the homogenized seaweed to a desired particle size to obtain the seaweed composite material. In some embodiments, the seaweed is ground by wet milling or dry grinding before or after the salt treatment. In some embodiments, the HPH is carried out at a temperature of between 0° C. and 50° C., e.g., between 20° C. and 40° C., between 25° C. and 30° C., or at room temperature. In some embodiments, the KCl treatment is carried out before high pressure homogenization under heating at 80-100° C. for 1-6 hours, and the HPH can be carried out at low temperature between 0-50° C. without melting carrageenan off from its native plant matrix comprising the insoluble fiber. The obtained seaweed composite material has a gelling strength in the range of 200-1000 g/cm$^2$ depending on the starting seaweed materials and manufacturing processes. In some embodiments, the seaweed is washed and/or cleaned to remove debris before grinding or the salt treatment. In some embodiments, the seaweed is bleached by one or more bleaching agents before HPH.

As further disclosed herein and in PCT Application No. PCT/US2020/070161, filed on Jun. 19, 2020 and published as WO2020/257826 on Dec. 24, 2020 (which is herein incorporated in its entirety by reference), the seaweed composite material can be produced by any of the methods disclosed herein and in WO2020/257826, such as Processes 1-3 at [0028]-[0049] in WO2020/257826. The seaweed composite material comprises one or more insoluble fibers such as cellulose and insoluble hemicelluloses and carrageenan, wherein the carrageenan is associated with the insoluble fiber when the HPH step is carried out at a temperature of between 0° C. and 50° C., e.g., between 20° C. and 40° C., between 25° C. and 30° C., or at room temperature. In some embodiments, the insoluble fiber is associated with carrageenan in a manner similar to the association in the natural state in seaweed before processing. In some embodiments, the carrageenan is bound to the surface of the insoluble fiber such as cellulose of the seaweed composite material. In some embodiments, the insoluble fiber is entirely or partially embedded within carrageenan. In some embodiments, the insoluble fiber is partially or entirely encapsulated by carrageenan. In some embodiments, the seaweed composite material has a particle size of less than or about 100 μm, less than or about 90 μm, less than or about 80 μm, less than or about 70 μm, less than or about 60 μm, less than or about 50 μm, less than or about 40 μm, less than or about 30 μm, less than or about 20 μm, less than or about 10 μm, less than or about 5 μm, less than or about 4 μm, less than or about 3 μm, less than or about 2 μm, or less than or about 1 μm. In some embodiments, the seaweed composite material has a particle size of between 0.1 μm and 100 μm, between 1 μm and 100 μm, between 10 μm and 90 μm, between 20 μm and 80 μm between 30 μm and 70 μm, between 40 μm and 60 μm, between 0.5 μm and 20 μm, between 1 μm and 15 μm, between 2 μm and 10 μm, between 3 μm and 8 μm, between 4 μm and 7 μm, or between 5 μm and 6 μm.

As disclosed herein and in PCT Application No. PCT/US2021/014388, filed on Jan. 21, 2021 (which is incorporated herein in its entirety by reference), the method of making a dietary fiber composition from soybean dregs or soybean residues comprises the steps of treating the fresh or dried soybean dregs or soybean residues with an alkali such as NaOH or KOH at a concentration between 0.2%-5% (w/w) at a temperature between 50° C. and 100° C. for a period between 0.5 hour and 20 hours, optionally bleaching the alkaline treated material with a bleaching agent, optionally subjecting the material to high pressure homogenization (HPH), and drying and grinding the material to a desired particle size to obtain the dietary fiber composition. When the alkali concentration is low (e.g., less than 0.2% (w/w)), the reaction between the alkali and the dietary fiber is weak, resulting in only a small change in the structure of the composition, and therefore the viscosity and water retention capacity are both low. Under the low alkali conditions, the protein in the raw materials of soybean dregs or soybean residues cannot be effectively removed. Compositions obtained by low concentration alkaline treatment had a relatively high protein content and a relatively low fiber content. On the other hand, when the alkali concentration and temperature are too high, the fiber structure is easily disrupted, resulting in excessive decomposition of the fiber, making it difficult to prepare dietary fiber with higher viscosity. Although the combination of high alkali concentration and low treatment temperature may result in dietary fiber compositions having high viscosity, the production efficiency is low and the production cost is high due to the extra cost of waste treatment. Thus, the process can be carried out at an alkali concentration of between 0.3% and 1.0% (w/w) at a temperature between 70° C. and 85° C. for between 2 hours and 6 hours. Thus, in certain embodiments, the alkaline treatment is carried out at an alkali concentration between 0.3% and 1.0% (w/w). In certain embodiments, the alkaline treatment is carried out at a temperature between 70° C. and 85° C. In certain embodiments, the alkaline treatment is carried out for a period of time between 2 hours and 6 hours. Further process details are provided herein and, for example, at [0013]-[0018] and [0024]-[0034] in PCT Application No. PCT/US2021/014388, as filed on Jan. 21, 2021 (which is incorporated herein in its entirety by reference).

Applications of the Composite Superabsorbent Materials

The superabsorbent materials disclosed herein have various applications in healthcare and food industries. For example, the superabsorbent material can be used as a medical diet or dietary supplement, which can increase the satiety of the patient thereby to reduce the intake of calories and carbohydrate. Such a diet or dietary supplement, when used in combination with a therapy, can enhance the therapeutic effect on obesity and diabetes; and even when used alone, can prevent or delay the onset of certain diseases such as obesity and diabetes. In some embodiments, the superabsorbent materials disclosed herein can be used as a vehicle for loading medicine for the preparation of medical materials.

One popular dietary strategy is volumetric diet, which is the second best diet for weight loss and tied for the fifth best diet overall out of 40 diets evaluated by a panel of health experts in the 2018 U.S. News & World Report's Best Diet Rankings. The main concept of volumetric diet is to eat natural foods that are low in calories and high in fiber or water such as fruits, vegetables, and soup. Although volumetric diet has proven to be very effective in weight control and preventing obesity and diabetes, an apparent limitation of this strategy is the diversity of nutrients contained in each food that has high volume and water content but may lack certain essential nutrients. Nevertheless, two key features of volumetric diet are low calorie density and high-water content. As used herein, the term "calorie density" means the total calories provided per mass unit measure of food. A diet having a low calorie density means that for the same mass or same weight, a low calorie density diet provides less calorie than a regular diet.

Some examples of the applications of the superabsorbent materials disclosed herein include but are not limited to the following: (1) the superabsorbent materials disclosed herein can be added to a cold or warm liquid diet or a drink such as water, juice, milk, beverage, soup, and pudding for human consumption; (2) the superabsorbent materials disclosed herein can be directly consumed in the form of a powder, a tablet, a capsule or any other suitable form, followed by drinking an appropriate amount of liquid to allow liquid absorption and swelling in the stomach; (3) the superabsorbent materials disclosed herein can be added as an ingredient to various food products such as bread, cakes, biscuits, energy bars and other foods to make low-calorie, dietary fiber-rich functional foods and/or volumetric diet to induce satiety for a prolonged time. Because the superabsorbent materials disclosed herein can be in dry powder form and has superior swelling capacity, a small amount of consumption (about 5 g to 20 g) can achieve a satisfying satiety effect. The superabsorbent materials are also stable under normal shipping and storage conditions. Therefore, the superabsorbent materials can also be used as a vehicle to deliver drugs and other nutrients.

In some embodiments, the superabsorbent material or the dietary composition comprising the superabsorbent material further comprises one or more additional essential nutrients including macronutrients and micronutrients. Such nutrients include but are not limited to a variety of proteins and active peptides, vitamins and trace elements and minerals, and prebiotics.

As demonstrated in the working examples, different samples of the superabsorbent materials showed a wide range of water absorption capacity, suggesting that the composition, mass ratio and concentration can affect the properties of the superabsorbent materials. The disclosed superabsorbent materials are characterized by a highly stable and uniform structure, suggesting that molecules of different natural polysaccharides interact with each other to form a new and unique matter, rather than simple physical mixtures of various polymers which would be expected to show heterogeneous structural features. The different composite superabsorbent materials made from different soluble polysaccharides, such as gelling polysaccharides and gelling-compatible polysaccharides, and insoluble dietary fibers with different ratios and concentrations clearly have different structures, which explain their different functionalities such as water absorption ratio and volume expansion ratio as well as shape stability.

The following examples are intended to illustrate various embodiments of the invention. As such, the specific embodiments discussed are not to be construed as limitations on the scope of the invention. It will be apparent to one skilled in the art that various equivalents, changes, and modifications may be made without departing from the scope of invention, and it is understood that such equivalent embodiments are to be included herein. Further, all references cited in the disclosure are hereby incorporated by reference in their entirety, as if fully set forth herein.

EXAMPLES

Example 1

This example demonstrates preparation and characterization of various superabsorbent materials. The ingredients of each sample are disclosed in Table 1 below. The seaweed composite material from *Gracilaria* was obtained as described herein and in PCT Application No. PCT/US2020/070160, filed on Jun. 19, 2020 and published as WO2020/257825 on Dec. 24, 2020 (which is herein incorporated in its entirety by reference) (Sample A-2), and has about 29.4% insoluble fiber and about 45.7% soluble fiber. The seaweed composite material from *Eucheuma* was obtained as described herein and in PCT Application No. PCT/US2020/070161, filed on Jun. 19, 2020 and published as WO2020/257826 on Dec. 24, 2020 (which is herein incorporated in its entirety by reference) (Sample L), and has about 39.5% insoluble fiber and about 26.0% soluble fiber. The soybean fiber was obtained as described herein and in PCT Application No. PCT/US2021/014388, as filed on Jan. 21, 2021 (which is incorporated herein in its entirety by reference) (Sample D), and has about 76.1% insoluble fiber and about 12.2% soluble fiber.

TABLE 1

| Sample No | Ingredients and Concentrations (w/w) | Total water-soluble polysaccharide to total insoluble fiber | WRC at pH 7.0 | WRC at pH 1.0 |
|---|---|---|---|---|
| 1 | Seaweed composite material from *Gracilaria* (0.4%), seaweed composite material from *Eucheuma* (0.4%), and Konjac Gum (0.4%) | 2.49 | 25.8 | 21.2 |
| 2 | Seaweed composite material from *Gracilaria* (0.8%), seaweed composite material from *Eucheuma* (0.4%), and Konjac Gum (0.4%) | 2.21 | 16.6 | 16.1 |
| 3 | Seaweed composite material from *Gracilaria* (1.2%), seaweed composite material from *Eucheuma* (0.3%), and Konjac Gum (0.3%) | 1.97 | 13.4 | 12.9 |
| 4 | Seaweed composite material from *Gracilaria* (0.4%), seaweed composite material from *Eucheuma* (0.2%), Konjac Gum (0.2%), and soybean fiber (0.8%) | 0.66 | 14.5 | 12.7 |
| 5 | Agar (0.4%), Konjac Gum (0.2%), carrageenan (0.2%), and soybean fiber (0.8%) | 1.47 | 19.0 | 13.9 |

Sample preparation: The soluble ingredients except for soybean fiber were added to water at concentrations as detailed in Table 1, stirred and dispersed uniformly at high speed, and heated and boiled for 5 minutes to fully dissolve the water-soluble ingredients. For Sample Nos. 4 and 5, the soluble ingredients were added to 70% of water used to prepare the gel. The soybean fiber was added to 30% water used to prepare the gel, heated to above 60° C., and homogenized under a pressure of 10-50 MPa. The homogenized soybean fiber material was added to the colloidal solution containing dissolved ingredients, stirred and mixed uniformly, and the mixture was kept above 50° C. to prevent gel formation during the mixing process. Each liquid without soybean fiber for Sample Nos. 1-3 and with soybean fiber for Sample Nos. 4-5 was cooled to 20-25° C. and left to stand for more than 6 hours to form a gel. The gel was stored below −10° C. for 24 hours to completely freeze the gel. The frozen gel was thawed in air at 20-30° C. or immersed in 20-30° C. water. Subsequently, the thawed gel was filtered or centrifuged and dehydrated, followed by drying with hot air at 50-60° C. to reach a moisture content of less than about 15%.

Water absorption test: 1.0 g of a dry sample of the superabsorbent material prepared as disclosed above was mixed with 250 g of distilled water at pH 7.0 or 0.1 M HCl at pH 1.0 in a beaker, and the mixture was allowed to stand for 3 hours at 25° C. Then the sample in the beaker was poured onto a 120-mesh sieve and kept for 1 hour at 25° C. to allow the water to drip off naturally. The wet sample remained on the sieve was recovered and weighed. The absorption ratio was calculated as follows:

Water retention capacity (WRC)=the weight of the wet sample recovered from the sieve divided by the weight of the starting dry sample.

Volume expansion and shape stability analysis: Particles of Sample Nos 1-5 were soaked in deionized water (ddw) or 0.1 M HCl solution for over 24 hours. The images of their dry and wet status after 24 hours were taken using Leica MZ 125 microscope and shown in FIG. 1.

This example demonstrates that various samples of the composite superabsorbent materials expanded in volume upon rehydration, and the degree of volume expansion generally correlated with the water absorption ratio measured by weight (see Table 1). Sample No. 1 and Sample No. 5 showed larger volume expansion than Sample Nos 2-4. In general, volume expansion was lower in 0.1 M HCl than in water at pH 7.0. This observation was more obvious when comparing Sample No. 1 and Sample No. 5. While Sample No. 1 had good volume expansion in both water at pH 7.0 and 0.1 M HCl, Sample No. 5 showed a lower volume expansion in 0.1 M HCl than in water at pH 7.0. Another observation was that the insoluble fiber became spread out and evenly distributed in the swollen hydrated sample. This is a remarkable property for many applications when the insoluble fiber needs to be dispersed evenly through simple rehydration such that no mechanical force, e.g., high pressure homogenization, sonication, heating or microwaving, is required.

Sample No. 1 was better than other samples in this example also in terms of water absorption capacity (measured by weight), volume expansion and the ability to maintain well-defined shape after prolonged incubation in the aqueous state at both pH 7.0 and pH 1.0. Moreover, the insoluble fiber in Sample 1 became fully spread out and evenly distributed throughout the sample, as observed under the polarized light in FIG. 2B.

Figure 2A:
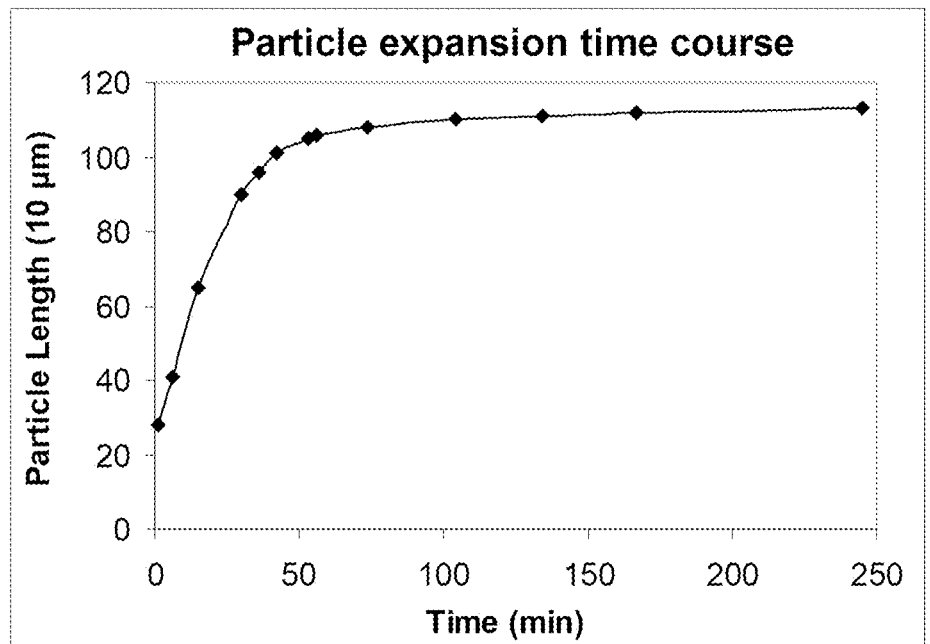
FIGS. 2A-2B show the kinetics of water absorption and volume expansion of Sample No. 1 over a period of 4 hours.
Figure 2B:
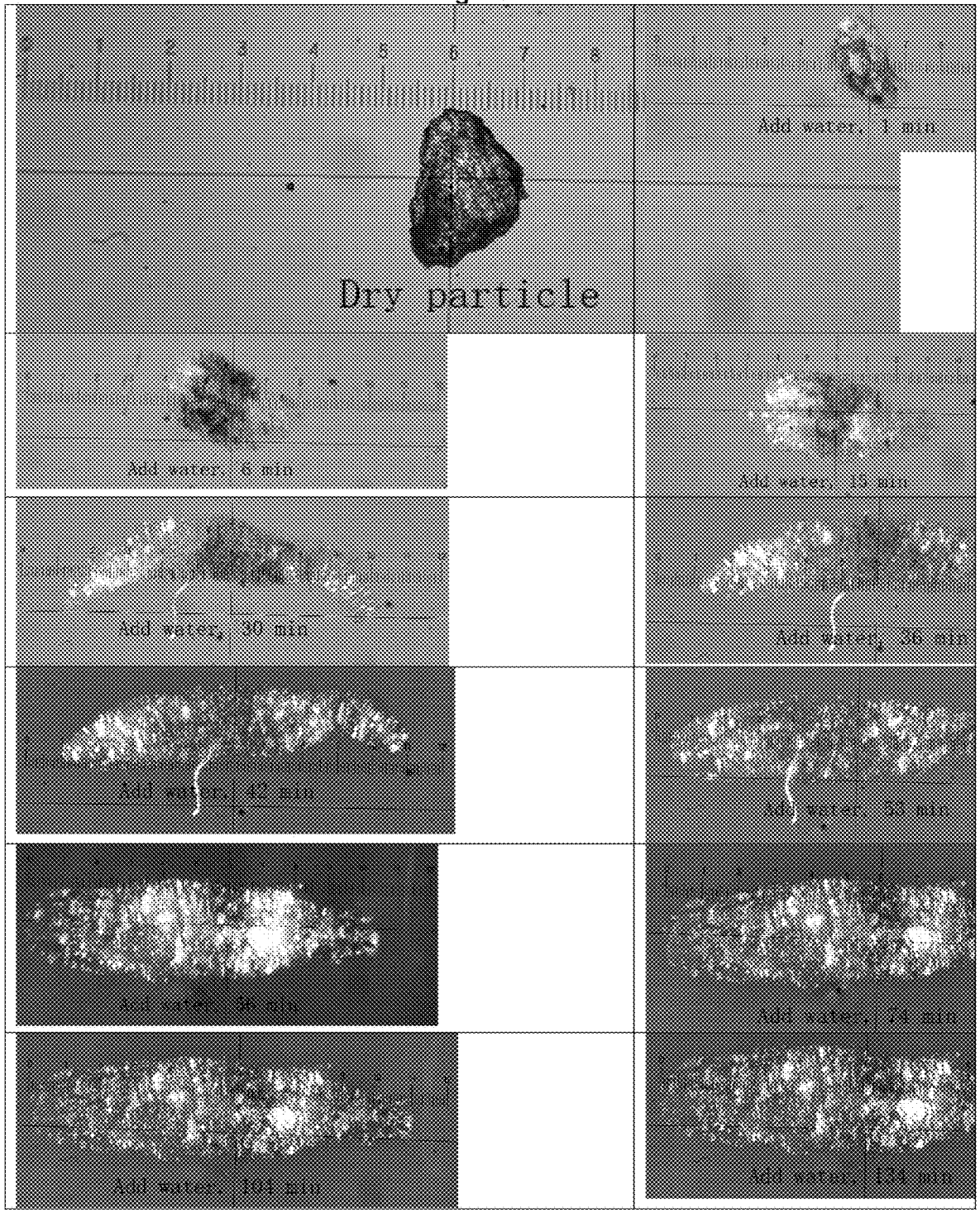

Water absorption and volume expansion kinetics: Sample No. 1 was further analyzed for its water absorption and volume expansion time course. A single particle of Sample No. 1 was soaked in deionized water (pH 7.0) for over four hours and the status of the particle in water was recorded in pictures by Leica MZ125 at different time points (FIG. 2B) and plot against each time point (FIG. 2A). The volume expanded about 30 times (about 2 (length)×2 (width)×7.5 (height)=30 fold) and reached 90% max volume in less than 30 minutes.

Figure 3:
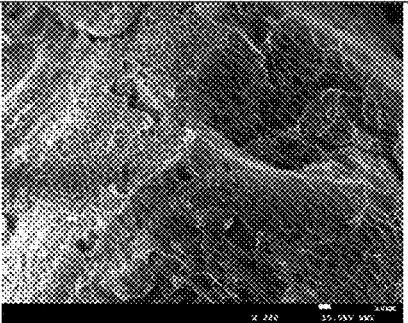
FIG. 3 shows the SEM images of Sample Nos 1-5 swelled in water at pH 7.0 and in 0.1 M HCl at pH 1.0. Two different perspectives for each sample under each pH condition are shown. Particles of Samples Nos 1-5 were placed in deionized water (pH=7) or 0.1 M HCl (pH=1) and fully absorbed and expanded for 24 hours. The swelled samples were quickly frozen in liquid nitrogen and lyophilized overnight. The lyophilized dry particles were spray-coated and analyzed by a JOEL JSM-7001 scanning electron microscope (SEM). The SEM images demonstrate that the superabsorbent materials formed porous structure in solution, explaining their high water retention capability, and the extensive inter-connected network structure explains their shape stability at neutral or acidic pH conditions. These features are most pronounced in sample No. 1, which exhibited best water absorption function, volume expansion, and shape stability.
Figure 3:
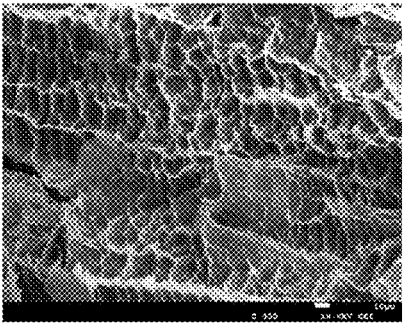
Figure 3:
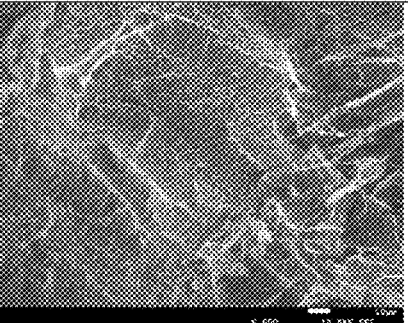
Figure 3:
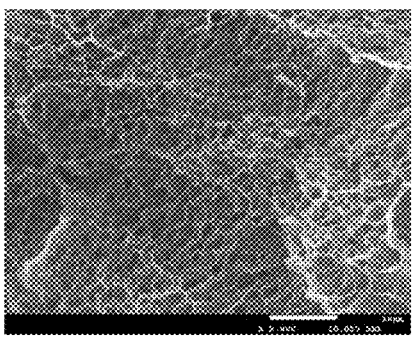
Figure 3:
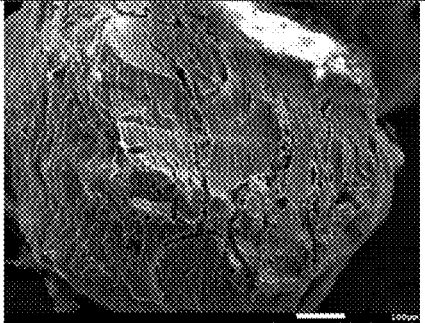
Figure 3:
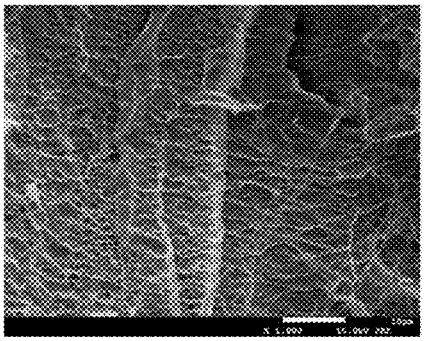
Figure 3:
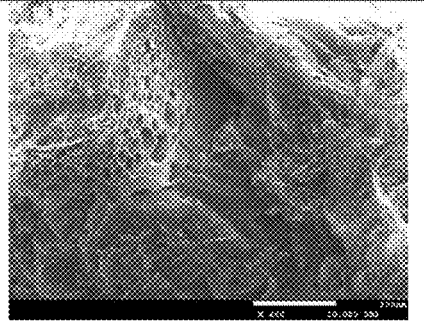
Figure 3:
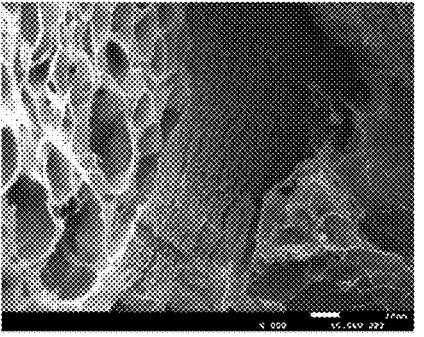
Figure 3:
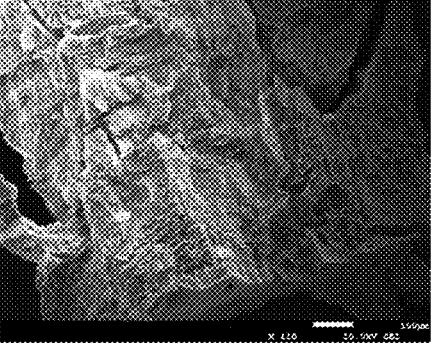
Figure 3:
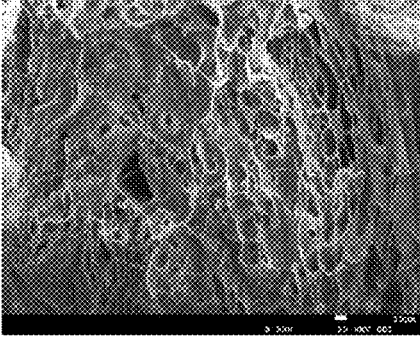
Figure 3:
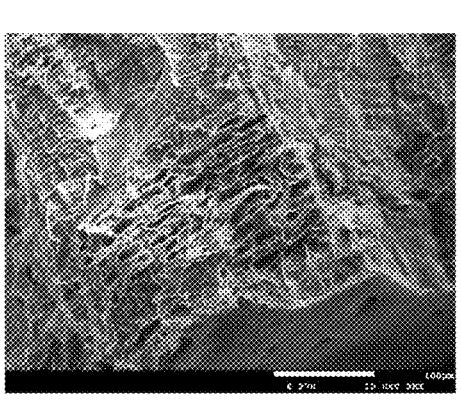
Figure 3:
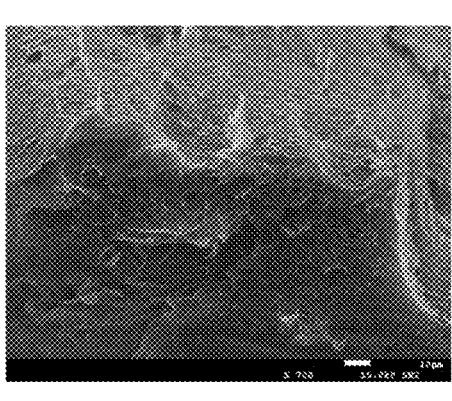
Figure 3:
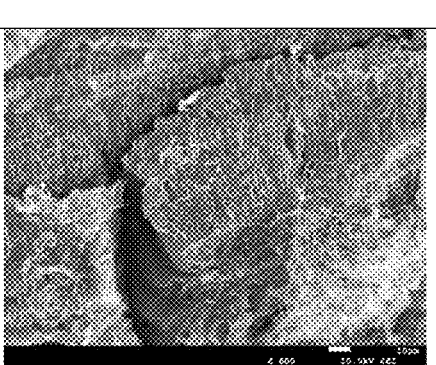
Figure 3:
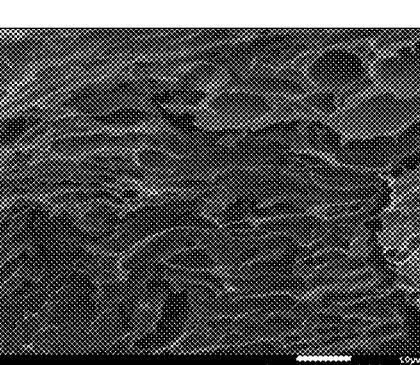
Figure 3:
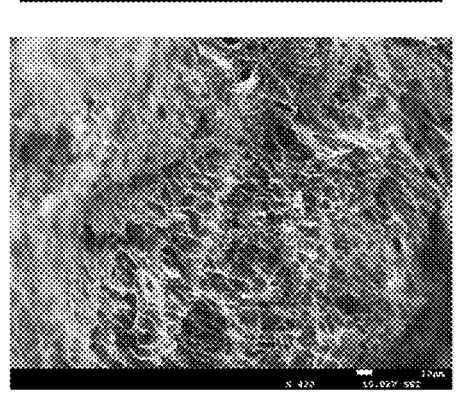
Figure 3:
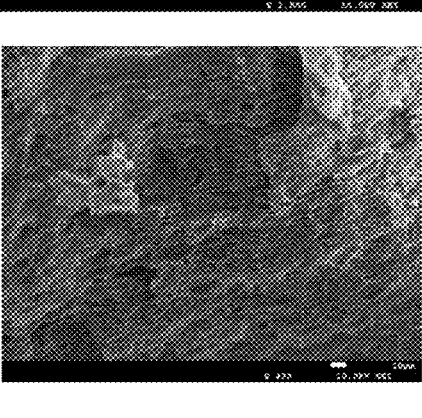
Figure 3:
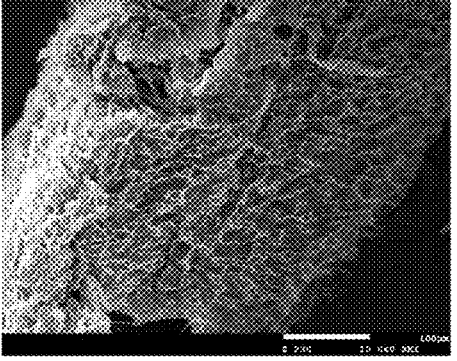
Figure 3:
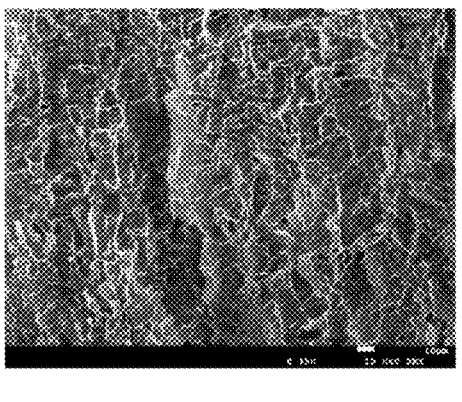
Figure 7:
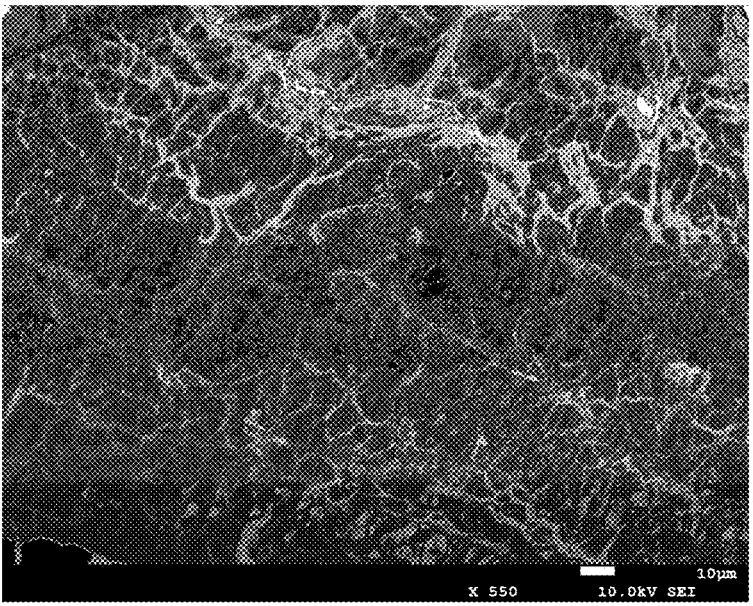
FIG. 7 shows additional representative SEM images of Samples Nos. 1, 6, 10, 12, 13, and 15 to further illustrate the porous network structures.
Figure 7:
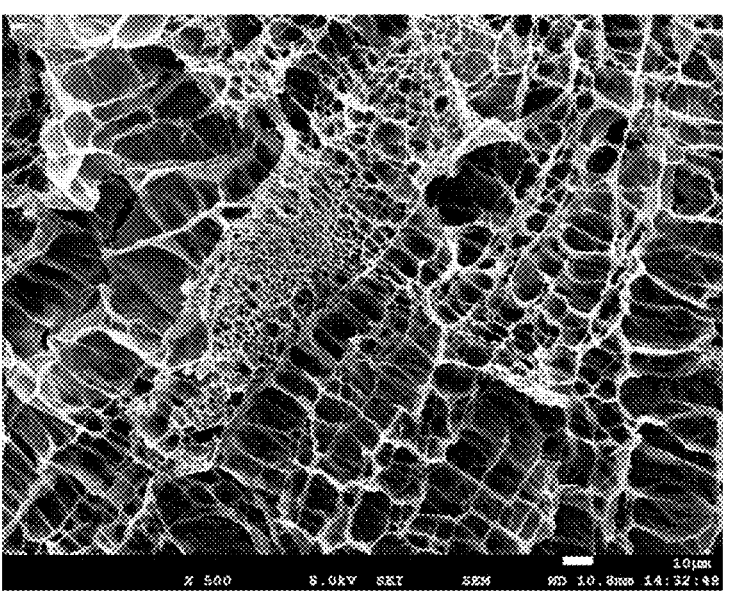
Figure 7:
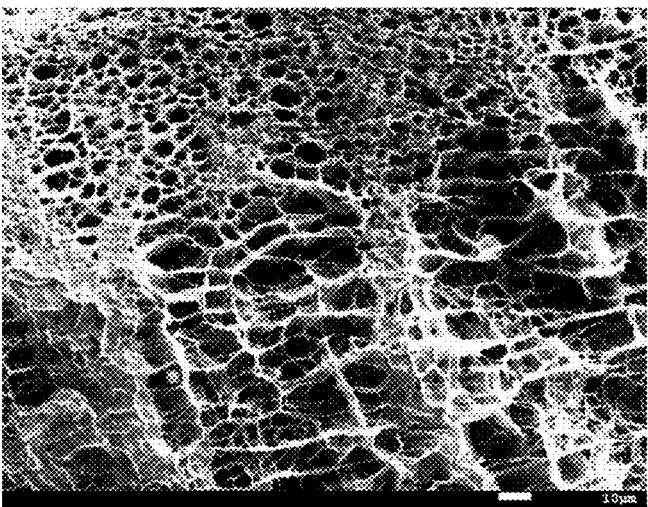
Figure 7:
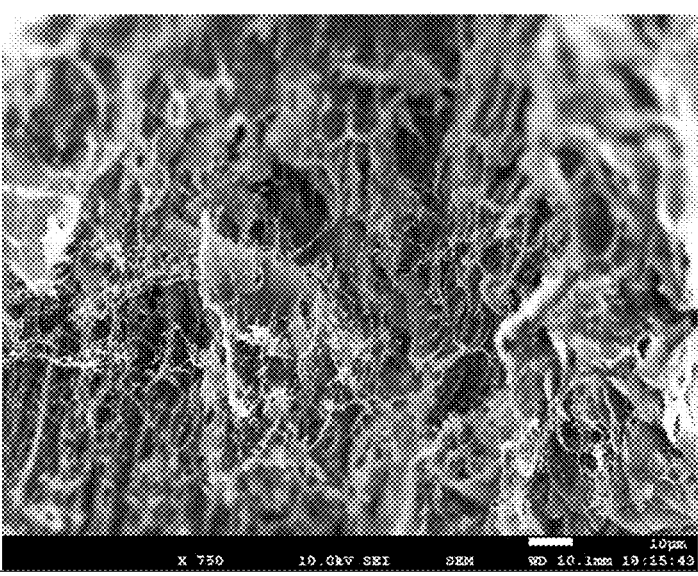
Figure 7:
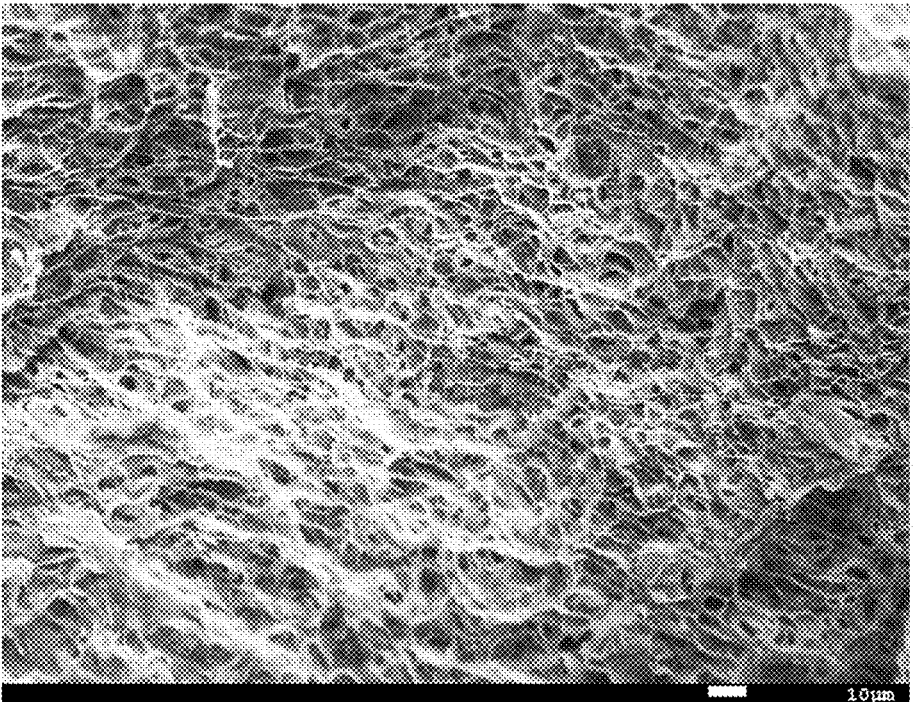
Figure 7:
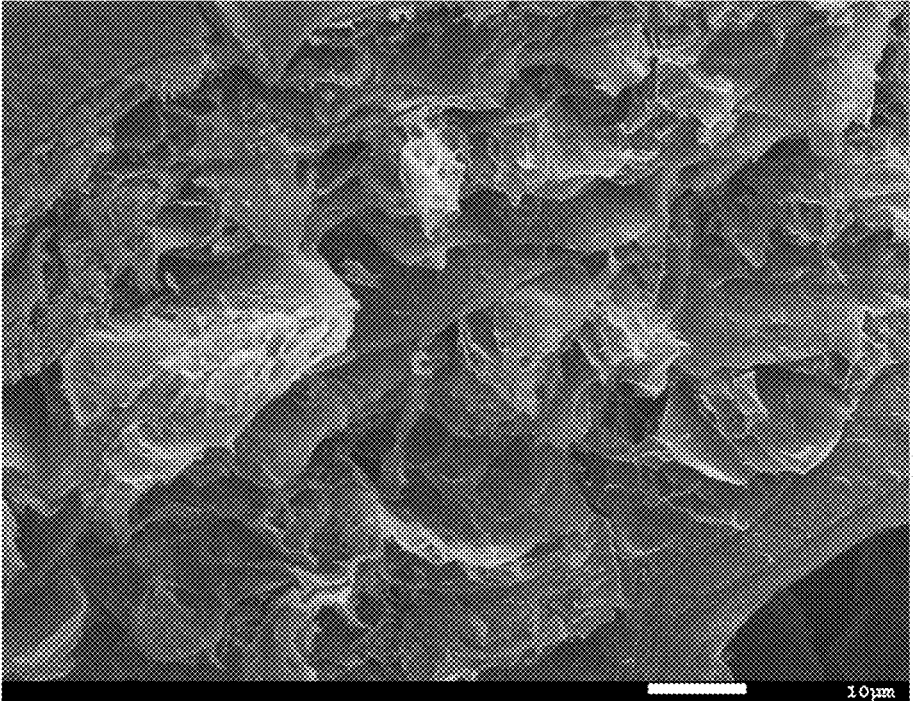

Analysis by scanning electron microscope (SEM): Particles of Sample Nos. 1-5 were soaked in deionized water at pH 7.0 for 24 hours to allow full absorption and expansion. The water-swelled samples were quickly frozen in liquid nitrogen and lyophilized overnight. The lyophilized dry particles were spray-coated and analyzed by scanning electron microscope (SEM). The representative SEM images of Sample Nos. 1-5 swelled in water and in HCl are shown in FIG. 3. FIG. 7 shows another representative SEM image of Sample No. 1 in water.

As shown in FIGS. 3 and 7, after rehydration, the superabsorbent materials formed and retained its porous network structure in solution, which advantageously may contribute to its superior volume expansion and high water absorption capabilities. Also, the extensive inter-connected network structure may contribute to their shape stability. These features are most pronounced in Sample No. 1, which displayed best water absorption function, volume expansion, and shape stability among Sample Nos 1-5 in this example.

In particular, as shown in FIG. 7, the representative image of Sample No. 1 shows a porous network structure characterized by a plurality of pores organized in a highly uniform pattern, and such pores are densely-populated as characterized by a two-dimension pore density in a range of 1 per 100 $\mu m^2$ to 500 per 100 $\mu m^2$. The pores exhibited an average diameter size of 3 $\mu m$ to 15 $\mu m$. Small pores of tens of nanometers to 1 $\mu m$ were sometimes observed. The pores were surrounded by sheet-like and/or fiber-like structures and densely arranged. The pores exhibit hexagonal shapes, pentagonal shapes, circular shapes, and rectangular shapes. A pore can be interconnected with another pore via one or more channels. The densely-populated pores are organized in a highly uniform pattern resembling a honey comb pattern.

Example 2

This example demonstrates preparation and characterization of additional superabsorbent materials. Sample Nos 6-8 were prepared by varying the ingredients and concentrations of Sample 1 in an effort to further optimize the features of Sample 1. The ingredients of each sample are disclosed in Table 2 below. The seaweed composite material from *Gracilaria* was obtained as described herein and in PCT Application No. PCT/US2020/070160, filed on Jun. 19, 2020 and published as WO2020/257825 on Dec. 24, 2020 (which is herein incorporated in its entirety by reference) (Sample A-2), and has about 29.4% insoluble fiber and about 45.7% soluble fiber. The seaweed composite material from *Eucheuma* was obtained as described herein and in PCT Application No. PCT/US2020/070161, filed on Jun. 19, 2020 and published as WO2020/257826 on Dec. 24, 2020 (which is herein incorporated in its entirety by reference) (Sample L), has about 39.5% insoluble fiber and about 26.0% soluble fiber.

TABLE 2

| Sample No | Ingredients and Concentrations (w/w) | Total water-soluble polysaccharide to total insoluble fiber | WRC at pH 7.0 | WRC at pH 1.0 |
| --- | --- | --- | --- | --- |
| 6 | Seaweed composite material from *Gracilaria* (0.2%), seaweed composite material from *Eucheuma* (0.5%), and Konjac Gum (0.5%) | 2.82 | 32.1 | 27.9 |
| 7 | Seaweed composite material from *Gracilaria* (0.3%), Konjac Gum (0.3%), and xanthan gum (0.3%) | 8.36 | 84.8 | 26.9 |
| 8 | Seaweed composite material from *Gracilaria* (0.3%), Locust bean gum (0.3%), and xanthan gum (0.3%) | 8.36 | 52.3 | 19.3 |

Sample preparation: The ingredients were added to water at concentrations as detailed in Table 2, and the samples were prepared following the same protocol as disclosed in Example 1.

Sample Nos 9-11 were prepared by varying the ingredients and concentrations of Sample 5 which included soybean fiber. The ingredients of each sample are disclosed in Table 3 below. The soybean fiber was obtained as described herein and in PCT Application No. PCT/US2021/014388, filed on Jan. 21, 2021 (which is incorporated herein in its entirety by reference) (Sample D), and has about 76.1% insoluble fiber and about 12.2% soluble fiber.

TABLE 3

| Sample No | Ingredients and Concentrations (w/w) | Total water-soluble polysaccharide to total insoluble fiber | WRC at pH 7.0 | WRC at pH 1.0 |
| --- | --- | --- | --- | --- |
| 9 | Agar (0.6%), Konjac Gum (0.3%), carrageenan (0.3%) and soybean fiber (0.8%) | 2.13 | 25.3 | 18.8 |
| 10 | Agar (0.4%), Konjac Gum (0.4%), carrageenan (0.4%), and soybean fiber (0.8%) | 2.13 | 38.4 | 23.1 |
| 11 | Agar (0.2%), Konjac Gum (0.5%), carrageenan (0.5%), and soybean fiber (0.8%) | 2.13 | 46.0 | 27.1 |

Sample preparation: Agar, konjac flour and carrageenan were added to 70% water used to prepare the gel (the concentrations in Table 3 refer to final concentration after combining with 70% soluble ingredients and 30% insoluble ingredient), stirred and dispersed uniformly at high speed, and heated and boiled for 5 minutes to fully dissolve the water-soluble ingredients. Soybean fiber was added to 30% water used to prepare the gel, heated to above 60° C., and homogenized under a pressure of 10-50 MPa. The homogenized soybean fiber material was added to the colloidal solution containing dissolved agar, konjac, and carrageenan, stirred and mixed uniformly, and the mixture was kept above 50° C. to prevent gel formation during the mixing process. The liquid was cooled to 20-25° C. and left to stand for more than 6 hours to form a gel. The gel was stored below −10° C. for 24 hours to completely freeze the gel. The frozen gel was thawed in air at 20-30° C. or immersed in 20-30° C. water. Subsequently, the thawed gel was filtered or centrifuged and dehydrated, followed by drying with hot air at 50-60° C. to reach a moisture content of less than about 15%.

Sample Nos 12 and 13 were prepared using the seaweed composite material from *Gracilaria*, with and without soybean fiber, respectively. The ingredients of each sample are disclosed in Table 4. The seaweed composite material from *Gracilaria* was obtained as described herein and in PCT Application No. PCT/US2020/070160, filed on Jun. 19, 2020 and published as WO2020/257825 on Dec. 24, 2020 (which is herein incorporated in its entirety by reference) (Sample A-2), and has about 29.4% insoluble fiber and about 45.7% soluble fiber. The soybean fiber was obtained as described herein and in PCT Application No. PCT/US2021/014388, filed on Jan. 21, 2021 (which is incorporated herein in its entirety by reference) (Sample D), and has about 76.1% insoluble fiber and about 12.2% soluble fiber.

TABLE 4

| Sample No | Ingredients and Concentrations (w/w) | Total water-soluble polysaccharide to total insoluble fiber | WRC at pH 7.0 | WRC at pH 1.0 |
| --- | --- | --- | --- | --- |
| 12 | Seaweed composite material from *Gracilaria* (1%) | 1.55 | 11.8 | 10 |
| 13 | Seaweed composite material from *Gracilaria* (1%), and soybean fiber (1%) | 0.55 | 11.5 | 9.7 |

Sample preparation: Sample No. 12 was prepared by following the protocol of preparing Sample Nos 6-8, and Sample No. 13 was prepared by following the protocol of preparing Sample Nos 9-11, both followed the thawing dry procedure under the atmospheric pressure. Sample Nos 14-16 were prepared using the seaweed composite material from *Gracilaria*, soybean fiber, or both, using a freeze dry procedure. The ingredients of each sample are disclosed in Table 5. The seaweed composite material from *Gracilaria* was obtained as described herein and in PCT Application No. PCT/US2020/070160, filed on Jun. 19, 2020 and published as WO2020/257825 on Dec. 24, 2020 (which is herein incorporated in its entirety by reference) (Sample A-2), and has about 29.4% insoluble fiber and about 45.7% soluble fiber. The soybean fiber was obtained as described herein and in PCT Application No. PCT/US2021/014388, filed on Jan. 21, 2021 (which is incorporated herein in its entirety by reference) (Sample D), and has about 76.1% insoluble fiber and about 12.2% soluble fiber.

TABLE 5

| Sample No | Ingredients and Concentrations (w/w) | Total water-soluble polysaccharide to total insoluble fiber | WRC at pH 7.0 | WRC at pH 1.0 |
| --- | --- | --- | --- | --- |
| 14 | Seaweed composite material from *Gracilaria* (1%) | 1.55 | 27.3 | 25.7 |
| 15 | Seaweed composite material from *Gracilaria* (1%), and soybean fiber (1%) | 0.55 | 21 | 17.8 |
| 16 | Soybean fiber (2%) | 0.16 | 23.7 | 14.9 |

Sample preparation: For Sample No. 14, the seaweed composite material from *Gracilaria* was added to water at a concentration as detailed in Table 5, stirred and dispersed uniformly at high speed, and heated and boiled for 5 minutes to fully dissolve the water-soluble ingredients. For Sample No. 15, the seaweed composite material from *Gracilaria* was added to 50% water used to prepare the gel, stirred and dispersed uniformly at high speed, and heated and boiled for 5 minutes to fully dissolve the water-soluble ingredients. The soybean fiber was added to 50% water used to prepare the gel, heated to above 60° C., and homogenized under a pressure of 10-50 MPa. The homogenized soybean fiber was then added to the colloidal solution containing the seaweed composite material at a ratio of 1:1 (v/v), such that the final concentration of each ingredient is as detailed in Table 5. The combined samples were stirred and mixed uniformly, and the mixture was kept above 50° C. to prevent gel formation during the mixing process. For Sample No. 16, the soybean fiber was added to water, at a concentration as detailed in Table 5, heated to above 60° C., and homogenized under a pressure of 10-50 MPa.

The liquid prepared above for each sample was cooled to 20-25° C. and left to stand for more than 6 hours to form a gel. The gel was stored below −10° C. for 24 hours to completely freeze the gel. The frozen gel was dehydrated and dried in a vacuum freeze dryer to a moisture content of 15% or less at −20° C. to −40° C.

Figure 4:
FIG. 4 shows the light microscope images of Sample Nos. 6-16 of the superabsorbent materials before and after soaking in deionized water and 0.1 M HCl. The smallest division of the scale in the figure is 10 μm.
Figure 4:
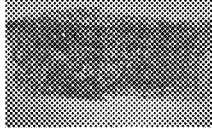
Figure 4:
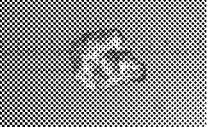
Figure 4:
Figure 4:
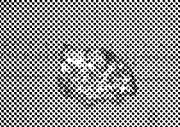
Figure 4:
Figure 4:
Figure 4:
Figure 4:
Figure 4:
Figure 4:
Figure 4:
Figure 4:
Figure 4:
Figure 4:
Figure 4:
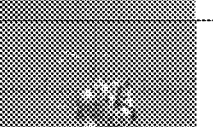
Figure 4:
Figure 4:
Figure 4:
Figure 4:
Figure 4:
Figure 4:
Figure 4:
Figure 4:
Figure 4:
Figure 4:
Figure 4:
Figure 4:
Figure 4:
Figure 4:
Figure 4:
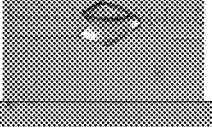
Figure 4:
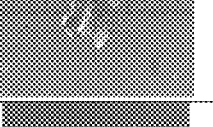
Figure 4:
Figure 4:
Figure 4:
Figure 4:
Figure 4:
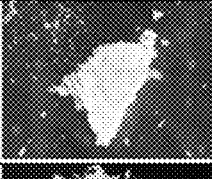

Volume expansion and structure stability analysis: Particles of Sample Nos 6-16 were soaked in deionized water (ddw) or 0.1 M HCl solution for over 24 hours. The images of the samples before and after rehydration were taken using Leica MZ 125 microscope and shown in FIG. 4. Table 6 below summarizes the observations of each of Sample Nos 6-16 after rehydration in water or 0.1 M HCl.

TABLE 6

| Sample No. | Rehydration in water | Rehydration in 0.1M HCl |
| --- | --- | --- |
| 6 | High volume expansion with well-defined structure, insoluble fiber expanded and evenly distributed as shown by polarized light microscope image | Relatively good volume expansion with well-defined structure. |
| 7 | High volume expansion with well-defined structure, insoluble fiber expanded and evenly distributed as shown by polarized light microscope image | Relatively good volume expansion with well-defined structure. |
| 8 | High volume expansion but resulting in poor structure stability. The hydrated form became disintegrated, the insoluble fiber also seemed to be unevenly distributed in the hydrated state. These observations suggest that this particular combination of soluble polysaccharides and insoluble fibers may not form a true composite matter with a uniform structure, but rather a loose mixture wherein each component absorbed water and expanded independently, resulting in the disintegration and uneven insoluble fiber distribution. | Moderately good volume expansion, but disintegrated to a lesser degree compared to the same sample when rehydrated in water at pH 7.0, probably due to less expansion. |
| 9 | High volume expansion with good structure stability, insoluble fiber expanded and evenly distributed as shown by polarized light microscope image, but unlike composite materials from seaweed, where the natural seaweed fiber showed as long fiber and arranged in roughly parallel orientation, the soybean fiber added to Sample No. 9 showed as discrete particles. | Sample No. 9 had good structure stability at pH 7.0 but seemed to have low structure stability at pH 1.0. |
| 10 | High volume expansion, but the expanded structure appeared to be less stable, and arranged in a loosely bound manner and some particles broke apart into segments. | Particle showed moderate expansion. More particles broke apart at the lower pH. |

TABLE 6-continued

| Sample No. | Rehydration in water | Rehydration in 0.1M HCl |
|---|---|---|
| 11 | High volume expansion, the expanded structure appeared to be ordered but it broke down into sections. Overall this sample appeared to be similar to Sample No. 10. | Particle showed relatively good volume expansion, and the expanded structure also showed some disintegration, but to a lesser degree compared with the same sample rehydrated in water. |
| 12 | Poor expansion with a tight structure at both pH 7.0 and pH 1.0. | Limited expansion with a tight structure. |
| 13 | Similar to Sample No. 12, poor expansion with a tight structure at both pH 7.0 and pH 1.0. | Similar to Sample No. 12, limited expansion with a tight structure. |
| 14 | Poor volume expansion at both pH 7.0 and pH 1.0. The particle with flaky layered structure did not show any significant volume expansion after soaking in water for over 24 hours. The sample showed gelling after rehydration. | Particle showed no expansion after soaking in 0.1M HCl for over 24 hours. The sample showed gelling after rehydration. |
| 15 | Poor expansion at both pH 7.0 and pH 1.0. The original powdery particles soaked in water had no visible volume expansion. The sample showed gelling after rehydration. | Particle showed no expansion after soaking in 0.1M HCl for over 24 hours. The sample showed gelling after rehydration. |
| 16 | Similar to Sample No. 15 but the powder was finer. The original conglomerate of powdery particles dispersed randomly after being soaked in water for a period of time with poor volume expansion. The sample did not show gelling after rehydration. | Similar to Sample No. 15 but the powder was finer which did not exhibit expansion in 0.1M HCl. The sample did not show gelling after rehydration. |

In general, the volume expansion of these samples when rehydrated in 0.1 M HCl was less than when rehydrated in water at pH 7.0. Some samples, which showed disintegration upon rehydration at pH 7.0, seemed to be less disintegrated upon rehydration at pH 1.0. However, this observation could be due to the fact that the samples had less volume expansion at pH 1.0.

Figure 5:
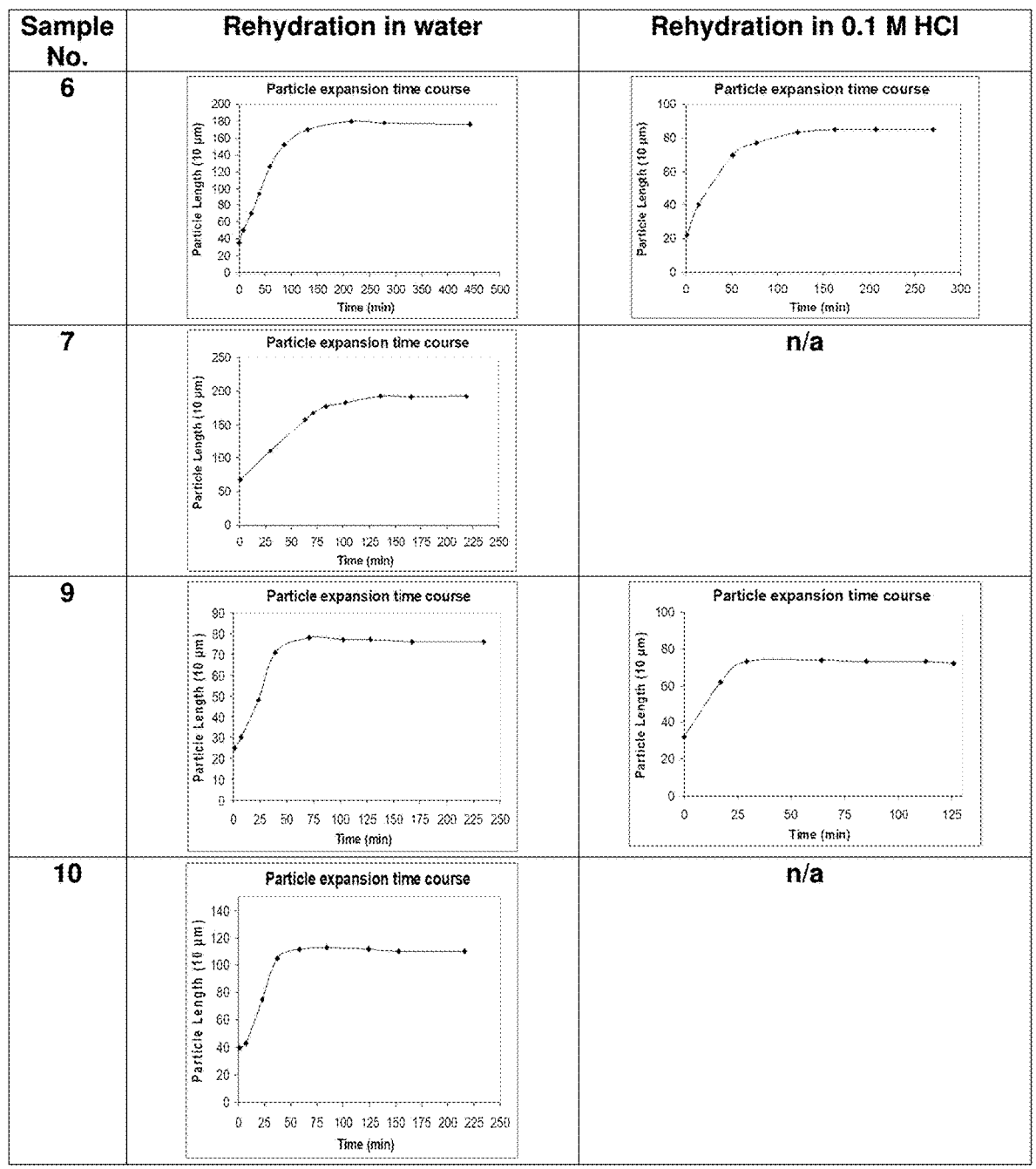
FIG. 5 shows the kinetics of water absorption and volume expansion of Sample Nos. 6, 7, 9, 10, and 11 after soaking in water or HCl for a period up to 4 hours.

Water absorption and volume expansion kinetics: Sample Nos. 6, 7, 9, 10, and 11 were further analyzed for their water absorption and volume expansion time course. A single particle of each sample was soaked in deionized water (pH 7.0) or 0.1 M HCl for over four hours and the status of the particle in water or HCl was recorded in pictures by Leica MZ125 at different time points (FIG. 5). In FIG. 5, "particle expansion" also refers to volume expansion. Generally, for Sample Nos. 6, 7, 9, 10, and 11 in FIG. 5, the volume expanded about 20-30 times and reached 90% max volume in less than 30-120 minutes. Notably, Samples 9, 10, and 11 reached about 90% max volume in about 30 minutes or less.

Figure 6:
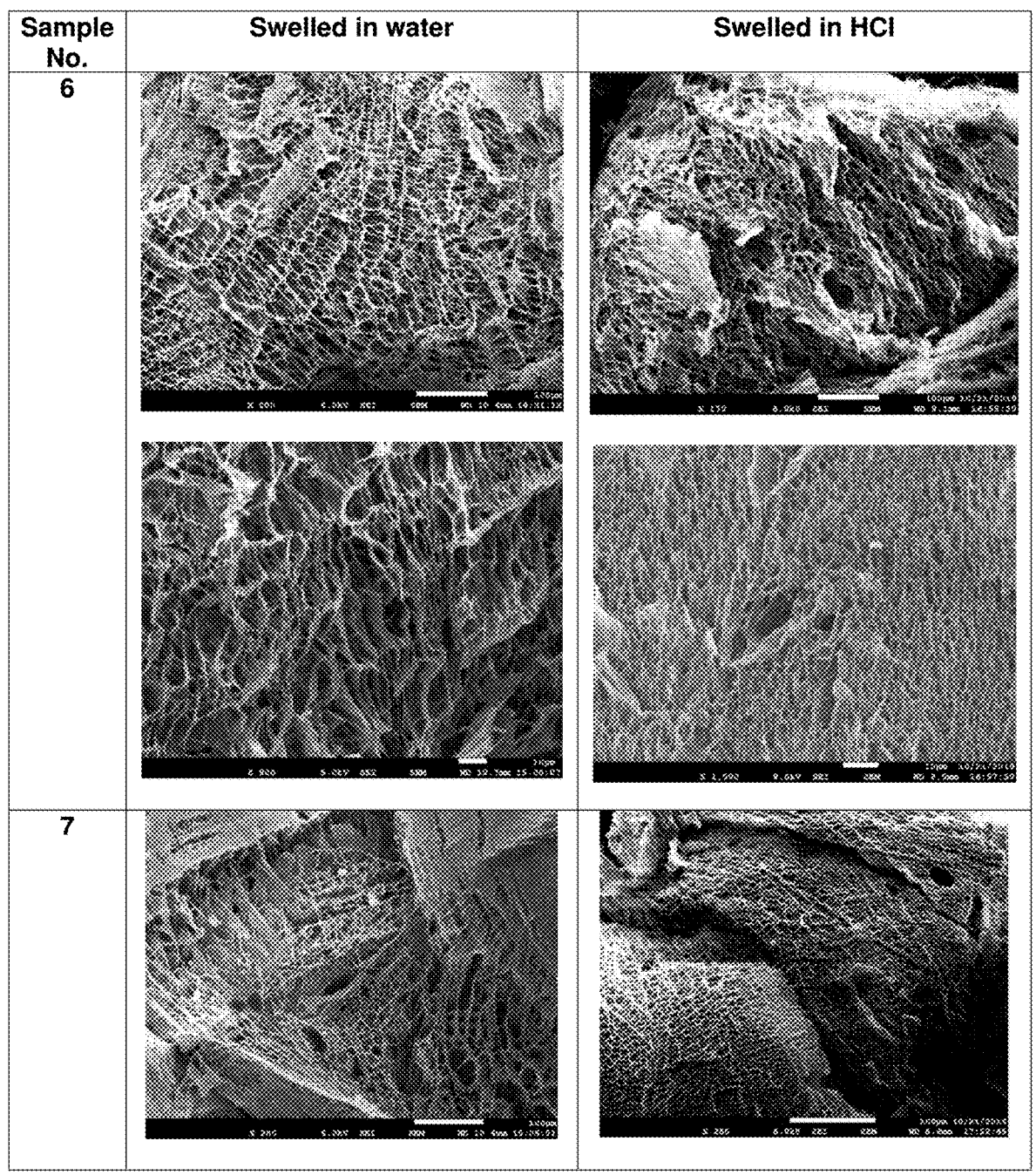
FIG. 6 shows the SEM images of Sample Nos 6-16 swelled in water at pH 7.0 and in 0.1 M HCl at pH 1.0. To capture the structural features in the hydrated state, thawing-dried samples from samples Nos 6-16 were soaked in deionized water (pH=7.0) or in 0.1 M HCl (pH=1.0) for more than 12 hours, flash frozen in liquid nitrogen, and lyophilized to dry, sputter coated with platinum and imaged on a JOEL JSM-7001 Scanning electron microscope. For each sample, a number of particles were imaged; images most representative of the observed structural features of a given sample are shown. For each sample under each pH condition, two different perspectives are shown.
Figure 6:
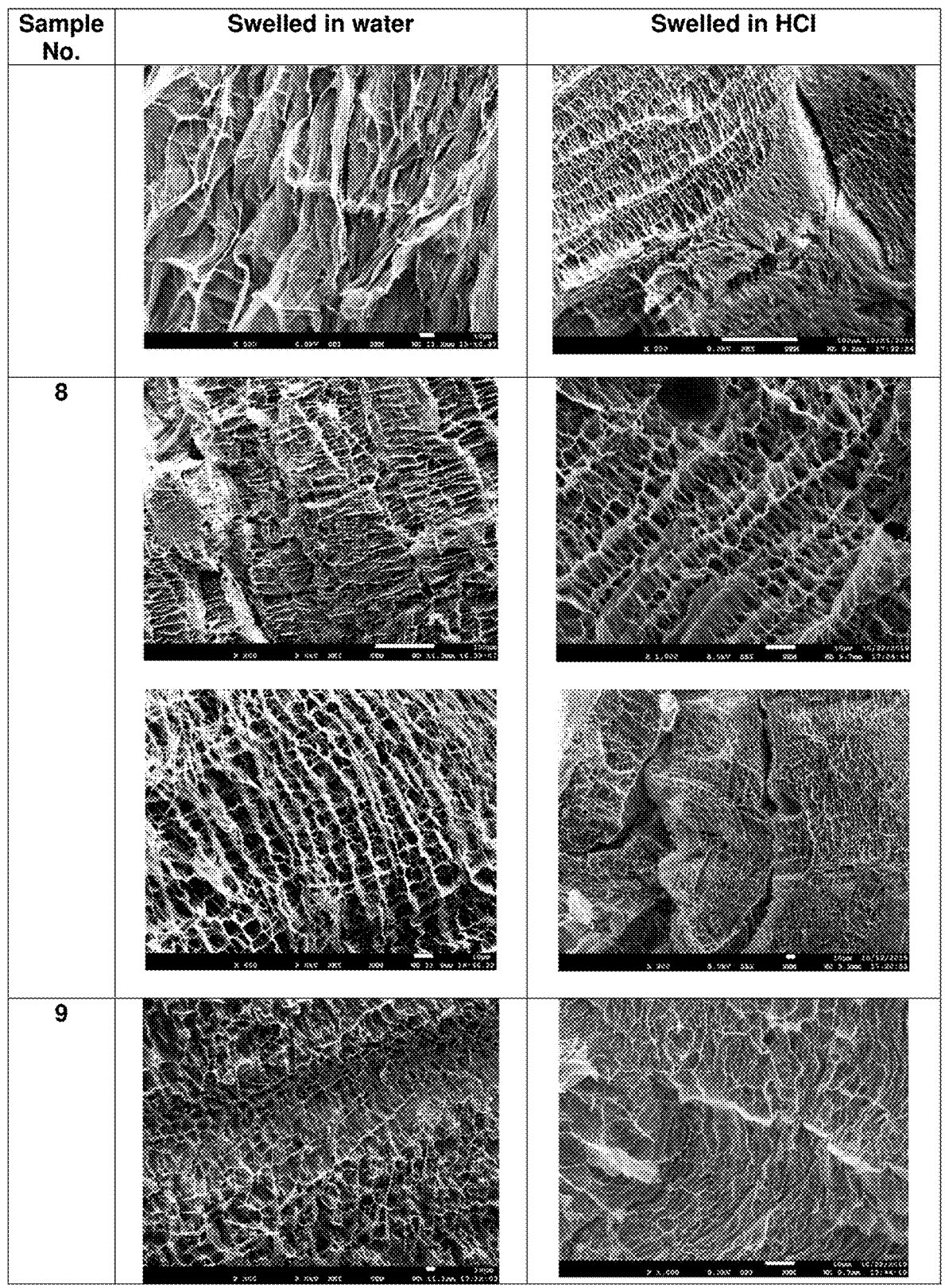
Figure 6:
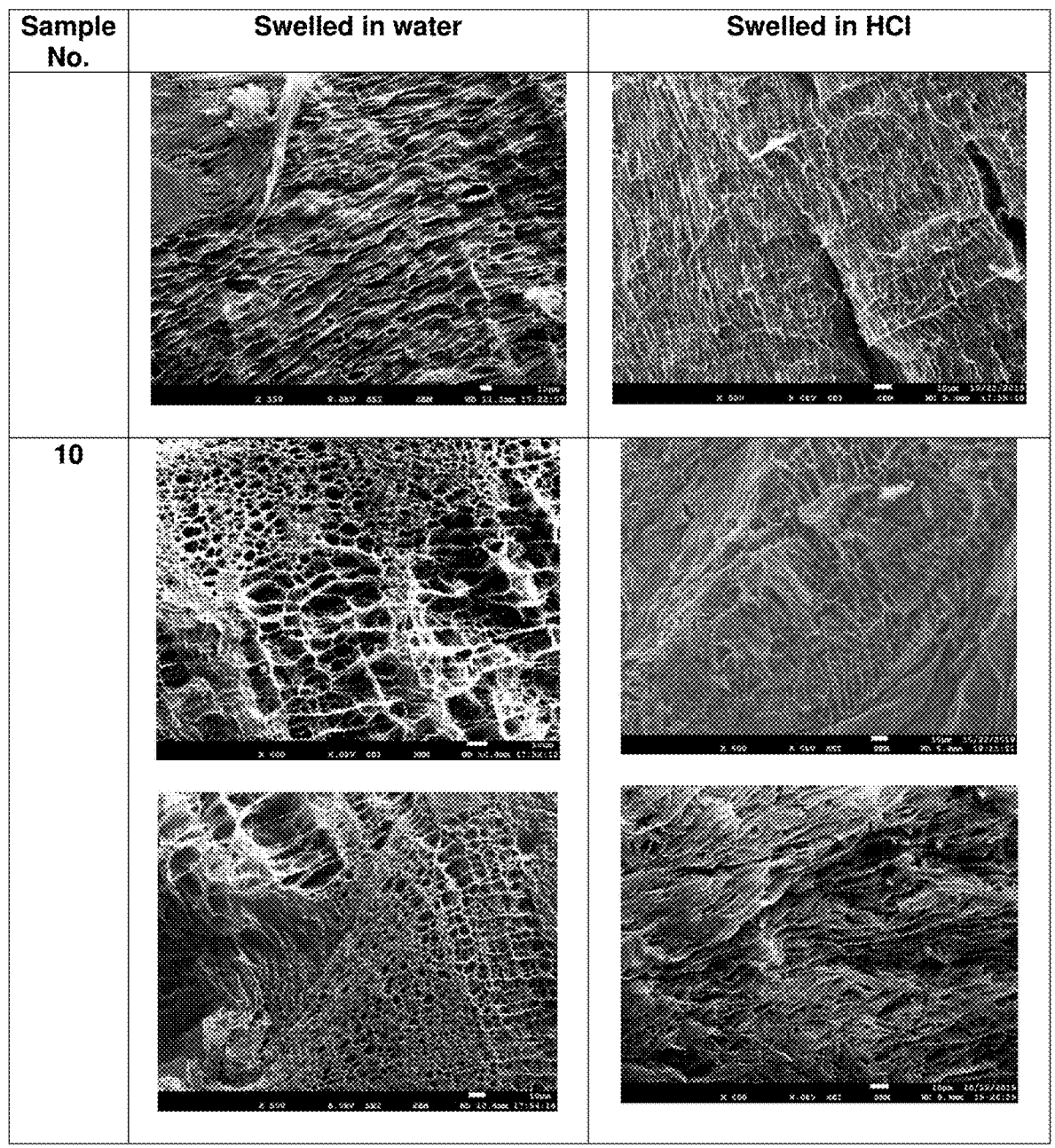
Figure 6:
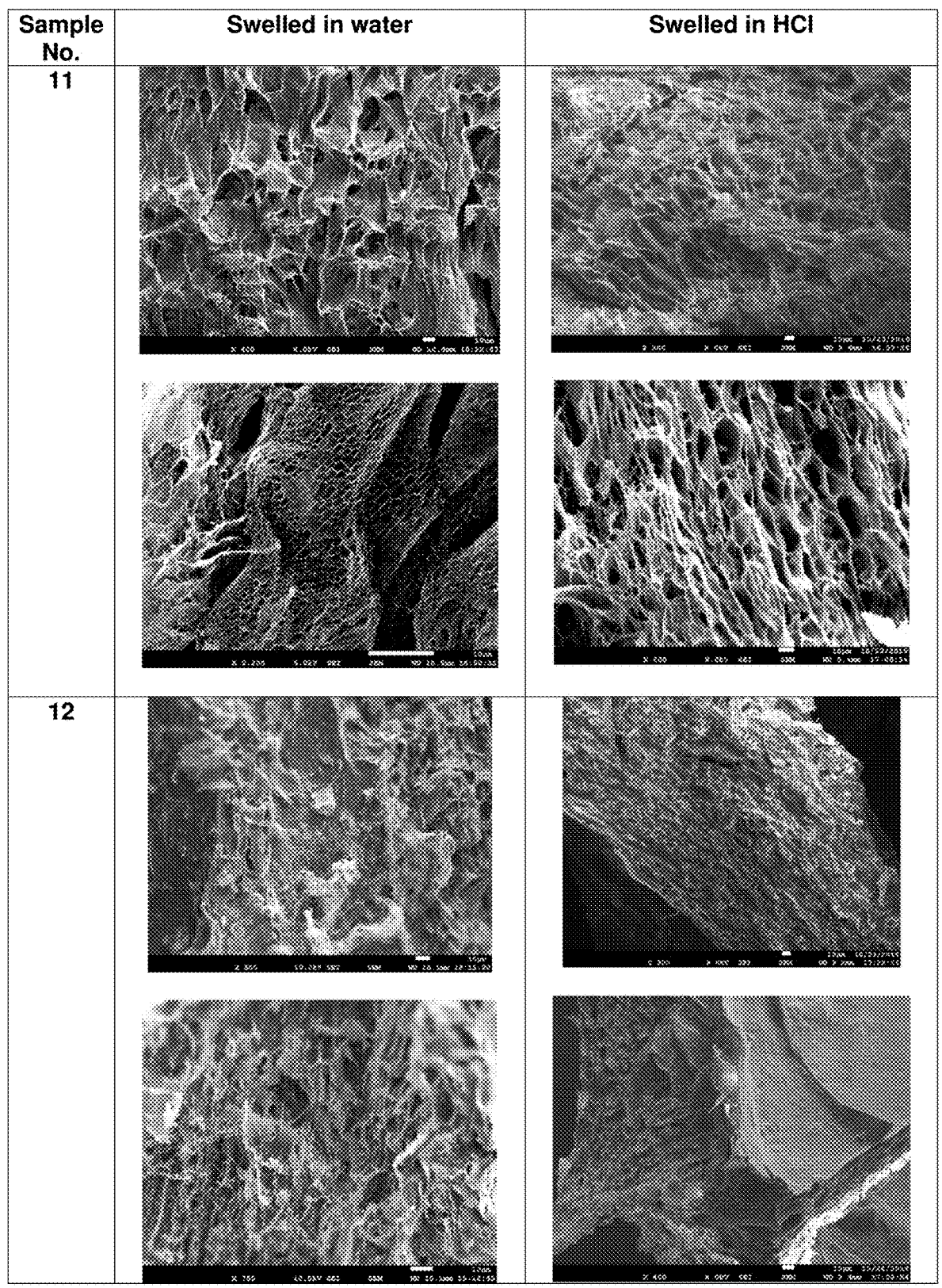
Figure 6:
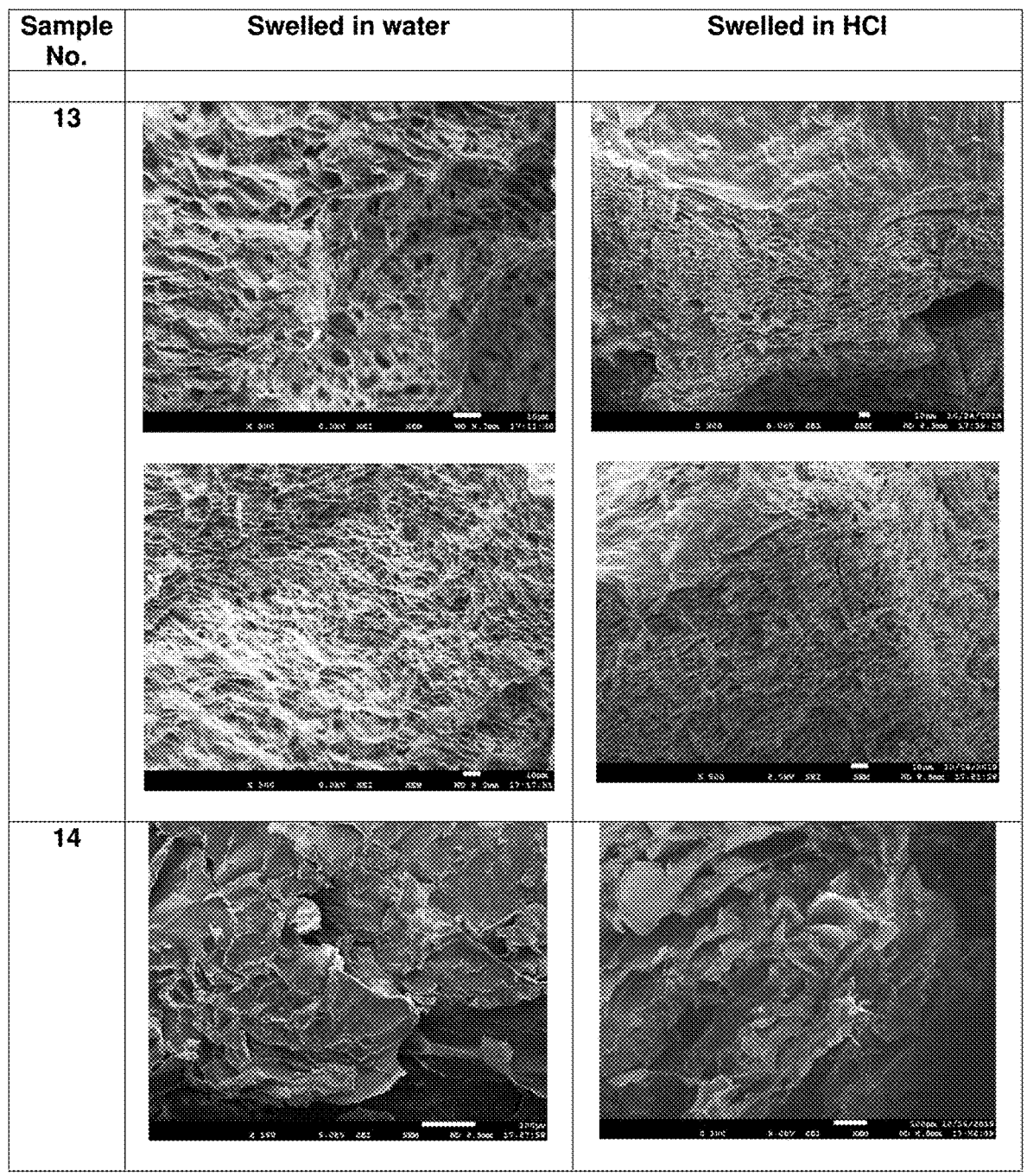
Figure 6:
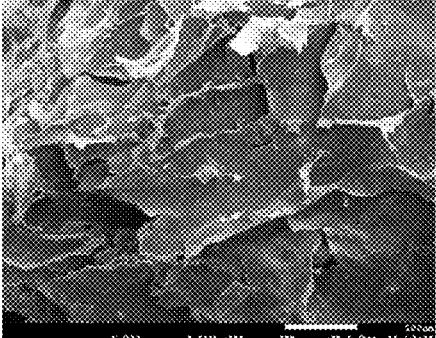
Figure 6:
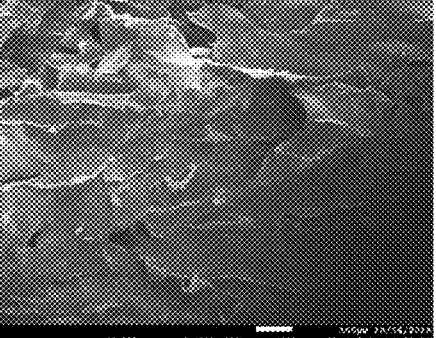
Figure 6:
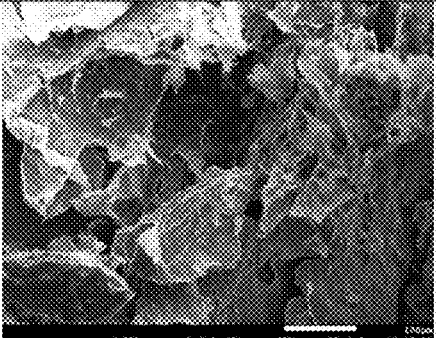
Figure 6:
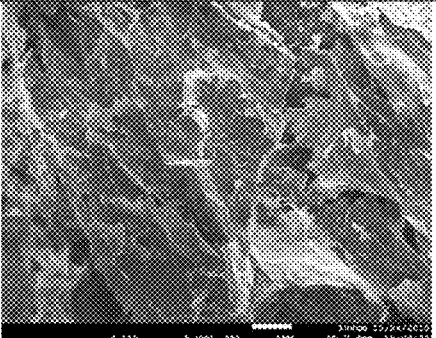
Figure 6:
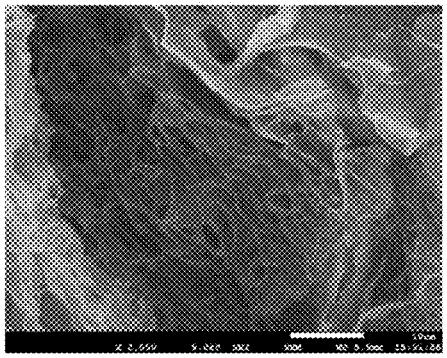
Figure 6:
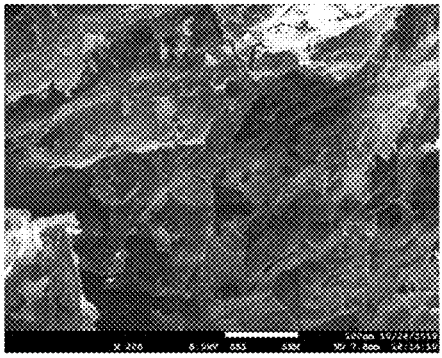
Figure 6:
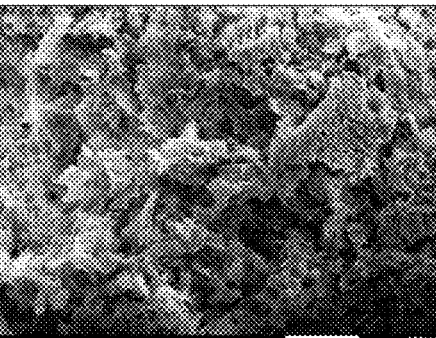
Figure 6:
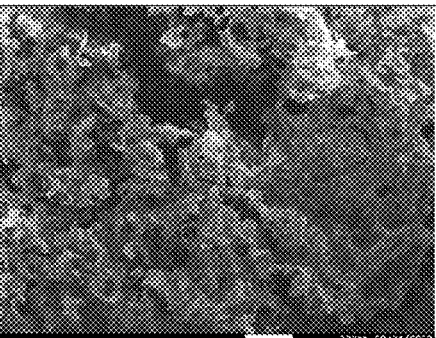
Figure 6:
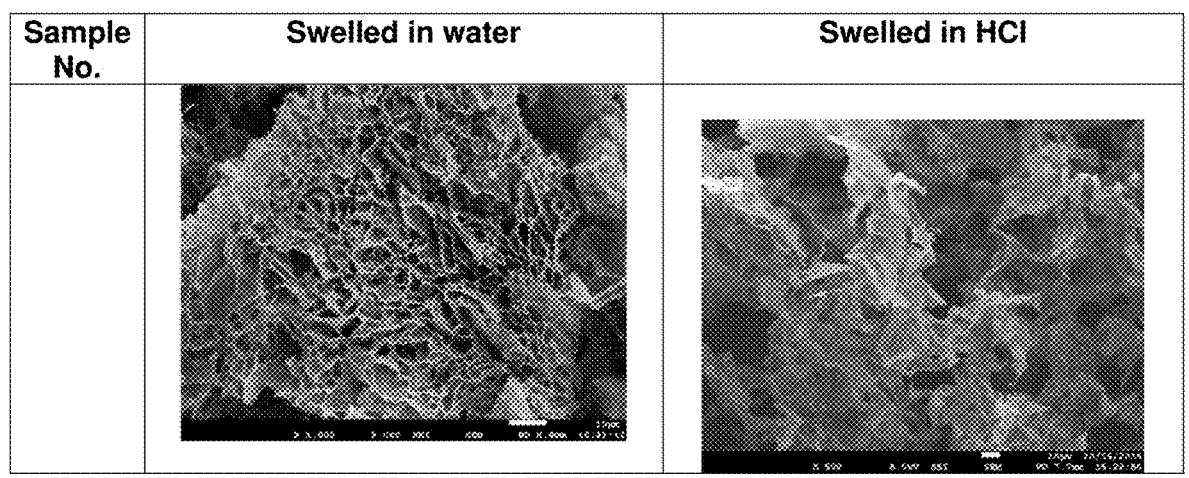

Analysis by scanning electron microscope (SEM): Particles of Sample Nos. 6-16 were soaked in deionized water at pH 7.0 or in 0.1 M HCL for over 12 hours to allow full absorption and expansion. The water-swelled samples were quickly frozen in liquid nitrogen and lyophilized overnight. The lyophilized dry particles were spray-coated and analyzed by scanning electron microscope (SEM). The SEM images of Samples 6-16 swelled in water and in HCl are shown in FIG. 6. For each sample, a number of particles were imaged but only images most representative of the observed structural features of a given sample are shown. Further, representative images of Sample Nos. 6, 7, 12, 13, and 15 are provided in FIG. 7.

As shown in FIG. 6, Sample Nos. 6 and 7 showed a characteristic porous network structure, with extensive network of connected pores. From different perspectives, the porous network structure showed honey comb pattern or layered large pores. For example, as shown in FIG. 7, the representative image of Sample No. 6 shows a porous network structure characterized by a plurality of pores organized in a highly uniform pattern, and such pores are densely-populated as characterized by a two-dimension pore density in a range of 1 per 100 $\mu m^2$ to 500 per 100 $\mu m^2$. The pores exhibited an average diameter size of 3 $\mu m$ to 15 $\mu m$. Small pores of tens of nanometers to 1 $\mu m$ were sometimes observed. The pores were surrounded by sheet-like and/or fiber-like structures and densely arranged. The pores exhibit hexagonal shapes, pentagonal shapes, circular shapes, and rectangular shapes. A pore can be interconnected with another pore via one or more channels.

Sample Nos. 8, 9, and 11 showed a porous structure but less organized patterns. Sample No. 10 showed somewhat porous/layered structure but less organized patterns. Sample No. 12 showed amorphous structure with no pore pattern. Sample No. 13 showed amorphous structure with some local pores but no pore pattern. Sample No. 14 showed a layered structure. Sample No. 15 showed an amorphous structure. Sample No. 16 showed an amorphous, puff structure with some local pore structures. Further, the representative SEM images of Sample Nos. 12, 13, and 15 exhibited less porous structure. Only layered structure or some local porous structure were observed. The pores exhibited an average diameter size of 2 $\mu m$ to 5 $\mu m$ and usually separated apart with each other. The two dimensional pore density was about less than 4 per 100 $\mu m^2$. The distance between layers was about 2 $\mu m$-5 $\mu m$.

Therefore, notably, samples having more gelling polysaccharides and gelling-compatible polysaccharides, such as Sample Nos. 6-7 (as well as Sample No. 1), exhibited a porous network structure and improved volume expansion. By contrast, samples having more insoluble fibers, such as Sample Nos. 12-16, exhibited layered, amorphous, fragment, shallow or small pore structure and poor volume expansion.

Comparing structural stability of the superabsorbent material after rehydration versus before freezing. As described, upon rehydration at room temperature, the disclosed superabsorbent material can rapidly expand in volume and maintain a well-defined structure, as characterized by its gel strength, for at least 24 hours or more. In this regard, the structural stability of the superabsorbent material before freezing and after rehydration (with DI water/pH 7, or acidic condition/pH 2), as measured by its gel strength, was studied. Specifically, Sample Nos. 1, 6, 7, and 14 were studied, as shown in Tables 7-8 below, and characterized by Texture analyzer, gel rupture force.

TABLE 7

Average Gel Strength Increase Percentage (%) before freezing and after rehydration with DI water (pH 7) at Room Temperature (RT).

| Sample No. | Ingredient and Concentration (w/w) | Average Gel strength before freezing (g) | Average Gel strength at 24 hours after rehydration with DI water (pH 7), RT. (g) | Average Gel strength Increase % |
|---|---|---|---|---|
| 1 | Seaweed composite material from *Gracilaria* (0.4%), seaweed composite material from *Eucheuma* (0.4%), and Konjac Gum (0.4%) | 347 ± 18 | 922 ± 391 | 166% |
| 6 | Seaweed composite material from *Gracilaria* (0.2%), seaweed composite material from *Eucheuma* (0.5%), and Konjac (0.5%) | 534 ± 35 | 1043 ± 186 | 95% |
| 7 | Seaweed composite material from *Gracilaria* (0.3%), Konjac Gum (0.3%), and xanthan gum (0.3%) | 487 ± 42 | 1066 ± 87 | 119% |
| 14 | Seaweed composite material from *Gracilaria* (1%) | 474 ± 14 | 1402 ± 479 | 196% |

Sample preparation for samples before freezing: For each Sample, the respective ingredients, as shown in Table 7, were added into deionized (DI) water and boiled for 5 minutes. Then resulting mixture was cooled at room temperature for 15 hours to form the gel. The gel was then cut into cube shape of 3*3*3 cm and measured by texture analyzer.

Sample preparation for samples rehydrated with DI water (pH 7) at RT: For each Sample, the respective ingredients, as shown in Table 7, were added into DI water and boiled for 5 minutes. Then the resulting mixture was cooled at room temperature for 15 hours to form the gel. The gel was then kept frozen at −5° C. for 48 hours before it was thawed under room temperature. It was then dehydrated to moisture level of about 10%. Cube shape gel pieces were taken at 3 cm*3 cm (it was 3 cm thick before freezing), the gel pieces were soaked in DI water (pH 7) at room temperature (about 20° C.) for 24 hours, then the gel strength was measured for each Sample.

Gel strength measurements: Gel strength measurements were conducted using Texture Analyzer (TA.XT plus, Stable Micro Systems Ltd) with probe P10.5. The gel strength measurement was carried out at compression speed of 0.3 mm/s and compression height of 15 mm. Gel rupture force was captured (unit: g). Three to six replicates were measured and average was taken.

Advantageously, as shown in Table 7, at 24 hours after rehydration with DI water (pH 7), the superabsorbent material exhibited a significantly higher gel strength than the gel formed before freezing. Specifically, Sample No. 1 had an average gel strength increase of 166%, Sample No. 6 was 95%, Sample No. 7 was 119%, and Sample No. 14 was 196%. The average gel strength increase percentage (%)= (Average gel strength after rehydration—Average gel strength before freezing)/Average gel strength before freezing. Therefore, this shows that when rehydrated in water, a stable hydrogel is formed and the strength is maintained and even improved for at least 24 hours or longer after rehydration. Advantageously, the incorporation of insoluble fibers in the soluble gelling polysaccharides enhances the gel network so that the superabsorbent material can significantly improve its gel strength in DI water for at least 24 hours or longer after rehydration.

In Table 8 below, the gel strengths of Sample Nos. 1, 6, 7, and 14 were further tested with rehydration in acidic condition (pH 2, HCl solution) to mimic gastric condition in the human body, and compared to the gel strength before freezing.

TABLE 8

Average Gel Strength Maintenance Percentage before freezing and after rehydration in acidic condition (pH 2, HCl solution) at RT.

| Sample No. | Ingredient and Concentration (w/w) | Average Gel strength before freezing (g) | Average Gel strength at 24 hours after rehydration in acidic solution (pH 2, HCl) at RT. (g) | Average Gel strength maintenance % |
|---|---|---|---|---|
| 1 | Seaweed composite material from *Gracilaria* (0.4%), seaweed composite material from *Eucheuma* (0.4%), and Konjac | 347 ± 18 | 302 ± 66.7 | 87% |

TABLE 8-continued

Average Gel Strength Maintenance Percentage before freezing and after rehydration in acidic condition (pH 2, HCl solution) at RT.

| Sample No. | Ingredient and Concentration (w/w) | Average Gel strength before freezing (g) | Average Gel strength at 24 hours after rehydration in acidic solution (pH 2, HCl) at RT. (g) | Average Gel strength maintenance % |
|---|---|---|---|---|
| 6 | Gum (0.4%) Seaweed composite material from *Gracilaria* (0.2%), seaweed composite material from *Eucheuma* (0.5%), and Konjac (0.5%) | 534 ± 35 | 682 ± 169.8 | 128% |
| 7 | Seaweed composite material from *Gracilaria* (0.3%), Konjac (0.3%), and xanthan gum (0.3%) | 487 ± 42 | 324 ± 36.8 | 309% |
| 14 | Seaweed composite material from *Gracilaria* (1%) | 474 ± 14 | 1466 ± 201.8 | 209% |

Sample preparation for samples before freezing: For each Sample, the respective ingredients, as shown in Table 7, were added into deionized (DI) water and boiled for 5 minutes. Then resulting mixture was cooled at room temperature for 15 hours to form the gel. The gel was then cut into cube shape of 3*3*3 cm and measured by texture analyzer.

Sample preparation for samples rehydrated in acidic condition (HCl solution, pH 7) at RT: For each Sample, the respective ingredients, as shown in Table 7, were added into DI water and boiled for 5 minutes. Then the resulting mixture was cooled at room temperature for 15 hours to form the gel. The gel was then kept frozen at −5° C. for 48 hours before it was thawed under room temperature. It was then dehydrated to moisture level of about 10%. Cube shape gel pieces were taken at 3 cm*3 cm (it was 3 cm thick before freezing), the gel pieces were soaked in HCl solution (pH 2) at room temperature (about 20° C.) for 24 hours, then the gel strength was measured for each Sample.

Gel strength measurements: Gel strength measurements were conducted using Texture Analyzer (TA.XT plus, Stable Micro Systems Ltd) with probe P/0.5. The gel strength measurement was carried out at compression speed of 0.3 mm/s and compression height of 15 mm. Gel rupture force was captured (unit: g). Three to six replicates were measured and average was taken.

Advantageously, as shown in Table 8, at 24 hours after rehydration in acidic condition (pH 2, HCl solution), Sample No. 1 had an average gel strength maintenance percentage of 87%, Sample No. 6 was 128%, Sample No. 7 was 309%, and Sample No. 14 was 209%. The Average gel strength maintenance percentage (%)=Average gel strength after rehydration/Average gel strength before freezing. Notably, this shows that these superabsorbent material exhibits excellent tolerance in human gastric condition because it is able to maintain a gel strength maintenance percentage of at least 87% under acidic conditions for at least 24 hours after rehydration.

Also, advantageously, Table 8 shows that when rehydrated in acidic solution, these superabsorbent materials can maintain and even improve its gel strength at 24 hours after rehydration compared to the gel before freezing.

Additional Examples Using Seaweed Composite Material from *Laminaria*.

Sample Nos. 17-18 present additional examples containing seaweed composite material from *Laminaria*, which belongs to seaweed Phaeophyta. The respective ingredients and concentrations (w/w) of Sample Nos. 17-18 are shown in Table 9. The seaweed composite material from *Laminaria* has about 4.7% insoluble fiber (cellulose) and about 32.6% soluble fiber (fucans, glucans and alginates). The seaweed composite material from *Laminaria* may be produced by the methods disclosed herein and in PCT Application No. PCT/US2020/070160, filed on Jun. 19, 2020 and published as WO2020/257825 on Dec. 24, 2020 (which is herein incorporated in its entirety by reference), and PCT Application No. PCT/US2020/070161, filed on Jun. 19, 2020 and published as WO2020/257826 on Dec. 24, 2020 (which is herein incorporated in its entirety by reference).

The seaweed composite material from *Gracilaria* was obtained as described herein and in PCT Application No. PCT/US2020/070160, filed on Jun. 19, 2020 and published as WO2020/257825 on Dec. 24, 2020 (which is herein incorporated in its entirety by reference) (Sample A-2), and has about 29.4% insoluble fiber and about 45.7% soluble fiber. The seaweed composite material from *Eucheuma* was obtained as described herein and in PCT Application No. PCT/US2020/070161, filed on Jun. 19, 2020 and published as WO2020/257826 on Dec. 24, 2020 (which is herein incorporated in its entirety by reference) (Sample L), has about 39.5% insoluble fiber and about 26.0% soluble fiber.

TABLE 9

| Sample No | Ingredients and Concentrations (w/w) | Total water-soluble polysaccharide to total insoluble fiber | WRC at pH 7.0 | WRC at pH 1.0 |
|---|---|---|---|---|
| 17 | Seaweed composite material from *Gracilaria* (1%) and Seaweed composite material from *Laminaria* (1%) | About 2.30 | 21.1 | 12.8 |
| 18 | Seaweed composite material from *Gracilaria* (0.2%), Konjac Gum (0.5%), Seaweed composite material from *Euchuema* (0.5%), and Seaweed composite material from *Laminaria* (1.0%) | About 3.46 | 31.6 | 14.1 |

Sample preparation: For each of Sample Nos. 17-18, all ingredients were added to water at the concentrations provided in Table 9, stirred and dispersed uniformly at high speed, and heated and boiled for 5 minutes to fully dissolve the water-soluble ingredients. The mixture was then cooled to 20-25° C. and left to stand for more than 6 hours to form a gel. The gel was stored below −10° C. for 24 hours to completely freeze the gel. The frozen gel was thawed in air at 20-30° C., or immersed in 20-30° C. water. Subsequently, the thawed gel was filtered or centrifuged, followed by drying with hot air at 50-60° C. to reach a moisture content of less than about 15%.

Water Absorption: Sample Nos. 17-18 were each rehydrated at room temperature with water (pH 7.0) for 24 hours, and rehydrated at room temperature in an acidic solution (pH 1.0) for 24 hours. As demonstrated in Table 9, Sample No. 17 exhibited water retention capacity (WRC) of 21.1 at 24 hours after rehydration in water (pH 7.0), and WRC of 12.8 at 24 hours after rehydration in acidic solution (pH 1.0). Sample No. 18 exhibited WRC of 31.6 at 24 hours after rehydration in water (pH 7.0), and WRC of 14.1 at 24 hours after rehydration in acidic solution (pH 1.0).

Preparation Method for Seaweed Composite Material Having Agar, Such as Seaweed Composite Material from *Gracilaria*.

The preparation method for seaweed composite material having agar, such as seaweed composite material from *Gracilaria*, in general includes the steps of treating the seaweed by one or more alkalis and/or one or more acids. The bleaching step is optional to remove the natural color of the seaweed product, if desired. The seaweed is subjected to preliminary grinding including dry grinding or wet milling, high pressure homogenization under room temperature, and drying and grinding into the final agar-cellulose composite materials having a desired particle size. If desired, the high pressure homogenization can be carried out at a higher temperature to melt the agar, and the process further requires gelling by cooling and dehydration of the agar gel. The seaweeds suitable for this disclosure include all fresh or dried red algae belonging to the Rhodophyceae class, also known as the agarophytes or agar-containing seaweeds, Examples include but are not limited to, *Gracilaria, Gelidium, Porphyra, Pterocladia, Ahnfeltia, Gelidium micropterum, Gelidium pusillum, Gelidiella acerosa, Gelidiopsis variabilis, Gracilaria edulis, Gracilaria Salicornia, Gracilaria dura, Gracilaria corticate, G. corticata* v. *cylindrica, Gracilaria folifera, Gracilaria textorii, Gracilaria fergusonii, Gracilaria crassa, Gracilaria debilis, Gracilaria verrucose,* and *Gelidium corneum,* or a combination of two or more of the above species of red algae.

Figure 8:
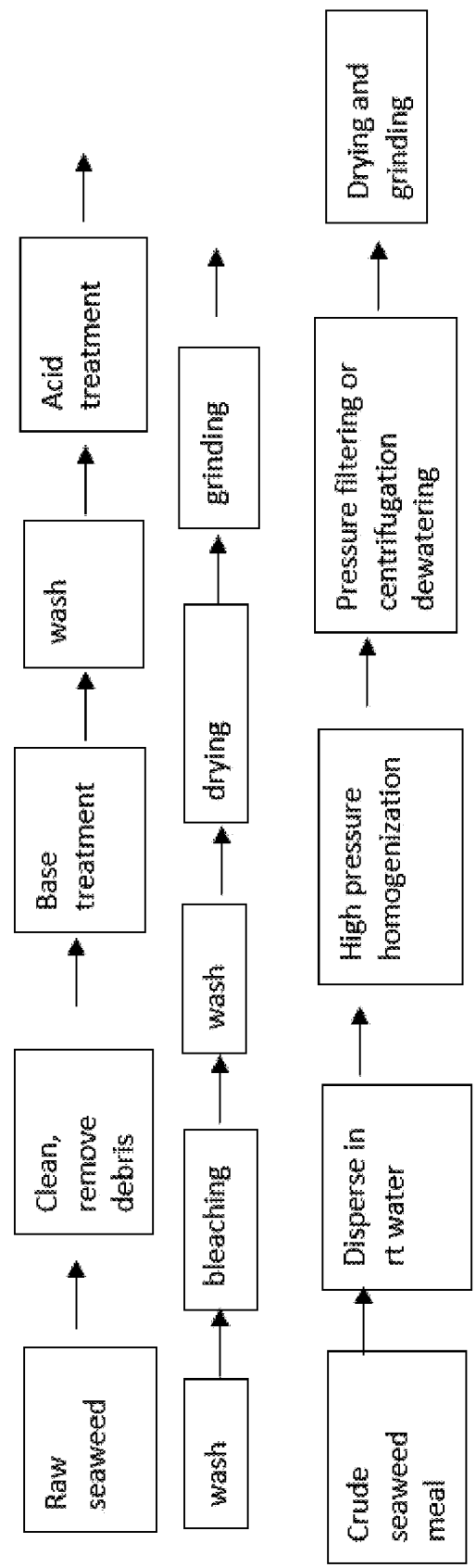
FIG. 8 shows an exemplary embodiment of a preparation method for a seaweed composite material, which uses alkali treatment followed by acid treatment, and dry grinding before high pressure homogenization.

FIG. 8 provides a preparation method in which alkali treatment followed by acid treatment, and dry grinding before high pressure homogenization is provided. Generally, these steps in FIG. 8 include: (1) The raw fresh or dried seaweed is cleaned by washing and removing debris; (2) The cleaned seaweed is treated with an alkali solution, followed by a wash with water to a neutral pH to obtain alkali-treated seaweed; (3) The alkali treated seaweed is treated with an acid solution, followed by a wash to a neutral pH; (4) Optionally, the acid-treated seaweed is treated with one or more bleaching agents, followed by a wash to remove the bleaching agent; (5) The obtained seaweed is dehydrated and dried to a water content of less than or about 20%, and pulverized to 80 mesh or more to obtain a crude seaweed powder; (6) The crude seaweed powder is dispersed in water at a temperature of 0-50° C. and then processed by high-pressure homogenization at a pressure of 10-100 MPa, and then subjected to pressure filtration or centrifugal dewatering, and dried to a water content of 20% or less; and (7) The dried seaweed is pulverized to 80 mesh or more to obtain the final seaweed composite material.

Figure 9:
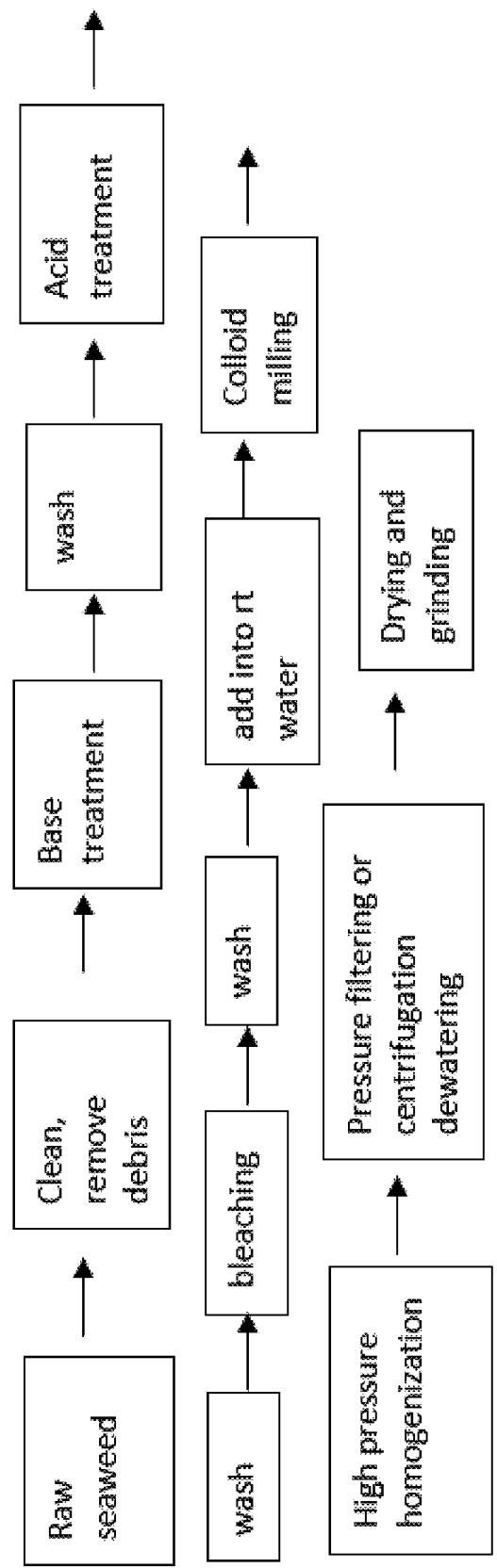
FIG. 9 shows another exemplary embodiment of a preparation method for a seaweed composite material, which uses alkali treatment followed by acid treatment, and colloid milling before high pressure homogenization.

FIG. 9 provides a preparation method in which alkali treatment followed by acid treatment, and Colloid milling before high pressure homogenization. Generally, these steps in FIG. 9 include: (1) The raw fresh or dried seaweed is cleaned by washing and removing debris; (2) The cleaned seaweed is treated with an alkali solution, followed by a wash with water to a neutral pH to obtain alkali-treated seaweed; (3) The alkali treated seaweed is treated with an acid solution, followed by a wash to a neutral pH; (4) Optionally, the acid-treated seaweed is treated with one or more bleaching agents, followed by a wash to remove the bleaching agent; (5) The seaweed is added to water at a temperature of 0-50° C. and wet milled by colloid milling; (6) The milled seaweed is processed by high-pressure homogenization at a pressure of 10-100 MPa, and then subjected to pressure filtration or centrifugal dewatering, and dried to a water content of 20% or less; and (7) The dried seaweed is pulverized to 80 mesh or more to obtain the final seaweed composite material.

Figure 10:
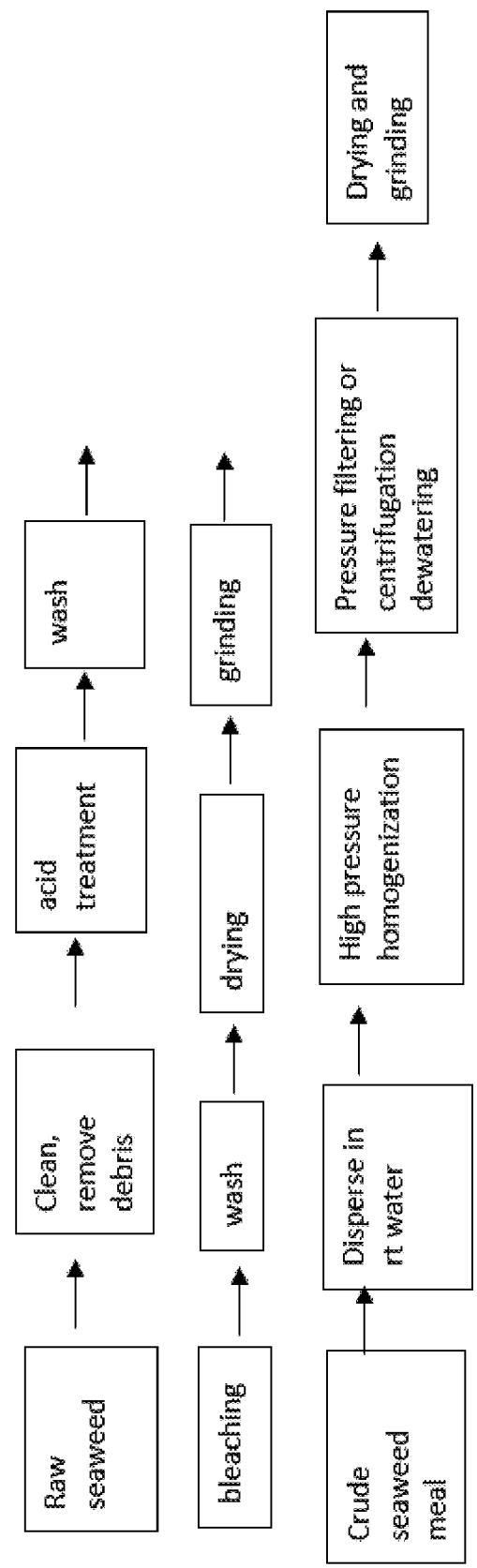
FIG. 10 shows another exemplary embodiment of a preparation method for a seaweed composite material, which uses acid treatment without alkali treatment, and dry grinding before high pressure homogenization.

FIG. 10 presents another preparation method for seaweed composite material and specifically, acid treatment without alkali treatment and dry grinding before high pressure homogenization.

In general, the steps in FIG. 10 include: (1) The raw or dried seaweed is cleaned by washing and removing debris; (2) The cleaned seaweed is treated with an acid solution, followed by a wash to a neutral pH; (3) Optionally, the acid-treated seaweed is treated with one or more bleaching agents, followed by a wash to remove the bleaching agent; (4) The obtained seaweed is dehydrated and dried to a water content of less than or about 20%, and pulverized to 80 mesh or more to obtain a crude seaweed powder; (5) The crude seaweed powder is dispersed in water at a temperature of 0-50° C. and then processed by high-pressure homogenization at a pressure of 10-100 MPa, and then subjected to pressure filtration or centrifugal dewatering, and dried to a water content of 20% or less; and (7) The dried seaweed is pulverized to 80 mesh or more to obtain the final seaweed composite material.

Figure 11:
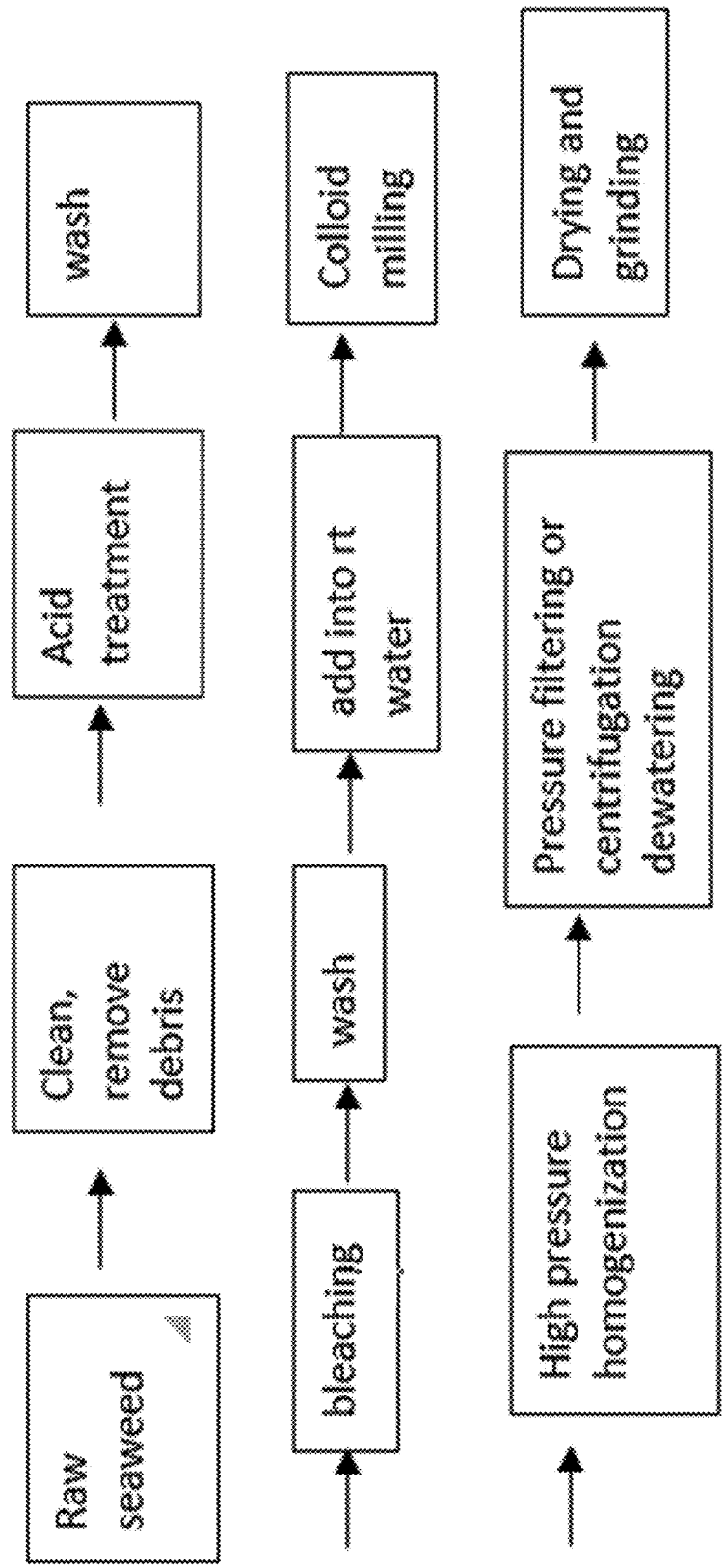
FIG. 11 shows another exemplary embodiment of a preparation method for a seaweed composite material, which uses acid treatment without alkali treatment, and colloid milling before high pressure homogenization.

FIG. 11 presents another preparation method for seaweed composite material and specifically, acid treatment without alkali treatment and colloid milling before high pressure homogenization. In general, the steps in Figure include: (1) The raw fresh or dried seaweed is cleaned by washing and removing debris; (2) The cleaned seaweed is treated with an acid solution, followed by a wash to a neutral pH; (3) Optionally, the acid-treated seaweed is treated with one or more bleaching agents, followed by a wash to remove the bleaching agent; (4) The seaweed is added to water at a temperature of 0-50° C. and wet milled by colloid milling; (5) The milled seaweed is processed by high-pressure homogenization at a pressure of 10-100 MPa, and then subjected to pressure filtration or centrifugal dewatering, and dried to a water content of 20% or less; and (6) The dried seaweed is pulverized to 80 mesh or more to obtain the final seaweed composite material.

Figure 12:
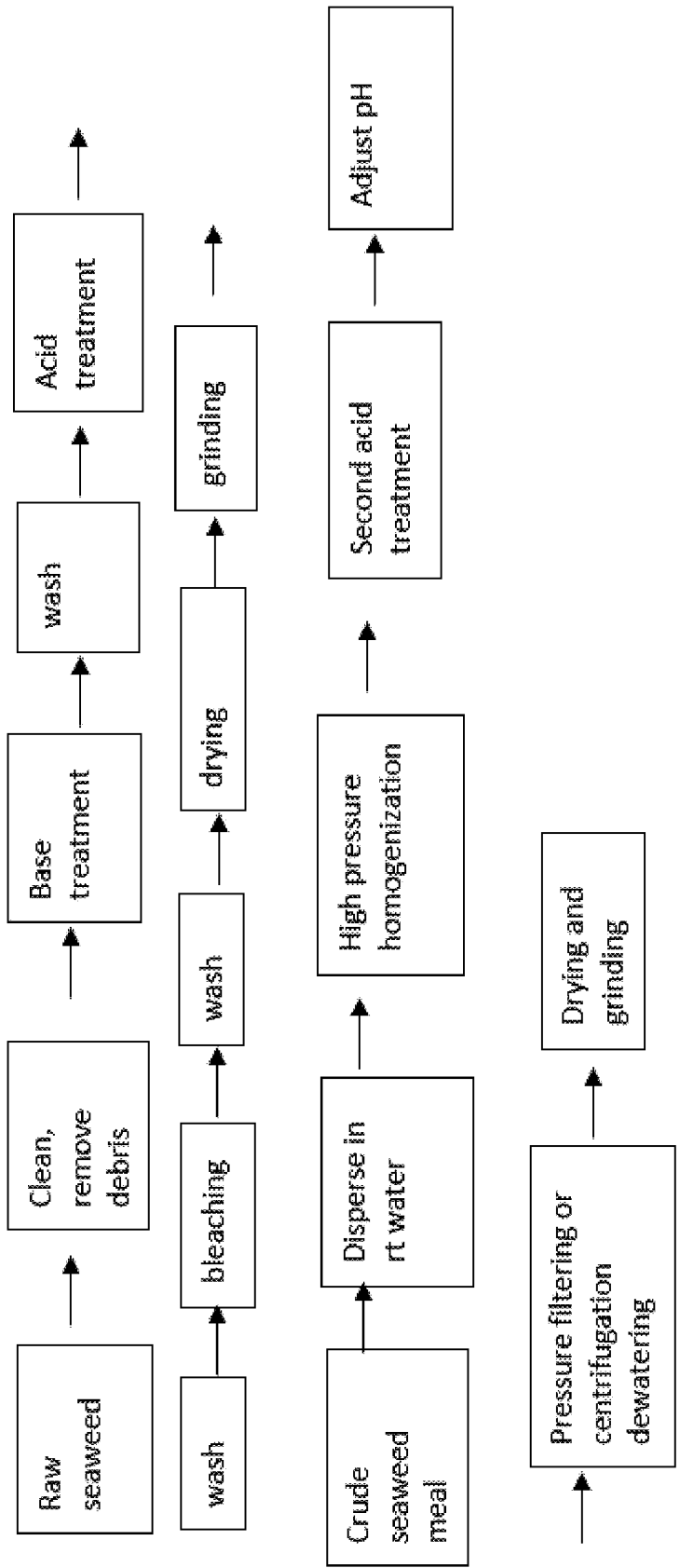
FIG. 12 shows another exemplary embodiment of a preparation method for a seaweed composite material, which uses alkali treatment followed by double acid treatments, and dry grinding before high pressure homogenization

FIG. 12 presents another preparation method for seaweed composite material and specifically, alkali treatment followed by double acid treatments and dry grinding before high pressure homogenization. In general, the steps in FIG. 12 include: (1) The raw fresh or dried seaweed is cleaned by washing and removing debris; (2) The cleaned seaweed is treated with an alkali solution, followed by a wash with water to a neutral pH to obtain alkali-treated seaweed; (3) The alkali treated seaweed is treated with an acid solution, followed by a wash to a neutral pH; (4) Optionally, the acid-treated seaweed is treated with one or more bleaching agents, followed by a wash to remove the bleaching agent; (5) The obtained seaweed is dehydrated and dried to a water content of less than or about 20%, and pulverized to 80 mesh or more to obtain a crude seaweed powder; (6) The crude seaweed powder is dispersed in water at a temperature of 0-50° C. and then processed by high-pressure homogenization at a pressure of 10-100 MPa; (7) The homogenized liquid is treated with an acid solution (0.1-3% w/w) for 5-20 hours at a temperature of 0-50° C., followed by adjusting the pH to neutral with an alkali; (8) The sample is subjected to pressure filtration or centrifugal dewatering, and dried to a water content of 20% or less; and (9) The dried seaweed is pulverized to 80 mesh or more to obtain the final seaweed composite material.

Figure 13:
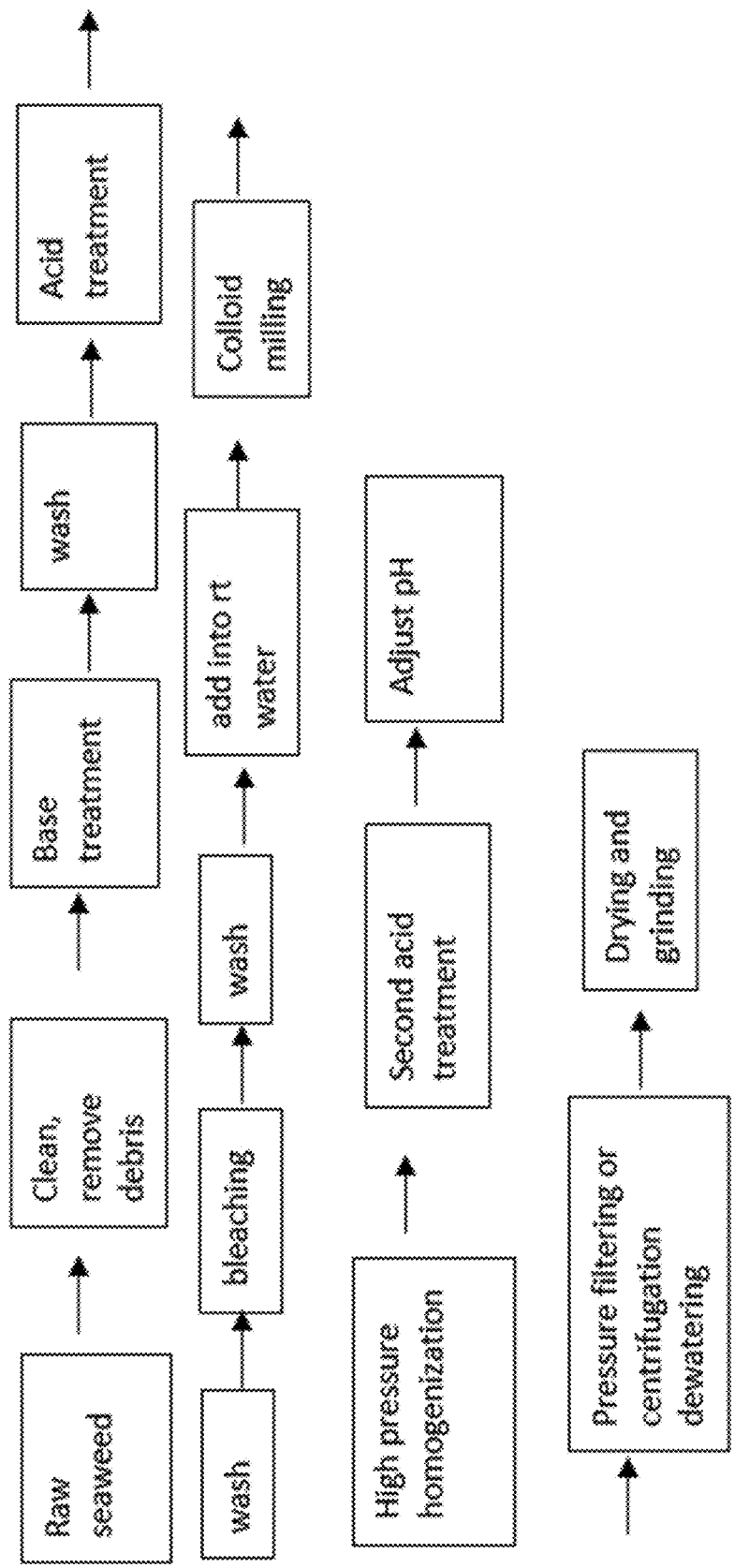
FIG. 13 shows another exemplary embodiment of a preparation method for a seaweed composite material, which uses alkali treatment followed by double acid treatments, and colloid milling before high pressure homogenization.

FIG. 13 presents another preparation method for seaweed composite material and specifically, alkali treatment followed by double acid treatments and colloid milling before high pressure homogenization. In general, the steps in FIG. 13 include: (1) The raw fresh or dried seaweed is cleaned by washing and removing debris; (2) The cleaned seaweed is treated with an alkali solution, followed by a wash with water to a neutral pH to obtain alkali-treated seaweed; (3) The alkali treated seaweed is treated with an acid solution, followed by a wash to a neutral pH; (4) Optionally, the acid-treated seaweed is treated with one or more bleaching agents, followed by a wash to remove the bleaching agent; (5) The seaweed is added to water at a temperature of 0-50° C. and wet milled by colloid milling; (6) The milled seaweed is processed by high-pressure homogenization at a pressure of 10-100 MPa; (7) The homogenized liquid is treated with an acid solution (0.1-3% w/w) for 5-20 hours at a temperature of 0-50° C., followed by adjusting the pH to neutral with an alkali; (8) The sample is subjected to pressure filtration or centrifugal dewatering, and dried to a water content of 20% or less; and (7) The dried seaweed is pulverized to 80 mesh or more to obtain the final seaweed composite material.

For all three processes disclosed above for the preparation method for seaweed composite material having agar, such as seaweed composite material from *Gracilaria*, a sample of each intermediate product before HPH was saved and added to hot water to melt and dissociate the agar from the cellulose matrix and then the HPH was performed at a higher temperature (60-100° C.), followed by cooling, gelling and dehydration. The cellulose fiber can be broken down more efficiently at a higher temperature, or the cellulose fiber can be efficiently broken down at room temperature with more stringent HPH conditions (e.g. higher pressure or multiple passes). There are recognizable differences in the agar-cellulose composite materials obtained by these two different ways. HPH at room temperature results in much more evenly distributed agar-cellulose composite particles with grainy particles containing cellulose fiber mostly encapsulated by agar. On the other hand, HPH under high temperature results in a sample that is highly variable in particle sizes and shapes, where some particles seem to have large amount cellulose fiber surrounded by a thin layer of agar, and others seem to be made mostly of agar without fibers. This sample also contains many flakes of agar gel pieces. These observations suggest that HPH under high temperature causes the melting and dissociation of agar. During the cooling and gelling process, some cellulose fiber particles associate to each other to form large clusters in the agar gel, leaving some region with high content of cellulose and other regions devoid of cellulose.

Thus, the disclosed technology entails breaking down seaweed cell wall at room temperature to expose agar as gelling agents and to modify the structure of the cellulose fiber by reducing its size and/or increasing the exposed surface area to obtain a natural seaweed composite material. Although high pressure homogenization is used in working examples of this disclosure, the technology is not limited to HPH but rather including any methods that can break down seaweed cell wall while maintaining agar in its un-melted, native state bound to the cellulose. Because agar is porous and permeable to aqueous and the particle size is small enough (less than 90 μm in diameter) to allow chemical and mechanical treatment of the bound cellulose, this process is compatible with other established methods to modify the structure and function of agar and the cellulose for specific applications. The manufacturing process may vary depending on the species of seaweeds and the desired properties of the final agar-cellulose composite materials.

In addition to increase gelling strength, alkali treatment can also destroy part of the pigment and protein in raw seaweed to facilitate decolorization and deproteinization. The alkali that can be used in the disclosed process include sodium hydroxide, potassium hydroxide, calcium hydroxide or the like. The concentration of the alkalis and processing conditions such as temperature and treatment time can vary. For example, (A) a high alkali concentration at a low temperature (e.g., 20-30% sodium hydroxide at room temperature for 5-10 days), (B) a medium alkali concentration at a medium temperature (e.g., 20-30% sodium hydroxide at 60-70° C. for 1-4 hours), and (C) a low alkali concentration at a high temperature (e.g., 2-7% sodium hydroxide solution at 80-95° C. for 1-4 hours) can be used. Condition (C) requires a small amount of alkali and a short reaction time. However, the hydrocolloid is easily dissolved and lost, and the gelling strength and overall quality of the obtained seaweed composite material is slightly compromised. This process is suitable for large production due to its production efficiency. Condition (A) reduces the loss of hydrocolloid, and the gelling strength and quality of the seaweed composite material is improved, but the production cycle is long, the efficiency is low, and the consumption of alkali is high. The alkali treatment conditions can be further optimized based on the raw materials and the desired features of the final product.

Seaweed with or without alkali-treatment can be subjected to acid treatment. The acid is one or more of phosphoric acid, hydrochloric acid, sulfuric acid, oxalic acid, citric acid, lactic acid, malic acid, acetic acid, and the like. The acid treatment is carried out to remove some salt components in the seaweed, and/or to soften the seaweed for subsequent bleaching treatment. The acid treatment is generally carried out at 50° C., at a concentration of 0.1-1% (w/w), and the treatment time is between 10 minutes and 2 hours. The acid concentration and treatment time can vary based on the species of the raw seaweed materials. Excessive acid treatment may cause hydrocolloid loss and decreased gelling strength.

Bleaching treatment is optional and can remove the natural colorants in seaweed to enhance the whiteness of the product. Bleaching is usually carried out at room temperature. The bleaching agent is one or more of hydrogen peroxide, sodium hypochlorite, chlorine dioxide, and the like. Preferably, a sodium hypochlorite solution is used as the bleaching solution, the effective chlorine concentration is about 0.1-0.5%, and the treatment time is about 30 minutes to 2 hours.

The bleached seaweed can be dried first, coarsely pulverized, and then added to 0-50° C. water or 60-100° C. water to carry out high pressure homogenization. Alternatively, after removal of the bleaching agent the wet seaweed can be directly added to 0-50° C. water or 60-100° C. water for wet milling using colloid milling, followed by high pressure homogenization. The material homogenized in 0-50° C. water can be dried by centrifugation or pressure filtration, and then dried and pulverized into the final product. The material homogenized in 60-100° C. water needs to be cooled to form a gel first, then dewatering by pressure filtration or freeze dry by lyophilization. The dried sample is pulverized into the final product.

After alkali-treatment and high pressure homogenization, the homogenized seaweed liquid can be subjected to a second acid treatment to obtain low molecular weight agar containing seaweed composite materials having a low-gelling strength (e.g., a gelling strength ≤200 g/cm$^2$). The second acid treatment can be carried out at a lower temperature (0-50° C.) for a longer period, for example, at an acid concentration of 0.1-3% (w/w) for 5-20 hours. It can also be carried out at a relatively high temperature (60-100° C.) for a short period of time, for example, at an acid concentration of 0.01-1.0% (w/w) for 0.5-2 hours.

Colloid mill is a type of wet milling equipment that can reduce particle size by shearing and milling. High pressure homogenization can reduce particle size by high mechanical shearing forces. HPH can also loosen the structure of certain materials including insoluble plant fibers through entropic effect resulting from the dramatic drop of pressure associated with HPH. Natural cellulose fiber from plants including seaweeds are usually densely packed resulting in hard texture, poor mouthfeel and water binding properties. HPH treatment has been used to modify various plant derived fibers in a dissociated state to reduce particle size, disrupt fibrous structure and increase surface area, thereby to enhance their food application quality (e.g. water binding and retention capacity and viscosity and stability etc.). Unexpectedly, as it is disclosed herein, HPH can achieve a significant effect on breaking down seaweed cellulose fiber in the presence of naturally bound agar. Thus, the disclosed process of making a natural agar-cellulose composite material wherein the originally densely packed seaweed fiber bundles are broken into small fiber pieces even when the fiber is in a state associated with agar and the association is maintained despite of the shearing force of HPH.

After the dry-grind seaweed powder is dispersed in water, or wet-milled seaweed sample is obtained, it is filtered by a cloth of 40 mesh or more, more preferably, 80-100 mesh or more, to prepare the sample for HPH. The HPH can be carried out in a single pass or multiple passes. For a single pass, the homogenization pressure is preferably from 20 to 100 MPa, more preferably from 30 to 60 MPa. For multiple passes, the homogenization pressure is preferably from 10 to 60 MPa, more preferably from 20 to 40 MPa.

The drying process can be carried out in many different ways and is not limited by any particular method. The final product is pulverized to 80 mesh or more, more preferably to 200 mesh or more. The actual particle size can be determined by specific applications.

Preparation method for seaweed composite material having carrageenan, such as seaweed composite material from *Eucheuma*.

The preparation method for seaweed composite material having carrageenan, such as seaweed composite material from *Eucheuma*, in general includes the steps of treating the seaweed with high concentration of potassium chloride (KCl) under heat before subjecting the seaweed to high pressure homogenization (HPH). The raw materials used in this disclosure include fresh or dried red algae that are traditionally used to extract carrageenan, including *Kappaphycus alvarezii, Eucheuma denticulatum*, and the like, or a combination thereof. More generally, the raw material of the present invention comprises any carrageenan containing red seaweeds (carrageenophytes) including but not limited to seaweed from the families of Gigartinaceae, Hypneaceae, Solieriaceae, Phyllophoraceae and Furcellariaceae and combinations thereof. Useful genera include *Chondrus, Iridaea, Gigartina, Kappaphycus, Rhodoglossum, Hypnea, Eucheuma, Agarchiella, Gymnogongrus, Phyllophora, Ahnfeltia* and *Furcellaria* and combinations thereof. Useful species include *Eucheuma spinosum, Eucheuma cottonii, Chondrus Crispus, Gigartina skottsbergii, Kappaphycus alvarezii, Eucheuma denticulatum*, and combinations thereof.

The bleaching step is optional to remove the natural color of the seaweed product, if desired. The seaweed is subjected to preliminary grinding including dry grinding or wet milling before or after KCl treatment. The KCl treatment is carried out before high pressure homogenization under heating at 80-100° C. for 1-6 hours, and the HPH can be carried out at low temperature between 0-85° C. without melting carrageenan off from its native plant matrix comprising the insoluble fiber. The HPH-treated seaweed is then dried and ground into the final carrageenan-cellulose composite materials having a desired particle size. If desired, the high pressure homogenization can be carried out at the elevated temperature such as 60-100° C. to melt the carrageenan, and the process further requires gelling by cooling in the presence of a low concentration of KCl. The specific details of the process may vary depending on the different starting raw materials and the desired features of the final product.

Grinding before potassium chloride treatment has a general scheme that includes: Dried seaweed→washing and cleaning→bleaching→drying→pulverization→KCl treatment→high pressure homogenization→pressure filtering dehydration (or heating to above 60° C. to melt carrageenan and add KCl to cool and form a gel, then pressure filtering dehydration)→drying→pulverization to desired particle size.

The process is as follows: (1) The raw fresh or dried seaweed is cleaned by washing and removing impurities and debris; (2) Optionally, the cleaned seaweed is treated with one or more bleaching agents (e.g., sodium hypochlorite, effective chlorine 0.1-0.5%) for 30 minutes to 2 hours, followed by a wash to remove the bleaching agent; (3) The obtained seaweed is dried and pulverized to 80 mesh or more to obtain a crude seaweed powder; (4) The crude seaweed powder is added to a potassium chloride solution of 5-20% (w/w), and treated at 80-100° C. for 1-6 hours, followed by pressure filtration or centrifugal dewatering; (5) The KCl treated seaweed powder is dispersed evenly in water at a mass ratio of 1:20 to 1:100 (seaweed by dry weight to water) at 0-50° C., treated by high-pressure homogenizer at a pressure of 20-50 MPa, and the homogenized liquid is pressure filtered to remove water; alternatively, the seaweed powder is dispersed evenly in water at a mass ratio of 1:20 to 1:100 (seaweed by dry weight to water) at 60-100° C., treated by high-pressure homogenizer at a pressure of 20-50 MPa, and 0.1%-1.0% potassium chloride is added to the homogenized liquid and cooled to 0-40° C. to form a gel, which is dehydrated by pressure filtration; (6) The solid component obtained by pressure filtration in step (5) is dried by hot air or other drying methods and pulverized to 80 mesh or more to obtain the final seaweed composite material.

Grinding after potassium chloride treatment has a general scheme that includes: Dried seaweed→washing and cleaning→KCl treatment→bleaching→washing→drying→pulverization→dispersing in water→high pressure homogenization→pressure filtering dehydration (or heating to above 60° C. to melt carrageenan and add KCl to cool and form a gel, then pressure filtering dehydration)→drying→pulverization to desired particle size The process is as follows: (1) The raw fresh or dried seaweed is cleaned by washing and removing impurities and debris; (2) The cleaned seaweed is added to a potassium chloride solution of 5-20% (w/w), and treated at 80-100° C. for 1-6 hours, followed by washing to remove KCl; (3) Optionally, the KCl-treated seaweed is treated with one or more bleaching agents (e.g., sodium hypochlorite, effective chlorine 0.1-0.5%) for 30 minutes to 2 hours, followed by a wash to remove the bleaching agent;
(4) The obtained seaweed is dried and pulverized to 80 mesh or more to obtain a crude seaweed powder; (5) The seaweed powder is dispersed evenly in water at a mass ratio of 1:20 to 1:100 (seaweed by dry weight to water) at 0-50° C., treated by high-pressure homogenizer at a pressure of 20-50 MPa, and the homogenized liquid is pressure filtered to remove water; alternatively, the seaweed powder is dispersed evenly in water at a mass ratio of 1:20 to 1:100 (seaweed by dry weight to water) at 60-100° C., treated by high-pressure homogenizer at a pressure of 20-50 MPa, and 0.1%-1.0% potassium chloride is added to the homogenized liquid and cooled to 0-40° C. to form a gel, which is dehydrated by pressure filtration; (6) The solid component obtained by pressure filtration in step (5) is dried by hot air or other drying methods and pulverized to 80 mesh or more to obtain the final seaweed composite material.

Wet milling before KCl treatment has a general scheme that includes: Fresh or rehydrated seaweed→washing and cleaning→bleaching→KCl treatment→colloid milling→high pressure homogenization→pressure filtering dehydration (or heating to above 60° C. to melt carrageenan and add KCl to cool and form a gel, then pressure filtering dehydration)→drying→pulverization to desired particle size The process is as follows: (1) The raw fresh or dehydrated seaweed is cleaned by washing and removing impurities and debris; (2) Optionally, the cleaned seaweed is treated with one or more bleaching agents (e.g., sodium hypochlorite, effective chlorine 0.1-0.5%) for 30 minutes to 2 hours, followed by a wash to remove the bleaching agent; (3) The obtained seaweed is added to a potassium chloride solution of 5-20% (w/w), and treated at 80-100° C. for 1-6 hours, followed by washing to remove KCl; (4) The KCl treated seaweed powder is dispersed in water and colloid milled to 80 mesh or more; (5) The seaweed is dispersed evenly in water at a mass ratio of 1:20 to 1:100 (seaweed by dry weight to water) at 0-50° C., treated by high-pressure homogenizer at a pressure of 20-50 MPa, and the homogenized liquid is pressure filtered to remove water; alternatively, the seaweed powder is dispersed evenly in water at a mass ratio of 1:20 to 1:100 (seaweed by dry weight to water) at 60-100° C., treated by high-pressure homogenizer at a pressure of 20-50 MPa, and 0.1%-1.0% potassium chloride is added to the homogenized liquid and cooled to 0-40° C. to form a gel, which is dehydrated by pressure filtration; (6) The solid component obtained by pressure filtration in step (5) is dried by hot air or other drying methods and pulverized to 80 mesh or more to obtain the final seaweed composite material.

Unlike traditional carrageenan extraction by hot alkali treatment, the technology disclosed herein pretreats the seaweed with a high concentration of a salt such as KCl (5-20% w/w) under high temperature (80-100° C.) for an extended period of time (1-6 hours), followed by high-pressure homogenization to obtain a carrageenan-cellulose fiber composite material. Without bound by theory, high concentration of KCl here may serve the role to stabilize carrageenan to prevent its dissolution loss at high temperature. It may also have other effects such as increasing the gelling strength of the isolated carrageenan-cellulose fiber composite materials. Carrageenan is present in the cell wall and intercellular matrix of the seaweed plant tissue together with the cellulose fiber. Heating at a high temperature may have a series of effects on the plant matrix structure, including the structures of a variety of bio-macromolecules and their assembly interactions, leading to a loosened structure that is amenable to further break down by mechanical processes such as high-pressure homogenization.

The concentration of KCl and the treatment time may vary depending on the type and state of the starting seaweed raw materials. In general, when the whole seaweed plant is used, the required KCl concentration is higher and the treatment time is longer. The concentration can be lower and the treatment time shorter after the seaweed has been pulverized (in dry form) or wet milled by colloid milling. The advantage of using whole seaweed is that it is easier to carry out washing between various steps of the processes, including removing the salt after the high concentration KCl treatment. The advantage of using pulverized or milled seaweed powder is that the high salt heating treatment could be carried out in relatively mild conditions (for example, lower KCl concentration and shorter heating time etc.). Therefore, the mild conditions help in preparing a natural carrageenan/cellulose composite containing additional natural compounds from seaweeds that may be lost or denatured under harsh conditions such as longer heating time.

Bleaching treatment is optional and can remove the natural colorants in seaweed to enhance the whiteness of the product. Bleaching is usually carried out at room temperature. The bleaching agent is one or more of hydrogen peroxide, sodium hypochlorite, chlorine dioxide, and the like. Preferably, a sodium hypochlorite solution is used as the bleaching solution, the effective chlorine concentration is about 0.1-0.5%, and the treatment time is about 30 minutes to 2 hours.

The bleached seaweed can be dried first, coarsely pulverized, and then added to 0-50° C. water or 60-100° C. water to carry out high pressure homogenization. Alternatively, after removal of the bleaching agent the wet seaweed can be directly added to 0-50° C. water or 60-100° C. water for wet milling using colloid milling, followed by high pressure homogenization. The material homogenized in 0-50° C. water can be dried by centrifugation or pressure filtration, and then dried and pulverized into the final product. The material homogenized in 60-100° C. water needs to be cooled to form a gel in the presence of a low concentration of KCl first, then dewatering by pressure filtration or freeze dry by lyophilization. The dried sample is pulverized into the final product.

The crude seaweed powder can be dispersed in water at 0-50° C. or at 60-100° C. and then subjected to HPH. Alternatively, the pretreated whole seaweed can be directly added to 0-50° C. or 60-100° C. water for wet milling using a colloid mill, followed by high pressure homogenization.

When homogenized at 0-50° C., the water-soluble polysaccharides including carrageenan remain in their natural unmelted state, and the resulting carrageenan-fiber composite material can be isolated by centrifugation or pressure filtration, dried and pulverized into final product. When homogenized in water at 60-100° C., the water-soluble polysaccharides including carrageenan are partially or mostly dissolved into water and separated from their natural seaweed plant matrix. The materials need to be cooled to form gel first, then dewatering by pressure filtration or freeze dry by lyophilization. The dried sample is pulverized into final product of desired particle size.

Colloid mill is a type of wet milling equipment that can reduce particle size by shearing and milling. High pressure homogenization can reduce particle size by high mechanical shearing forces. HPH can also loosen the structure of certain materials including insoluble plant fibers through entropic effect resulting from the dramatic drop of pressure associated with HPH. Natural cellulose fiber from plants including seaweeds are usually densely packed resulting in hard texture, poor mouthfeel and water binding properties. HPH treatment has been used to modify various plant derived fibers in a dissociated state to reduce particle size, disrupt fibrous structure and increase surface area, thereby to enhance their food application quality (e.g. water binding and retention capacity and viscosity and stability etc.). Unexpectedly, as it is disclosed herein, HPH can achieve a significant effect on breaking down seaweed cellulose fiber in the presence of naturally bound carrageenan. Thus, the disclosed process of making a natural carrageenan-cellulose composite material wherein the originally densely packed seaweed fiber bundles are broken into small fiber pieces even when the fiber is in a state associated with carrageenan and the association is maintained despite of the shearing force of HPH.

After the dry-grind seaweed powder is dispersed in water, or wet-milled seaweed sample is obtained, it is filtered by a cloth of 40 mesh or more, more preferably, 80-100 mesh or more, to prepare the sample for HPH. The HPH can be carried out in a single pass or multiple passes. For a single pass, the homogenization pressure is preferably from 20 to 100 MPa, more preferably from 30 to 60 MPa. For multiple passes, the homogenization pressure is preferably from 10 to 60 MPa, more preferably from 20 to 40 MPa.

The drying process can be carried out in many different ways and is not limited by any particular method. The final product is pulverized to 80 mesh or more, more preferably to 200 mesh or more. The actual particle size can be determined by specific applications.

The invention claimed is:

1. A method of preparing a superabsorbent material comprising:
   mixing one or more water-soluble polysaccharides and one or more insoluble fibers to form a mixture;
   forming a gel from the mixture;
   freezing the gel; and
   drying the gel to obtain the superabsorbent material.

2. The method of claim 1, further comprising:
   dissolving the one or more water-soluble polysaccharides in water to form a solution;
   adding the one or more insoluble fibers to water to form a dispersion; and
   mixing the solution containing the one or more soluble polysaccharides and the dispersion containing the one or more insoluble fibers to form the mixture.

3. The method of claim 1, wherein the freezing induces cryogelation.

4. The method of claim 2, further comprising subjecting the dispersion to high pressure homogenization before mixing with the solution.

5. The method of claim 1, wherein the drying comprises:
   thawing the gel to obtain a thawed gel; and
   drying the thawed gel.

6. The method of claim 1, wherein the drying comprises drying by lyophilization.

7. The method of claim 1, further comprising pulverizing the gel after drying to obtain the superabsorbent material in a powder form.

8. The method of claim 1, wherein the one or more insoluble fibers are selected from the group consisting of insoluble fiber in soybean fiber, insoluble fiber from seaweeds, insoluble fiber in seaweed composite material, cellulose, insoluble hemicellulose, lignin of seeds, seed skins, roots, stems, leaves, barks from legume, whole grain, vegetables, fruits, beans, seeds, seed skins, and whole grains, oat fiber, rice fiber, corn fiber, citrus fiber, beet fiber, sugarcane fiber, coconut fiber, and combinations thereof.

9. The method of claim 1, wherein the ratio by weight between the one or more water-soluble polysaccharides and the the one or more insoluble fibers is between about 1:1 and about 30:1.

10. The method of claim 1, wherein the one or more water-soluble polysaccharides comprise:
    (i) one or more gelling polysaccharides,
    (ii) one or more gelling-compatible polysaccharides, or
    (iii) both one or more gelling polysaccharides and one or more gelling-compatible polysaccharides.

11. The method of claim 1, wherein the superabsorbent material has a porous network structure without chemical cross-linking.

12. The method of claim 1, wherein the superabsorbent material has a volume expansion ratio of at least 10 times or up to 150 times in less than 2 hours.

13. The method of claim 1, wherein the superabsorbent material has a porous network structure with a plurality of pores with a two-dimensional pore density in a range of 1 per 100 micrometers squared ($\mu m^2$) to 500 per 100 micrometers squared ($\mu m^2$) and the pores have an average diameter size in the range of 1 micrometer ($\mu m$) to 30 micrometers ($\mu m$).

14. The material of claim 10, further comprising at least one of:
    the one or more gelling polysaccharides are selected from the group consisting of agar, carrageenan, konjac gum, psyllium husk, alginate, pectin, gellan, chitosan, and curdlan;
    the one or more gelling-compatible polysaccharides are selected from the group consisting of xanthan gum, locust bean gum, guar gum, tamarind seed gum, okara, and gum acacia; or
    the one or more insoluble fibers are selected from the group consisting of insoluble fiber in soybean fiber, insoluble fiber from seaweeds, insoluble fiber in seaweed composite materials, cellulose, insoluble hemicellulose, lignin of seeds, seed skins, roots, stems, leaves, barks from legume, whole grain, vegetables, fruits, beans, seeds, seed skins, and whole grains, oat fiber, rice fiber, corn fiber, citrus fiber, beet fiber, sugarcane fiber, coconut fiber, and combinations thereof.

15. The method of claim 1, comprising:
    the one or more insoluble fibers in the superabsorbent material in total is between about 15% (w/w) and about 85% (w/w); or
    the one or more water-soluble polysaccharides in the superabsorbent material in total is between about 15% (w/w) and about 85% (w/w).

16. The method of claim 1, wherein upon hydration at room temperature, the superabsorbent material expands in volume in less than 2 hours, and maintains a well-defined structure:
- as characterized by a gel strength of at least 50 grams, for at least 24 hours under a neutral pH condition or a human gastric pH condition; or
- characterized by a storage modulus (G') of $10^3$ to $10^6$ Pa, for at least 24 hours under a neutral pH condition or a human gastric pH condition.

17. The method of claim 1, further comprising hydrating the superabsorbent material to form a hydrated gel without homogenizing or mechanically dispersing the insoluble fibers.

18. The method of claim 1, comprising forming the superabsorbent material without:
- expansion with a gas; or
- digestion with an enzyme.

19. A method of preparing a superabsorbent material comprising:
- dissolving one or more water-soluble polysaccharides in water to form a solution;
- adding one or more insoluble fibers to water to form a dispersion;
- mixing the solution containing the one or more soluble polysaccharides and the dispersion containing the one or more insoluble fibers to form a mixture;
- subjecting the mixture to suitable conditions to form a gel;
- freezing the gel to obtain a frozen gel; and
- thawing the frozen gel to obtain a thawed gel; and
- drying the thawed gel to obtain the superabsorbent material having a porous network structure without chemical cross-linking.

20. A method of preparing a superabsorbent material comprising:
- dissolving one or more water-soluble polysaccharides in water to form a solution;
- adding one or more insoluble fibers to water to form a dispersion;
- mixing the solution containing the one or more soluble polysaccharides and the dispersion containing the one or more insoluble fibers to form a mixture;
- subjecting the mixture to suitable conditions to form a gel;
- freezing the gel to obtain a frozen gel; and
- drying the frozen gel by lyophilization to obtain the superabsorbent material having a porous network structure without chemical cross-linking.

* * * * *